US008586022B2

(12) United States Patent
Szalay et al.

(10) Patent No.: US 8,586,022 B2
(45) Date of Patent: *Nov. 19, 2013

(54) LIGHT EMITTING MICROORGANISMS AND CELLS FOR DIAGNOSIS AND THERAPY OF TUMORS

(75) Inventors: Aladar A. Szalay, Highland, CA (US); Yong A. Yu, San Diego, CA (US); Tatyana Timiryasova, Scotrun, PA (US); Shahrokh Shabahang, Redlands, CA (US)

(73) Assignee: Genelux Corporation, San Diego, CA (US)

( * ) Notice: Subject to any disclaimer, the term of this patent is extended or adjusted under 35 U.S.C. 154(b) by 339 days.

This patent is subject to a terminal disclaimer.

(21) Appl. No.: 11/981,976

(22) Filed: Oct. 31, 2007

(65) Prior Publication Data

US 2009/0117047 A1    May 7, 2009

Related U.S. Application Data

(63) Continuation of application No. 10/866,606, filed on Jun. 10, 2004, which is a continuation of application No. 10/189,918, filed on Jul. 3, 2002, now abandoned.

(30) Foreign Application Priority Data

Jul. 31, 2001  (EP) ..................................... 01118417
Oct. 30, 2001  (EP) ..................................... 01125911

(51) Int. Cl.
*A01N 63/00*  (2006.01)
*A61K 48/00*  (2006.01)
*A61B 5/055*  (2006.01)
*C07H 21/04*  (2006.01)

(52) U.S. Cl.
USPC .............. 424/93.2; 424/9.3; 424/93.6; 435/8; 435/968; 536/23.5; 536/23.7

(58) Field of Classification Search
USPC ..................... 424/9.3, 93.2, 93.6; 435/8, 968; 536/23.5, 23.7
See application file for complete search history.

(56) References Cited

U.S. PATENT DOCUMENTS

| | | | |
|---|---|---|---|
| 4,216,226 A | 8/1980 | Fukuyasu et al. | 514/546 |
| 4,315,914 A | 2/1982 | Arakawa et al. | 424/281.1 |
| 4,442,203 A | 4/1984 | Varshavsky | 435/6 |
| 4,603,112 A | 7/1986 | Paoletti et al. | 435/235.1 |
| 4,722,848 A | 2/1988 | Paoletti et al. | 424/199.1 |
| 4,769,330 A | 9/1988 | Paoletti et al. | 435/436 |
| 4,778,759 A | 10/1988 | Szalay et al. | 435/477 |
| 5,110,587 A | 5/1992 | Paoletti et al. | 435/235.1 |
| 5,155,020 A | 10/1992 | Paoletti | 435/69.1 |
| 5,221,623 A | 6/1993 | Legocki et al. | 435/252.3 |
| 5,283,187 A | 2/1994 | Aebischer et al. | 435/182 |
| 5,300,436 A | 4/1994 | Goldstein et al. | 435/190 |
| 5,364,773 A | 11/1994 | Paoletti et al. | 435/69.1 |
| 5,368,855 A | 11/1994 | Boyle et al. | 435/320.1 |
| 5,378,457 A | 1/1995 | Paoletti et al. | 424/205.1 |
| 5,550,050 A | 8/1996 | Holland et al. | 435/382 |
| 5,639,275 A | 6/1997 | Baetge et al. | 604/891.1 |
| 5,646,298 A | 7/1997 | Powell et al. | 548/427 |
| 5,650,135 A | 7/1997 | Contag et al. | 424/9.1 |
| 5,650,148 A | 7/1997 | Gage et al. | 424/93.2 |
| 5,653,975 A | 8/1997 | Baetge et al. | 424/93.1 |
| 5,656,481 A | 8/1997 | Baetge et al. | 435/325 |
| 5,676,943 A | 10/1997 | Baetge et al. | 424/93.21 |
| 5,693,533 A | 12/1997 | Raney et al. | 435/366 |
| 5,704,910 A | 1/1998 | Humes | 604/502 |
| 5,710,137 A | 1/1998 | Fisher | 514/44 |
| 5,718,902 A | 2/1998 | Yilma et al. | 424/211.1 |
| 5,750,103 A | 5/1998 | Cherksey | 424/93.21 |
| 5,756,455 A | 5/1998 | Kinzler et al. | 514/12 |
| 5,762,959 A | 6/1998 | Soon-Shiong et al. | 424/451 |
| 5,795,790 A | 8/1998 | Schinstine et al. | 435/382 |
| 5,798,113 A | 8/1998 | Dionne et al. | 424/422 |
| 5,800,828 A | 9/1998 | Dionne et al. | 424/422 |
| 5,800,829 A | 9/1998 | Dionne et al. | 424/422 |
| 5,830,702 A | 11/1998 | Portnoy et al. | 435/69.3 |
| 5,833,975 A | 11/1998 | Paoletti et al. | 424/93.2 |
| 5,833,979 A | 11/1998 | Schinstine et al. | 424/93.21 |
| 5,834,001 A | 11/1998 | Dionne et al. | 424/422 |
| 5,837,234 A | 11/1998 | Gentile et al. | 424/93.7 |
| 5,840,576 A | 11/1998 | Schinstine et al. | 435/325 |
| 5,842,431 A | 12/1998 | Wu | 112/232 |
| 5,853,385 A | 12/1998 | Emerich et al. | 604/500 |
| 5,853,717 A | 12/1998 | Schinstine et al. | 424/93.21 |
| 5,861,290 A | 1/1999 | Goldsmith et al. | 435/456 |
| 5,866,131 A | 2/1999 | Ramshaw et al. | 424/186.1 |
| 5,976,796 A | 11/1999 | Szalay et al. | 435/6 |
| 6,007,806 A | 12/1999 | Lathe et al. | 424/93.2 |
| 6,025,155 A | 2/2000 | Hadlaczky et al. | 435/69.1 |
| 6,045,802 A | 4/2000 | Schlom et al. | 424/199.1 |
| 6,077,697 A | 6/2000 | Hadlaczky et al. | 435/172.3 |
| 6,080,849 A | 6/2000 | Bermudes et al. | 536/23.7 |
| 6,093,700 A | 7/2000 | Mastrangelo et al. | 514/44 |
| 6,099,848 A | 8/2000 | Frankel et al. | 424/246.1 |
| 6,150,170 A | 11/2000 | Powell et al. | 435/455 |

(Continued)

FOREIGN PATENT DOCUMENTS

AU    709336    4/1995
EP    0037441   10/1981

(Continued)

OTHER PUBLICATIONS

Xiong et al., 2007, Cancer Biology Therapy, vol. 6, No. 7, p. 1067-1073.*

(Continued)

*Primary Examiner* — Shin-Lin Chen
(74) *Attorney, Agent, or Firm* — McKenna Long & Aldridge LLP; Stephanie Seidman

(57) ABSTRACT

Provided are diagnostic and pharmaceutical compositions containing a microorganism or a cell containing a DNA molecule encoding a detectable protein or a protein that a detectable signal, such as a luminescent or fluorescent protein. Methods of tumor targeting and tumor imaging using the microorganisms and cells are provided. Also provided are therapeutic methods in which the microorganisms and cells, which can encoded a therapeutic protein, such as a cytotoxic or cytostatic protein, are administered.

13 Claims, 12 Drawing Sheets

(56) References Cited

U.S. PATENT DOCUMENTS

| | | | |
|---|---|---|---|
| 6,190,657 B1 | 2/2001 | Pawelek et al. | 424/93.1 |
| 6,217,847 B1 | 4/2001 | Contag et al. | 424/9.1 |
| 6,232,523 B1 | 5/2001 | Tan et al. | 800/10 |
| 6,235,967 B1 | 5/2001 | Tan et al. | 800/10 |
| 6,235,968 B1 | 5/2001 | Tan et al. | 800/10 |
| 6,251,384 B1 | 6/2001 | Tan et al. | 424/93.21 |
| 6,265,189 B1 | 7/2001 | Paoletti et al. | 435/70.1 |
| 6,265,557 B1 | 7/2001 | Diamond et al. | 536/23.1 |
| 6,359,189 B1 | 3/2002 | Fleischmann | 602/41 |
| 6,416,754 B1 | 7/2002 | Brown et al. | 424/93.21 |
| 6,428,968 B1 | 8/2002 | Molnar-Kimber et al. | 435/7.23 |
| 6,448,073 B1 | 9/2002 | Jager et al. | 435/320.1 |
| 6,455,673 B1 | 9/2002 | Collier | 530/350 |
| 6,491,905 B1 | 12/2002 | Sorscher et al. | 435/325 |
| 6,503,703 B1 | 1/2003 | Palese et al. | 435/5 |
| 6,511,967 B1 | 1/2003 | Weissleder et al. | 514/44 |
| 6,537,594 B1 | 3/2003 | Paoletti et al. | 424/93.2 |
| 6,548,068 B1 | 4/2003 | Schlom et al. | 424/199.1 |
| 6,589,531 B1 | 7/2003 | Andino-Pavlovsky et al. | 424/199.1 |
| 6,596,279 B1 | 7/2003 | Paoletti et al. | 424/199.1 |
| 6,627,190 B2 | 9/2003 | Wold et al. | 424/93.2 |
| 6,649,143 B1 | 11/2003 | Contag et al. | 424/9.1 |
| 6,649,159 B2 | 11/2003 | Yang et al. | 424/93.21 |
| 6,652,849 B2 | 11/2003 | Brown et al. | 424/93.2 |
| 6,685,935 B1 | 2/2004 | Pawelek et al. | 424/93.2 |
| 6,713,293 B1 | 3/2004 | Grummt et al. | 435/182 |
| 6,743,967 B2 | 6/2004 | Hadlaczky et al. | 800/25 |
| 6,759,038 B2 | 7/2004 | Tan et al. | 424/93.21 |
| 6,884,414 B1 | 4/2005 | Palese et al. | 424/93.2 |
| 6,916,462 B2 | 7/2005 | Contag et al. | 424/9.6 |
| 6,984,374 B2 | 1/2006 | Szalay et al. | 424/9.1 |
| 7,045,313 B1 | 5/2006 | Moss et al. | 435/69.1 |
| 7,118,740 B1 | 10/2006 | Russell et al. | 424/93.6 |
| 7,588,767 B2 | 9/2009 | Szalay et al. | 424/199.1 |
| 7,588,771 B2 | 9/2009 | Szalay et al. | 424/232.1 |
| 7,662,398 B2 | 2/2010 | Szalay et al. | 424/232.1 |
| 7,754,221 B2 | 7/2010 | Szalay et al. | 424/199.1 |
| 8,137,904 B2 | 3/2012 | Szalay et al. | 435/4 |
| 8,221,769 B2 | 7/2012 | Szalay et al. | 424/232.1 |
| 8,323,959 B2 | 12/2012 | Szalay et al. | 435/320.1 |
| 8,357,486 B2 | 1/2013 | Stritzker et al. | 435/4 |
| 2001/0008025 A1 | 7/2001 | Hadlaczky et al. | 800/8 |
| 2001/0029023 A1 | 10/2001 | Szalay et al. | 435/7.1 |
| 2002/0054865 A1 | 5/2002 | Fujimori et al. | 424/93.21 |
| 2002/0160410 A1 | 10/2002 | Hadlaczky et al. | 435/6 |
| 2002/0160970 A1 | 10/2002 | Hadlaczky et al. | 514/44 |
| 2003/0009015 A1 | 1/2003 | Ulrich et al. | 536/23.1 |
| 2003/0021768 A1 | 1/2003 | Shen et al. | 424/93.2 |
| 2003/0031628 A1 | 2/2003 | Zhao et al. | 424/9.6 |
| 2003/0031681 A1 | 2/2003 | Mc Cart et al. | 424/186.1 |
| 2003/0033617 A1 | 2/2003 | Hadlaczky et al. | 800/6 |
| 2003/0044384 A1 | 3/2003 | Roberts et al. | 424/93.2 |
| 2003/0059400 A1 | 3/2003 | Szalay | 424/93.2 |
| 2003/0083293 A1 | 5/2003 | Hadlaczky et al. | 514/44 |
| 2003/0086906 A1 | 5/2003 | Mastrangelo et al. | 424/93.2 |
| 2003/0101480 A1 | 5/2003 | Hadlaczky et al. | 800/278 |
| 2003/0133949 A1 | 7/2003 | Szalay et al. | 424/200.1 |
| 2003/0161788 A1 | 8/2003 | Zhao et al. | 424/9.6 |
| 2003/0165465 A1 | 9/2003 | Roberts et al. | 424/93.2 |
| 2003/0165477 A1 | 9/2003 | Balloul et al. | 424/93.21 |
| 2003/0198627 A1 | 10/2003 | Arts et al. | 424/93.21 |
| 2003/0213007 A1 | 11/2003 | Slattery et al. | 800/15 |
| 2003/0228261 A1 | 12/2003 | Szalay et al. | 424/9.34 |
| 2003/0228330 A1 | 12/2003 | Falkner et al. | 424/232.1 |
| 2004/0076622 A1 | 4/2004 | Studeny et al. | 424/93.21 |
| 2004/0091995 A1 | 5/2004 | Schlom et al. | 435/235.1 |
| 2004/0143861 A1 | 7/2004 | Hadlaczky et al. | 800/14 |
| 2004/0213741 A1 | 10/2004 | Szalay et al. | 424/9.6 |
| 2004/0234455 A1 | 11/2004 | Szalay et al. | 424/9.6 |
| 2005/0025745 A1 | 2/2005 | Fujimori | 424/93.2 |
| 2005/0025747 A1 | 2/2005 | Laidlaw et al. | 424/93.2 |
| 2005/0031643 A1 | 2/2005 | Szalay et al. | 424/199.1 |
| 2005/0063993 A1 | 3/2005 | Schlom et al. | 424/199.1 |
| 2005/0069491 A1 | 3/2005 | Szalay et al. | 424/1.11 |
| 2005/0249670 A1 | 11/2005 | Szalay et al. | 424/9.32 |
| 2006/0051370 A1 | 3/2006 | Szalay et al. | 424/199.1 |
| 2006/0099224 A1 | 5/2006 | Kirn | 424/199.1 |
| 2007/0025981 A1 | 2/2007 | Szalay et al. | 424/130.1 |
| 2007/0202572 A1 | 8/2007 | Szalay et al. | 435/69.1 |
| 2007/0212727 A1 | 9/2007 | Szalay et al. | 435/6 |
| 2008/0193373 A1 | 8/2008 | Stritzker et al. | 424/1.17 |
| 2009/0053244 A1 | 2/2009 | Chen et al. | 435/174.1 |
| 2009/0081639 A1 | 3/2009 | Hill | 435/5 |
| 2009/0098529 A1 | 4/2009 | Chen et al. | 435/5 |
| 2009/0117034 A1 | 5/2009 | Chen et al. | 424/1.17 |
| 2009/0117048 A1 | 5/2009 | Szalay et al. | 424/9.3 |
| 2009/0117049 A1 | 5/2009 | Szalay et al. | 424/9.3 |
| 2009/0123382 A1 | 5/2009 | Szalay et al. | 424/9.6 |
| 2009/0136917 A1 | 5/2009 | Szalay et al. | 435/5 |
| 2009/0155287 A1 | 6/2009 | Chen et al. | 424/158.1 |
| 2009/0162288 A1 | 6/2009 | Chen et al. | 424/9.3 |
| 2009/0180955 A1 | 7/2009 | Stritzker et al. | 424/1.73 |
| 2009/0180987 A1 | 7/2009 | Stritzker et al. | 424/93.2 |
| 2009/0311664 A1 | 12/2009 | Fong et al. | 435/5 |
| 2010/0008946 A1 | 1/2010 | Szalay et al. | 424/199.1 |
| 2010/0062016 A1 | 3/2010 | Szalay et al. | 424/199.1 |
| 2010/0196325 A1 | 8/2010 | Szalay et al. | 424/93.6 |
| 2010/0233078 A1 | 9/2010 | Szalay et al. | 424/1.17 |
| 2011/0064650 A1 | 3/2011 | Szalay | 424/1.11 |
| 2012/0244068 A1 | 9/2012 | Chen et al. | 424/1.11 |
| 2012/0276010 A1 | 11/2012 | Szalay et al. | 424/9.1 |
| 2012/0308484 A1 | 12/2012 | Szalay et al. | 424/9.3 |

FOREIGN PATENT DOCUMENTS

| | | |
|---|---|---|
| EP | 0861093 | 9/1998 |
| EP | 1020197 | 7/2000 |
| EP | 1146125 | 10/2001 |
| EP | 1281772 | 2/2003 |
| EP | 1281777 | 2/2003 |
| EP | 1281767 | 5/2003 |
| EP | 1369491 | 12/2003 |
| EP | 1 414 994 | 5/2004 |
| EP | 1254250 | 3/2005 |
| EP | 1512746 | 3/2005 |
| EP | 1526185 | 4/2005 |
| WO | WO 88/00617 | 1/1988 |
| WO | WO 90/13658 | 11/1990 |
| WO | WO 91/07989 | 6/1991 |
| WO | WO 92/22327 | 12/1992 |
| WO | WO 95/31105 | 11/1995 |
| WO | WO 96/11279 | 4/1996 |
| WO | WO 96/40238 | 12/1996 |
| WO | WO 97/18841 | 5/1997 |
| WO | WO 97/40183 | 10/1997 |
| WO | WO 98/14605 | 4/1998 |
| WO | WO 99/13053 | 3/1999 |
| WO | WO 99/18799 | 4/1999 |
| WO | WO 00/47237 | 8/2000 |
| WO | WO 00/62735 | 10/2000 |
| WO | WO 00/73479 | 12/2000 |
| WO | WO 01/05229 | 1/2001 |
| WO | WO 01/12234 | 2/2001 |
| WO | WO 01/14579 | 3/2001 |
| WO | WO 01/18195 | 3/2001 |
| WO | WO 01/20989 | 3/2001 |
| WO | WO 01/24637 | 4/2001 |
| WO | WO 01/25399 | 4/2001 |
| WO | WO 01/55444 | 8/2001 |
| WO | WO 03/006069 | 1/2003 |
| WO | WO 03/014380 | 2/2003 |
| WO | WO 03/045153 | 6/2003 |
| WO | WO 03/049117 | 6/2003 |
| WO | WO 03/057007 | 7/2003 |
| WO | WO 03/063593 | 8/2003 |
| WO | WO 03/092600 | 11/2003 |
| WO | WO 03/102168 | 12/2003 |
| WO | WO 03/102169 | 12/2003 |
| WO | WO 03/104485 | 12/2003 |
| WO | WO 2004/030631 | 4/2004 |
| WO | WO 2004/044175 | 5/2004 |
| WO | WO 2005/047458 | 5/2005 |
| WO | WO 2005/057488 | 6/2005 |

(56) References Cited

FOREIGN PATENT DOCUMENTS

| | | |
|---|---|---|
| WO | WO 2005/072622 | 8/2005 |
| WO | WO 2007/075879 | 7/2007 |
| WO | WO 2009/054996 | 4/2009 |
| WO | WO 2008/100292 | 5/2009 |
| WO | WO 2009/139921 | 11/2009 |

OTHER PUBLICATIONS

Smallwood et al., 2002 Virology, vol. 304, p. 135-145.*
Chattopadhyay et al., 2004, Virus Research, vol. 99, p. 139-145.*
Sui et al., 2004, Clinical Cancer Research, vol. 10, p. 4848-4857.*
Martinez et al., 2006, The Journal of Infectious Diseases, vol. 194, p. 261-266.*
Okuse et al., 2005, Antiviral Research, vol. 65, p. 23-34.*
Xiong et al., 2007, Cancer Biology Therapy, vol. 6, No. 7, p. 1067-1073.*
Everts et al., 2005, Cancer Gene Therapy, vol. 12, p. 141-161.*
Buller et al., 1985, Nature, vol. 317, p. 813-815.*
Amato et al., "Luminous with promise," Chem. Eng. News. 84(49):69-73 (2006).
Chen et al., "Real-time monitoring of vaccinia virus infection in cultured cells and in living mice using light-emitting proteins" Proceedings of the 14th International Symposium on Bioluminescence & Chemiluminescence: Chemistry, Biology and Applications, World Scientific: Singapore: 181-184 (2007).
Chkheidze et al., "Identification of DNA binding proteins in vaccinia virus by DNA-protein crosslinking," FEBS 336(2):340-342 (1993).
Conry et al., "Phase I trial of a recombinant vaccinia virus encoding carcinoembryonic antigen in metastatic adenocarcinoma: comparison of intradermal versus subcutaneous administration," Clin Cancer Res 5:2330-2337 (1999).
Davis et al., "Oncolytic virotherapy for cancer treatment: challenges and solutions," J. Gene Med. 7(11):1380-1389 (2005).
Earl et al., "T-lymphocyte priming and protection against Friend leukemia by vaccinia-retrovirus env gene recombinant," Science 234:728-831 (1986).
Gherardi et al., "Recombinant poxviruses as mucosal vaccine vectors," J Gen Viral 86:2925-2936 (2005).
Giavedoni et al., "Vaccinia virus recombinants expressing chimeric proteins of human immunodeficiency virus and gamma-interferon are attenuated for nude mice," Proc. Natl. Acad. Sci. 89:3409-3413 (1992).
Haga et al., "Evasion of innate immunity by vaccinia virus," Parasitology 130:S11-S25 (2005).
Hauser et al., "Poxvirus as a vector to transduce human dendritic cells for immunotherapy: abortive infection but reduced APC function," Gene Ther. 7(18):1575-1583 (2000).
Heise et al., "Efficacy of a replication-competent adenovirus (ONYX-015) following intratumoral injection: intratumoral spread and distribution effects," Cancer Gene Ther. 6(6):499-504 (1999).
Hodge et al., "Induction of antitumor immunity by recombinant vaccinia viruses expressing B7-1 or B7-2 costimulatory molecules," Cancer Res. 54(21):5552-5555 (1994).
Ikeda et al., "Oncolytic virus therapy of multiple tumors in the brain requires suppression of innate and elicited antiviral responses," Nat Med. 5(8):881-887 (1999).
Jia et al., "Viral vectors for cancer gene therapy: viral dissemination and tumor targeting," Curr. Gene Ther. 5:133-142 (2005).
Kass et al, "Induction of protective host immunity to carcinoembryonic antigen (CEA), a selfantigen in CEA transgenic mice, by immunizing with a recombinant vaccinia-CEA virus," Cancer Research 59:676-683 (1999).
Kaufman et al., "Insertion of interleukin-2 (IL-2) and interleukin-12 (IL-12) genes into vaccinia virus results in effective anti-tumor responses without toxicity," Vaccine 20:1862-1869 (2002).
Kirn et al., "Replication-selective virotherapy for cancer: biological principles, risk management and future directions," Nat. Med. 7:781-787 (2001).

Liu Ta-Chiang, et al. "Clinical trial results with oncolytic virotherapy: a century of promise, a decade of progress," Nat Clin Pract Oncol 4:101-16 (2006).
Mastrangelo et al., "Intratumoral recombinant GM-CSF-encoding virus as gene therapy in patients with cutaneous melanoma," Cancer Gene Ther. 6(5):409-422 (1998).
Okada et al., "Sensitization of human tumor cells to homologous complement by vaccinia virus treatment," Cancer Immunol Immunother 25(1):7-9 (1987).
Paoletti et al., "Applications of pox virus vectors to vaccination: an update," Proc. Natl. Acad. Sci. 93:11349-11353 (1996).
Parato et al., "Recent progress in the battle between oncolytic viruses and tumours," Nature Rev. 5:965-976 (2005).
Peplinski et al., "Prevention of murine breast cancer by vaccination with tumor cells modified by cytokine-producing recombinant vaccinia viruses," Annals Surg. Oncol. 3(1):15-23 (1996).
Qin et al., "Construction of recombinant vaccinia virus expressing GM-CSF and its use as a tumor vaccine," Gene Ther. 3(1):59-66 (1996).
Raab et al., "Four-color labeling of cell culture and tumors of live mice upon infection with: GFP-Ruc and RFP-CBG99 expressing Vaccinia virus strains" Proceedings of the 14th International Symposium on Bioluminescence & Chemiluminescence: Chemistry, Biology and Applications, World Scientific: Singapore, 197-200 (2007).
Ramirez et al., "Biology of attenuated modified vaccinia virus Ankara recombinant vector in mice: Virus fate and activation of B- and T-Cell immune responses in comparsion with the Western Reserve Strain and advantages as a vaccine," J. Virol. 74(2):923-933 (2000).
Roenigk et al., "Immunotherapy of malignant melanoma with vaccinia virus," Arch Dermatol 109:668-673 (1977).
Shen et al., "Fighting cancer with vaccinia virus: Teaching new tricks to an old dog," Mol. Therapy 11(2):180-195 (2005).
Shida et al., "Effects and virulences of recombinant vaccinia viruses derived from attenuated strains that express the human T-cell leukemia virus type I envelope gene," J. Virol. 62(12):4474-4480 (1988).
Smith et al., "Host range selection of vaccinia recombinants containing insertions of foreign genes into non-coding sequences," Vaccine 11(1):43-53 (1993).
Smith et al., "Immune response to poxvirus infections in various animals," Crit. Rev. Microbiol. 28(3):149-185 (2002).
Sroller et al., "Effect of 3-beta-hydroxysteroid dehydrogenase gene deletion on virulence and immunogenicity of different vaccinia viruses and their recombinants," Arch. Virol. 143:1311-1320 (1998).
Steele et al., "Recent developments in the virus therapy of cancer," Proc Soc Exp Biol Med. 223:118-127 (2000).
Taylor et al., "Comparison of the virulence of wild-type thymidine kinase (tk)-deficient and tk+ phenotypes of vaccinia virus recombinants after intranasal inoculation of mice," J. Gen. Virol. 72 (Pt 1):125-130 (1991).
Thorne et al., "The use of oncolytic vaccinia viruses in the treatment of cancer: a new role for an old ally?" Curr. Gene Ther. 5:429-443 (2005).
Woo et al., "Advances in oncolytic viral therapy," Curr. Opin. Investig. Drugs 7:549-559 (2006).
Zhang et al., "Eradication of solid human tumors in nude mice with an intravenously injected light emitting oncolytic vaccinia virus," Cancer Res. 67(20):10038-10046 (2007).
"A New Way to Kill Cancer: SLU Research Shows Viruses can destroy lung, colon tumors," Science Daily: Your link to the latest research news http://www.sciencedaily.com/releases/2004/05/040517071951.htm (accessed on May 17, 2004).
"Generation of Recombinant Vaccinia Viruses," Unit 16.17 in Short Protocols in Molecular Biology $2^{nd}$ edition: a compendium of Methods from Current Protocols in Molecular Biology, Green Publishing and Wiley-Interscience Supplement 15:16.71-16.82 (1992).
"WHO Collaborating Centre for Orthopoxvirus Diagnosis and Repository for Variola Virus Strains and DNA," VECTOR: Ministry of Public Health and Social Development of Russian Federation, State Research Center of Virology and Biotechnology http://www.vector.nsc.ru/DesktopDefault.aspx?lcid=9&tabid=294&tabindex=1 (accessed on Sep. 12, 2005).

(56) References Cited

OTHER PUBLICATIONS

Aboody et al., "Neural stem cells display extensive tropism for pathology in adult brain: evidence from intracranial gliomas," Proc Natl Acad Sci U S A. 97(23):12846-12851 (2000).
Adonai et al., "Ex vivo cell labeling with $^{64}$Cu-pyruvaldehyde-bis ($N^4$-methylthiosemicarbazone) for imaging cell trafficking in mice with positron-emission tomography," Proc. Natl. Acad. Sci. USA 99: 3030-3035 (2002).
Advani et al., "Replication-competent, nonneuroinvasive genetically engineered herpes virus is highly effective in the treatment of therapy-resistant experimental human tumors," Cancer Research 59: 2055-2058 (1999).
Advisory Committee on Immunization Practices (ACIP), "Smallpox vaccination and adverse reactions: guidance for clinicians," Morbidity and Mortality Weekly Report 52(RR-4): 1-29 (Feb. 21, 2003).
Advisory Committee on Immunization Practices (ACIP), Vaccinia (smallpox) vaccine: recommendations of the Advisory Committee on Immunization Practices (ACIP), MMWR, 50(RR-10): 1-26 & ce1-ce7 (Jun. 22, 2001).
Aebischer et al., "Long-term cross-species brain transplantation of a polymer-encapsulated dopamine-secreting cell line," Experimental Neurology 111:269-275 (1991).
Aebischer et al.,"Functional Recovery in Hemiparkinsonian Primates Transplanted with Polymer-Encapsulated PC12 Cells," Experimental Neurology 126:151-158 (1994).
Aguilar, O., et al., "The nitEN genes participating in FeMo cofactor biosynthesis and genes encoding dinitrogenase are part of the same operon in *Bradyrhizobium* species," Mol Gen Genet. 224(3):413-20 (1990).
Aksac S., "[Antibody formation against *Agrobacterium tumefaciens* in patients with various cancers]," Turk Hij Tecr Biyol Derg. 34(1-2):48-51 (1974) [Article in Italian].
Alcamí, A. et al., "Vaccinia virus strains Lister, USSR and Evans express soluble and cell-surface tumour necrosis factor receptors," J. Gen. Virol. 80: 949-959 (1999).
Altenbrunn et al., "Scintographic Tumor Localization in Mice with Radioiodinated Anti-*Clostridium* Antibodies," Int. J. Nucl. Med. Biol. 8(1): 90-93 (1981).
Altschul et al., "Basic local alignment search tool," J Molec Biol 215:403-410 (1990).
Al'tshtein et al., "[Isolation of a recombinant vaccinia virus based on the LIVP strain inducing the surface antigen of the hepatitis B virus]," Dokl Akad Nauk SSSR. 285(3):696-9 (1985) [Article in Russian].
Anaissie et al., "*Pseudomonas putida*. Newly recognized pathogen in patients with cancer," Am J Med. 82(6):1191-1194 (1987).
Anand, A and A.E. Glatt, "Clostridium difficile infection associated with antineoplastic chemotherapy: a review," Clin Infect Dis. 17(1):109-13 (1993).
Ando, N. and M. Matumoto, "Unmasking of growth of dermovaccinia strain dairen I in L cells by acid treatment of cells after virus adsorption," Japan. J. Microbiol. 14(3): 181-186 (1979).
Antoine et al., "The complete genomic sequence of the modified vaccinia Ankara strain: comparison with other orthopoxviruses," Virology 244: 365-396 (1998).
Antoine, G. et al., "Characterization of the vaccinia MVA hemagglutinin gene locus and its evaluation as an insertion site for foreign genes", Gene, 177: 43-46 (1996).
Arab et al., "Verotoxin induces apoptosis and the complete, rapid, long-term elimination of human astrocytoma xenografts in nude mice," Oncol Res. 11(1):33-9 (1999).
Arakawa et al., "Clinical trial of attenuated vaccinia virus AS strain in the treatment of advanced adenocarcinoma. Report on two cases," J Cancer Res Clin Oncol. 113(1):95-8 (1987).
ATCC Accession No. 11842.
ATCC Accession No. 11863.
ATCC Accession No. 13124.
ATCC Accession No. 15696.
ATCC Accession No. 15697.
ATCC Accession No. 15707.
ATCC Accession No. 15955.
ATCC Accession No. 17583.
ATCC Accession No. 17836.
ATCC Accession No. 19401.
ATCC Accession No. 19402.
ATCC Accession No. 19404.
ATCC Accession No. 25527.
ATCC Accession No. 25752.
ATCC Accession No. 25923.
ATCC Accession No. 27337.
ATCC Accession No. 27555.
ATCC Accession No. 29212.
ATCC Accession No. 35782.
ATCC Accession No. 3624.
ATCC Accession No. 37253.
ATCC Accession No. 393.
ATCC Accession No. 43142.
ATCC Accession No. 47054.
ATCC Accession No. 51299.
ATCC Accession No. 59324.
ATCC Accession No. 59325.
ATCC Accession No. 700057.
ATCC Accession No. 824.
ATCC Accession No. 9338.
ATCC Accession No. 9714.
ATCC Accession No. BAA-250D.
ATCC Accession No. CCL-70.
ATCC Accession Nos. CCL-121.
ATCC Accession Nos. CRL-12011.
ATCC Accession Nos. CRL-12012.
ATCC catalog No. 700294.
ATCC No. CCL-107.
ATCC No. CRL-6475.
ATCC under Accession No. VR-1549.
Azmi et al., "In situ localization of endogenous cytokinins during shooty tumor development on *Eucalyptus globulus* Labill," Planta 213(1):29-36 (2001).
Baeksgaard, L. and J.B. Sorensen, "Acute tumor lyssi syndrome in solid tumors—a case report and review of the literature", Cancer Chemother. Pharmacol., 51: 187-192 (2003).
Baker, R.O. et al., "Potential antiviral tehrapeutics for smallpox, monkeypox, and other orthopoxvirus infections", Antiviral Research, 57: 13-23 (2003).
Baker, S.J. and E.P. Reddy, "Transducers of life and death: TNF receptor superfamily and associated proteins," Oncogene 12(1):1-9 (1996).
Balkwill, F., "Chemokine biology in cancer", Seminars in Immunol. 15: 49-55 (2003).
Banerjee et al., "*Bacillus* infections in patientfs with cancer," Arch Intern Med. 148(8):1769-1774 (1988).
Barrett et al., "Yellow ever vaccines," Biologicals 25:17-25 (1997).
Bauerschnitz et al., "Treatment of ovarian cancer with a tropism modified oncolytic adenovirus," Cancer Research 62: 1266-1270 (2002).
Baxby, D., "Poxviruses", Chapter 15 in Principles and Practice of Clinical Virology, Zuckerman, A.J. et al.(eds.), John Wiley & Sons Ltd., pp. 451-465 (2000).
Beebe, J. and E. Koneman, "Recovery of Uncommon Bacteria from Blood: Association with Neoplastic Disease," Clin. Microbiol. Rev. 8(3): 336-356 (1995).
Beerntsen, B., et al., "Genetics of mosquito vector competenc," Microbiol. Mol. Biol. Rev. 64(1): 115-137 (2000).
Belas et al., "Bacterial bioluminescence: isolation and expression of the luciferase genes from *Vibrio harveyi*," Science 218: 791-793 (1982).
Bell, J., et al., "Getting oncolytic virus therapies off the ground," Cancer Cell, 4: 7-11 (2003).
Bendig, M., "The production of foreigh proteins in mammalian cells," Genetic Engineering 7:91-127 (1988).
Benes et al., "M13 and pUC vectors with new unique restriction sites for cloning," Gene 130: 151-152 (1993).
Bennett et al., "Positron emission tomography imaging for herpes virus infection: imgplications for oncolytic viral treatments of cancer," Nature Med 7(7): 859-863 (2001).

(56) References Cited

OTHER PUBLICATIONS

Bentires-Alj et al., "Cytosine deaminase suicide gene therapy for peritoneal carcinomatosis," Cancer Gene Ther. 7(1):20-26 (2000).
Berger, F. and S.Gambhir, "Recent advances in imaging endogenous or transferred gene expression utilizing radionuclide technologies in living subjects," Breast Cancer Research 3: 28-35 (2001).
Bergsland, E. and A. Venook, "Shedding old paradigms: developing viruses to treat cancer," J. Clin. Oncol. 20(9): 2220-2222 (2002).
Bermudes et al., "Live bacteria as anticancer agents and tumor-selective protein delivery vectors," Current Opinion in Drug Discovery & Development 5(2):194-199 (2002).
Bermudes et al., "Tumor-targeted *Salmonella*: highly selective delivery vectors," Adv Exp Med Biol. 465:57-63 (2000).
Bernards et al., "Effective tumor immunotherapy directed against an oncogene-encoded produt using a vaccinia virus vector," Proc. Natl. Acad. Sci. USA 84: 6854-6858 (1987).
Beshara et al., "Kinetic analysis of $^{52}$Fe-labelled iron(III) hydroxide-sucrose complex following blous administration using positron emission tomography," Br. J. Haematol. 104: 288-295 (1999).
Beshara et al., "Pharmacokinetics and red cell utilization of iron(III) hydroxide-sucrose complex in anaemic patients: a study using positron emission tomography," Br. J. Haematol. 104: 296-302 (1999).
Best et al., "Baboon/human homologies examined by spectral karyotyping (SKY): a visual comparison," Cytogenet Cell Genet. 82(1-2):83-87 (1998).
Beyer et al., "Oncoretrovirus and lentivirus vectors pseudotyped with lymphocytic choriomeningitis virus glycoprotein: generation, concentration, and broad host range," J Virol. 76(3):1488-95 (2002).
Bickels, J. et al., "Coley's toxin: historical perspective," Isr. Med. Assoc. J., 4(6): 471-472 (2002).
Biffi et al., "Antiproliferative effect of fermented milk on the growth of a human breast cancer cell line," Nutr Cancer. 28(1):93-99 (1997).
Bisno et al., "Streptococcal infections of skin and soft tissues," N. Engl. J. Med. 334(4): 240-245 (1996).
Blakemore, "Magnetotactic Bacteria," Annu. Rev. Microbiol. 36: 217-238 (1982).
Blanchard, T.J. et al., "Modified vaccinia virus Ankara undergoes limited replication in human cells and lacks several immunomodulatory proteins: implications for use as a human vaccine," Journal of General Virology 79:1159-1167 (1998).
Blasberg, R. and J. Tjuvajev, "Herpes simplex virus thymidine kinase as a marker/reporter gene for PET imaging of gene therapy," Q J Nucl Med 43(2):163-169 (1999).
Blasco, R. and B. Moss, "Selection of recombinant vaccinia viruses on the basis of plaque formation," Gene 158:157-162 (1995).
Block et al., "Gene therapy of metastatic colon carcinoma: regression of multiple hepatic metastases by adnoviral expression of bacterial cytosine deaminase," Cancer Gene Ther. 7(3):438-445 (2000).
Bodey et al., "Clostridial bacteremia in cancer patients. A 12-year experience," Cancer 67(7):1928-1942 (1991).
Bogdahn et al., "Autocrine Tumor Cell Growth-inhibiting Activities from Human Malignant Melanoma," Cancer Research 49:5358-5363 (1989).
Bogdanov et al., "Antitumor action of glycopeptides from the cell wall of *Lactobacillus bulgaricus*," Bulletin of Experimental Biology and Medicine. 84(12): 1750-1753 (1977); translated from the original Russian article: Byulleten' Éksperimental'noi Biologii I Meditsiny 84(12):709-712 (1977).
Bogdanov et al., "Antitumour glycopeptides from *Lactobacillus bulgaricus* cell wall," FEBS Lett. 57(3):259-261 (1975).
Boland et al., "Adenovirus-mediated Transfer of the Thyroid Sodium/Iodide Symporter Gene into Tumors for a Targeted Radiotherapy," Cancer Research 60: 3484-3492 (2000).
Bonnekoh et al., "Adenoviral-Mediated Herpes Simplex Virus-Thymidine Kinase Gene Transfer in Vivo for Treatment of Experimental Human Melanoma," J .Invest. Dermatol. 106(6):1163-1168 (1996).
Borellini, F. and J.M. Ostrove, "The Transfer of Technology from the Laboratory to the Clinic: In Process Controls and Final Product Testing", Chapter 18 in Gene Therapy Technologies, Applications and Regulations, A. Meager (Ed.), John Wiley & Sons Ltd., pp. 359-373 (1999).
Boulanger, D. et al., "Morphogenesis and release of fowlpox virusm," Journal of General Virology, 81:675-687 (2000).
Bouvier et al., "Functional characterization of the human dopamine D-4.2 receptor using vaccinia virus as an expression system," European Journal of Pharmacology 290(1):11-17 (1995).
Boyd, J., "Facilities for Large-Scale Production of Vectors under GMP Conditions", Chapter 20 in Gene Therapy Technologies, Applications and Regulations, A. Meager (Ed.), pp. 383-400 (1999).
Brain, J.D. et al., "Pulmonary intravascular macrophages: their contribution to the mononuclear phagocyte system in 13 species," Am. J. Physiol., 276(1 pt 1):L146-L154 (1999).
Breman, J. and D. Henderson, "Diagnosis and Management of Smallpox", N. Engl. J. Med. 346(17): 1300-1308 (2002).
Brockstedt et al., "Development of Anti-tumor Immunity against a Non-immunogenic Mammary Carcinoma through in Vivo Somatic GM-CSF, IL-2, and HSVtk Combination Gene Therapy," Mol. Ther. 6(5): 627-636 (2002).
Broder, C. and P. Earl, "Recombinant Vaccinia Viruses," Mol. Biotechnol. 13: 223-245 (1999).
Broder, C. et al., "Expression of foreign genes in cultured human primary macrophages using recombinant vaccinia virus vectors," Gene, 142:167-174 (1994).
Brouqui, P. and D. Raoult, "Endocarditis due to rare and fastidious bacteria," Clinical Microbiology Reviews 14(1):177-207 (2001).
Broyles, S., "Vaccinia virus transcription," Journal of General Virology 84: 2293-2303 (2003).
Brunke M et al., "Luciferase assembly after transport into mammalian microsomes involves molecular chaperones and peptidyl-prolyl cis/trans-isomerases," J Biol Chem. 271(38):23487-23494 (1996).
Calonder et al., "Kinetic modeling of $^{52}$Fe/$^{52m}$Mn-Citrate at the Blood-Brain Barrier by Positron Emission Tomography," J. Neurochem. 73:2047-2055 (1999).
Carrillo and Lipman et al., "The Multiple Sequence Alignment Problem in Biology," SIAM J Applied Math 48:1073-1082 (1988).
Carroll, S. and R. Collier, "Active site of *Pseudomonas aeruginosa* Exotoxin A," J. Biol. Chem. 262:8707-8711 (1987).
Carter, G. et al., "Vaccinia virus cores are transported on microtubules", Journal of General Virology, 84: 2443-2458 (2003).
Cavanagh, L. and U. von Andrian, "Travellers in many guises: The origins and destinations of dendritic cells," Immunology and Cell Biology 80:448-462 (2002).
Certified English translation of abstract for Aksac S., "[Antibody formation against *Agrobacterium tumefaciens* in patients with various cancers]," Turk Hij Tecr Biyol Derg. 34(1-2):48-51 (1974) [Article in Italian].
Certified English translation of journal article for Al'tshtein [Altshteyn] et al., "[Isolation of a recombinant vaccinia virus based on the LIVP strain inducing the surface antigen of the hepatitis B virus]," Dokl Akad Nauk SSSR. 285(3):696-9 (1985) [Article in Russian].
Certified English translation of Timiryasova et al., "Analysis of Reporter Gene Expression in Various Regions of the Genome of the Vaccinia Virus," Molecular Biology 27(2): 392-401 (1993).
Chakrabarti et al., "Compact, Synthetic, Vaccinia Virus Early/Late Promoter for Protein Expression," BioTechniques 23(6):1094-1097 (1997).
Chakrabarti et al., "Vaccinia virus expression vector: coexpression of β-galactosidase provides visual screening of recombinant virus plaques," Mol. Cell Biol. 5:3403-3409 (1985).
Chalfie et al., "Green Fluorescent Protein as a Marker for Gene Expression," Science 263:802-805 (1994).
Chaloupka et al.,"Comparative Analysis of Six European Influenza Vaccines," European J. Microbiology Infectious Disease 15(2):121-127 (1996).
Chaloupka, I., et al., "Comparative analysis of six european influenza vaccines," European Journal of Microbiology and Infectious Disease, 15(2):121-127, (1996).
Chamberlain et al., "Costimulation enhances the active immunotherapy effect of recombinant anticancer vaccines," Cancer Res. 56:2832-2836 (1996).

(56) References Cited

OTHER PUBLICATIONS

Chambers, A., et al., "Dissemination and Growth of Cancer Cells in Metastatic Sites," Nat. Rev. Cancer 2:563-572 (2002).
Chambers, A., et al., "Molecular biology of breast cancer metastasis Clinical implications of experimental studies on metastatic inefficiency," Breast Cancer Res. 2:400-407 (2000).
Chang et al., "Differential apoptotic susceptibility to anti-Fas IgM and anticancer drugs in a human endometrial adenocarcinoma cell line HHUA on laminin and type I collagen," Osaka City Med J. 44(2):173-180 (1998).
Chatterjee, B. and C. Chakraborti, "Non-sporing anaerobes in certain surgical group of patients," J Indian Med Assoc. 93(9):333-335, 339 (1995).
Chaudhary et al., "Role of domain II of *Pseudomonas* exotoxin in the secretion of proteins into the periplasm and medium by *Escherichia coli*," Proc. Natl. Acad. Sci. USA 85: 2939-2943 (1988).
Chaudhuri et al., "Light-based imaging of green fluorescent protein-positive ovarian cancer xenografts during therapy," Gynecol. Oncol. 82(3): 581-589 (2001).
Cheadle, E. and A. Jackson, "Bugs as Drugs for Cancer," Immunol. 107: 10-19 (2002).
Chen "Orthopedic applications of gene therapy," J Orthop Sci 6:199-207 (2001).
Chen et al. "Cancer gene therapy by direct tumor injections of a nonviral T7 vector encoding a thymidine kinase gene," Hum Gene Ther. 9(5):729-36 (1998).
Chen et al. "Evaluation of combined vaccinia virus-mediated antitumor gene therapy with p53, IL-2, and IL-12 in a glioma model," Cancer Gene Ther. 7(11):1437-1447 (2000).
Chen et al., "Evaluation of Cytokine Toxicity Induced by Vaccinia Virus-mediated IL-2 and IL-2 Antitumor Immunotherapy," Cytokine 15(61):305-314 (2001).
Chen et al., "Low-dose vaccinia virus-mediated cytokine gene therapy of glioma," J Immunother. 24(1):46-57 (2001).
Chernajovsky et al., "Fighting cancer with oncolytic viruses," BMJ 332(7534):170-172 (2006).
Child et al., "Insertional inactivation of the large subunit of ribonucleotide reductase encoded by vaccinia virus is associated with reduced virulence in vivo," Virology 174:625-629 (1990).
Chiocca, E., "Oncolytic Viruses," Nat. Rev. Cancer, 2(12): 938-950 (2002).
Choi et al., "Efficient secretory production of alkaline phosphatase by high cell density culture of recombinant *Escherichia coli* using the *Bacillus* sp. endoxylanase signal sequence," Appl. Microbiol. Biotechnol. 53:640-645 (2000).
Cichutek, K., "Development and Regulation of Gene Therapy Drugs in Germany", Chapter 17 in Gene Therapy Technologies, Applications and Regulations, A. Meager (Ed.), John Wiley & Sons Ltd. pp. 347-358 (c1999).
Cioffi et al. "A novel endothelial cell-based gene therapy platform for the in vivo delivery of apolipoprotein E," Gene Therapy 6:1153-1159 (1999).
Clairmont et al., "Biodistribution and genetic stability of the novel antitumor agent VNP20009, a genetically modified strain of *Salmonella typhimurium*," J Infect Dis. 181(6):1996-2002 (2000).
Clairmont, C. et al., "Enhanced antitumor activity from tumor-targeting *Salmonella* expressing endostatin," American Association for Cancer Research: 91st Annual Meeting of the AACR, Apr. 1-5, 2000, 41:732 Abstract #4653 (2000).
Cole, A. and T. Ganz, "Human antimicrobial peptides: analysis and application," Biotechniques. 29(4):822-826, 828, 830-831 (2000).
Colinas et al., "A DNA ligase gene in the copenhagen strain of vaccinia virus is nonessential for viral replication and recombination," Virology 179: 267-275 (1990).
Collins, J. and C. Wust, "Suppression of SV40 tumors after immunization with group A *Streptococcus pyogenes* and *Bordetella pertussis*," Cancer Res. 34(5):932-7 (1974).
Compton, J. and A. Szalay, "Insertion of nonhomologous DNA into the yeast genome mediated by homologous recombination with a cotransforming plasmid," Mol Gen Genet. 188(1):44-50 (1982).

Condeelis, J. and J.E. Segall, "Intravital imaging of cell movement in tumours," Nat. Rev. Cancer 3:921-930 (2003).
Contag et al., "Visualizing Gene Expression in Living Mammals Using a Bioluminescent Reporter" Photochemistry and Photobiology 66(4):523-531 (1997).
Contag et al., "Photonic detection of bacterial pathogens in living hosts," Mol. Microbiol. 18: 593-603 (1995).
Coupar, B., et al., "A general method for the construction of recombinant vaccinia viruses expressing multiple foreign genes", Gene, 68: 1-10 (1988).
Coussens, L. and Z. Werb, "Inflammation and cancer," Nature 420:860-867 (2002).
Craperi et al. "Increased bax expression is associated with cell death induced by ganciclovir in a herpes thymidine kinase gene-expressing glioma cell line." Hum Gene Ther. 10(4):679-688 (1999).
Crystal, "Transfer of Genes to Humans: Early Lessons and Obstacles to Success" Science 270:404-410 (1995).
Cseh, S. et al., "Rapid freezing of mouse embryos in ethylene glycol at different preimplantation stages," Acta Veterinaria Hungarica 44(4):457-465 (1996).
Culver et al., "In vivo gene transfer with retroviral vector-producer cells for treatment of experimental brain tumors." Science. 256(5063):1550-1552 (1992).
Cusumano et al., "Synergic activities of streptococcal pyrogenic exotoxin A and lipoteichoic acid in cytokine induction," Microbiologica 23(1): 37-45 (2000).
Dang et al., "Combination bacteriolytic therapy for the treatment of experimental tumors," Proc Natl Acad Sci U S A. 98(26):15155-15160 (2001).
Davis, "The Many Faces of Epidermal Growth Factor Repeats", The New Biologist 2(5):410-419 (1990).
Davis, C. et al., "The role of inflammation in vascular injury and repair", Journal of Thrombosis and Haemostasis, 1: 1699-1709 (2003).
Davison et al., "New vaccinia virus recombination plasmids incorporating a synthetic late promoter for high level expression of foreign proteins," Nucleic Acids Research 18: 4285-4286 (1990).
Davison, A. J. and B. Moss, "Structure of Vaccinia Virus Early Promoters," J. Mol. Biol. 210: 749-769 (1989).
De Clercq, E., "Cidofovir in the therapy and short-term prophylaxis of poxvirus infections", Trends in Pharmacological Sciences, 23(10): 456-458 (2002).
de Lorenzo V., "Isolation and characterization of microcin E492 from *Klebsiella pneumoniae*," Arch Microbiol. 139(1):72-75 (1984).
de Wet et al., "Firefly Luciferase Gene: Structure and Expression in Mammalian Cells," Mol. Cell. Biol. 7: 725-737 (1987).
Demers, G.W. et al., "Pharmacologic Indicators of Antitumor Efficacy for Oncolytic Virotherapy", Cancer Res., 63: 4003-4008 (2003).
Deng et al. "Engineering Ex Vivo-Expanded Marrow Stromal Cells to Secrete Calcitonin Gene-Related Peptide Using Adenoviral Vector," Stem Cells 22:1279-1291 (2004).
Derwent English abstract for Japanese Patent Publication JP 55035004, published Feb. 3, 1987, entitled, "Cellular immuno-potentiator—contg. Vaccinia attenuated virus showing no. infectivity to man or rabbit and has lost humoral immunity," Derwent Accession No. 2512008.
Derwent English abstract for WO 94/10302, published May 11, 1994 entitled: "Vectors inhibiting HIV replication in potential host cells—contg. DNA encoding Pol, Gag, Env, Rev, and/or Tat in antisense direction and further DNA causing spontaneous amplification," Accession Nbr. 1994-152544 [19].
Devereux, J., et al., "A comprehensive set of sequence analysis programs for the VAX," Nucleic Acids Research 12(1): 387-95 (1984).
Diamond, D.C. et al. "Sequence comparison of baboon ABO histo-blood group alleles: lesions found in O alleles differ between human and baboon," Blood Cells Mol Dis. 23(2):242-51 (1997).
Diamond, D.C., et al., "Genotyping the baboon ABO histo-blood group locus by two-color fluorescence SSCP," Biotechniques 27(5):1054, 1056, 1058-59, 1061 (1999).
Dietrich, G. et al., "Delivery of antigen-encoding plasmid DNA into the cytosol of macrophages by attenuated suicide *Listeria monocytogenes*," Nat Biotechnol. 16(2):181-5 (1998).

(56) References Cited

OTHER PUBLICATIONS

Ding et al., "Zinc-dependent dimers observed in crystals of human endostatin," Proc. Natl. Acad. Sci. USA 95:10443-10448 (1998).
Djeha et al., Combined adenovirus-mediated nitroreductase gene delivery and CB1954 treatment: a well-tolerated therapy for established solid tumors. Mol Ther. 3(2):233-240 (2001).
Djeha et al., "Expression of *Escherichia coli* B nitroreductase in established human tumor xenografts in mice results in potent antitumoral and bystander effects upon systemic administration of the prodrug CB1954," Cancer Gene Ther. 7(5):721-731 (2000).
Dobbelstein, M., "Viruses in therapy—royal road or dead end?", Virus Research, 92: 219-221 (2003).
Domi, A. and B. Moss, "Cloning the vaccinia virus genome as a bacterial artificial chromosome in *Escherichia coli* and recovery of infectious virus in mammalian cells", Proc. Natl. Acad. Sci. U.S.A., 99(19): 12415-12420 (2002).
Dull et al., "Insulin-like growth factor II precursor gene organization in relation to insulin gene therapy," Nature 310: 777-781 (1984).
Duncan, J. and M. Welch, "Intracellular metabolism of indium-111-DTPA-labeled receptor targeted proteins," J Nucl Med. 34(10):1728-1738 (1993).
Dunn et al., "Cancer immunoediting: from immunosurveillance to tumor escape.," Nat Immunol. 3(11):991-998 (2002).
Earl et al., "T-Lymphocyte Priming and Protection Against Friend Leukemoa by Vaccinia-Retrovirus env Gene Recombinant," Science 234: 728-731 (1986).
Eastham et al. "Prostate cancer gene therapy: herpes simplex virus thymidine kinase gene transduction followed by ganciclovir in mouse and human prostate cancer models." Hum Gene Ther. 7(4):515-523 (1996).
Ebert et al., "Oncolytic vesicular stomatitis virus for treatment of orthotopic hepatocellular carcinoma in immune-competent rats," Cancer Research 63: 3605-3611 (2003).
Ebert et al., "Syncytia induction enhances the oncolytic potential of vesicular stomatitis virus in virotherapy for cancer," Cancer Research 64: 3265-3270 (2004).
Eck et al., "Gene-Based Therapy" Goodman & Gilman's The Pharmacological Basis of Therapeutics, McGraw-Hill, New York, p. 77-101 (1996).
Ehrengruber, M.U., "Alphaviral gene transfer in neurobiology", Brain Research Bulletin, 59(1): 13-22 (2002).
Eliopoulos et al., "CD40 induces apoptosis in carcinoma cells through activation of cytotoxic ligands of the tumor necrosis factor superfamily," Mol Cell Biol. 20(15):5503-5515 (2000).
Engebrecht et al., "Measuring Gene Expression with Light," Science 227: 1345-1347 (1985).
Escher, A et al., "The β subunit polypeptide of *Vibrio harveyi* luciferase determines light emission at 42° C," Mol Gen Genet. 230(3):385-393 (1991).
Escher, A. and A.A. Szalay, "GroE-mediated folding of bacterial luciferases in vivo," Mol Gen Genet. 238(1-2):65-73 (1993).
Escher, A. et al., "Bacterial luciferase αβ fusion protein is fully active as a monomer and highly sensitive in vivo to elevated temperature," Proc Natl Acad Sci U S A. 86(17):6528-6532 (1989).
Esposito, J.J. and F. Fenner, "Poxviruses", Chapter 85 in Field's Virology, 4th Edn., vol. 2, pp. 2885-2921. Edited by D. M. Knipe and P. M. Howley, Philadelphia: Lippincott Williams & Wilkins, (2001).
Essbauer, S. and W. Ahne, "Viruses of lower vertebrates," J Vet Med B Infect Dis Vet Public Health. 48(6):403-75 (2001).
Estin et al, "Recombinant vaccinia virus vaccine against the human melanoma antigen p97 for use in immunotherapy," Proc. Natl. Acad. Sci. USA 85: 1052-1056 (1988).
Fabricius et al., "Quantitative investigations into the elimination of in vitro-obtained spores of the non-pathogenic *Clostridium butyricum* strain CNRZ 528, and their persistence in organs of different species following intravenous spore administration," Res. Microbiol. 144: 741-753 (1993).
Farkas-Himsley et al., "The bacterial colicin active against tumor cells in vitro and in vivo is verotoxin 1," Proc Natl Acad Sci U S A. 92(15):6996-7000 (1995).

Fatyol, K and A.A. Szalay, "The p14$^{ARF}$ tumor suppressor protein facilitates nucleolar sequestration of hypoxia-inducible factor-II (HIF-1I ) and inhibits HIF-1-mediated transcription," J Biol Chem. 276(30):28421-28429 (2001).
Fatyol, K et al. "Molecular characterization of a stably transformed Bombyx mori cell line: identification of alternative transcriptional initiation sites of the A3 cytoplasmic actin gene." Mol Gen Genet. 260(1):1-8 (1998).
Fatyol, K et al., "An alternative intronic promoter of the Bombyx A3 cytoplasmic actin gene exhibits a high level of transcriptional activity in mammalian cells," Mol Gen Genet. 261(2):337-345 (1999).
Fatyol, K et al., "Mer22-related sequence elements form pericentric repetitive DNA families in primates," Mol Gen Genet. 262(6):931-939 (2000).
Feng et al, "The antitumor activity of a mixed bacterial vaccine against mouse hepatoma," Chinese Pharmaceutical Journal 30(7): 405-407 (1995) [Article in Chinese; English abstract on last page of article].
Fernández-Piñas, F. and C.P. Wolk, "Expresssion of luxCD-E in Anabaena sp. can replace the use of exogenous aldehyde for in vivo localization of transcription by luxAB,"Gene 150:169-174 (1994).
Ferretti et al., "Complete genome sequence of an M1 strain of *Streptococcus pyogenes*," Proc. Natl. Acad. Sci. USA 98(8): 4658-4663 (2001).
Fidler, I.J., "The pathogenesis of cancer metastasis: the 'seed and soil' hypothesis revisited", Nature Cancer Research, 3: 1-6 (2003).
Flexner et al., "Characterization of Human Immunodeficiency Virus gag/pol Gene Products Expressed by Recombinant Vaccinia Viruses," Virology 166: 339-349 (1988).
Flexner et al., "Successful vaccination with a polyvalent live vector despite existing immunity to an expressed antigen," Nature 355:259-262 (1988).
Fodor et al., "Vaccinia virus mediated p53 gene therapy for bladder cancer in an orthotopic murine model," J. Urol. 173(2):604-609 (2005).
Foran, D.R. and W.M. Brown, "Nucleotide sequence of the LuxA and LuxB genes of the bioluminescent marine bacterium *Vibrio fischeri*," Nucleic Acids Res. 16: 777 (1988).
Forbes, N.S. et al., "Sparse Initial Entrapment of Systematically Injected *Salmonella typhimurium* Leads to Heterogenous Accumulation within Tumors," Cancer Res., 63: 5188-5193 (2003).
Fox et al., Erratum to "Anaerobic bacteria as a delivery system for cancer gene therapy: in vitro activation of 5-fluorocytosine by genetically engineered clostridia," Gene Therapy, 3(8):741 (1996).
Fox, A.W., "Emergency and Compassionate-use INDs and Accelerated NDS or ANDA Approvals—Procedures, Benefits and Pitfalls", Chapter 26 in Principles and Practice of Pharmaceutical Medicine, A.J. Fletcher, et al.(Eds.), John Wiley & Sons, pp. 299-305, (2002).
Fox, et al., "Anaerobic bacteria as a delivery system for cancer gene therapy: in vitro activation of 5-fluorocytosine by genetically engineered clostridia," Gene Therapy, 3(2):173-178, (1996).
Francis et al., "Monitoring bioluminescent *Staphyloccus aureus* infections in living mice using a novel luxABCDE construct," Infection and Immunity 68(6): 3594-3600 (2000).
Freed et al., "Survival of Implanted Fetal Dopamine Cells and Neurologic Improvement 12 to 46 Months After Transplantation for Parkinson's Disease," New England Journal of Medicine 327:1549-1555 (1992).
Freitag, N.E. and K.E. Jacobs, "Examination of *Listeria monocytogenes* Intracellular Gene Expression by Using Green Fluorescent Protein of Aequorea victoria," Infect.Immun. 67:1844-1852 (1999).
Friberg, S. and S. Mattson, "On the Growth Rates of Human Malignant Tumors: Implications for Medical Decision Making," Journal of Surgical Oncology, 65: 284-297 (1997).
Friedlos et al., "Three new prodrugs for suicide gene therapy using carboxypeptidase G2 elicit bystander efficacy in two xenograft models," Cancer Res. 62(6):1724-1729 (2002).
Fu et al., "Relationship between gut origin bacteria and wound infection after thermal injury" Zhonghua Wai Ke Za Zhi 32(10):615-618 (1994).
Gallagher, R., "Vaccination Undermined", The Scientist, 17(22): 1-3 (2003).

(56) References Cited

OTHER PUBLICATIONS

Gambhir et al., "Imaging transgene expression with radionuclide imaging technologies," Neoplasia 2(1-2): 118-138 (2000).
Gautam, A., et al., "Delivery systems for pulmonary gene therapy," American Journal of Respiratory Medicine, 1(1):35-46, (2002).
Gelfand et al., "Infections in burn patients: a paradigm for cutaneous infection in the patient as risk" Am. J. Med. 76(5A):158-165 (1984).
Geng, J.G., "Directinal migration of leukocytes: their pathological roles in inflammation and strategies for development of anti-inflammatory therapies", Cell Res., 11(2): 85-88 (2001).
Geng, J.G., "Interaction of vascular endothelial cells with leukocytes, platelets and cancer cells in inflammation, thrombosis and cancer growth and metastasis," Acta Pharmacol. Sin, 24(12): 1297-1300 (2003).
Giacomin, L.T. and A.A. Szalay, "Expression of a PALI promoter luciferase gene function in *Arabidopsis thaliana* in response to infection by phytopathogenic bacteria," Plant Sci. 116: 59-72 (1996).
Giedlin et al., "Vesicular stomatitis virus: an exciting new therapeutic oncolytic virus candidate for cancer or just another chapter from Field's Virology?" Cancer Cell 4: 241-243 (2003).
Gnant et al., "Regional Versus Systemic Delivery of Recombinant Vaccinia Virus as Suicide Gene Therapy for Murine Liver Metastases," Annals of Surgery 230(3): 352-361 (1999).
Gnant et al., "Sensitization of tumor necrosis factor α-resistant human melanoma by tumor-specific in vivo transfer of the gene encoding endothelial monocyte-activating polypeptide II using recombinant vaccinia virus," Cancer Research 59: 4668-4674 (1999).
Gnant et al., "Systemic administration of a recombinant vaccinia virus expressing the cytosine deaminase gene and subsequent treatment with 5-fluorocytosine leads to tumor-specific gene expression and prolongation of survival in mice," Cancer Res. 59(14):3396-3403 (1999).
Gnant, M.F.X. et al, "Tumor-Specific Gene Delivery Using Recombinant Vaccinia Virus in a Rabbit Model of Liver Metastases", Journal of the National Cancer Institute, 91(20): 1744-1750 (1999).
Goebel et al., "Appendix to 'The complete DNA Sequence of Vaccinia Virus,'" Virology 179: 517-563 (1990).
Goebel et al., "The complete DNA sequence of vaccinia virus," Virology 179:247-266 (1990).
Goetz et al., "Multicenter Study of Autologous Adrenal Medullary Transplantation to the Corpus Striatum in Patients with Advanced Parkinson's Disease", N. Eng. J. Med. 320:337-341 (1989).
Goetz, M et al., "Microinjection and growth of bacteria in the cytosol of mammalian host cells," Proc Natl Acad Sci U S A. 98(21):12221-12226. (2001).
Golstein, P., "Cell death: TRAIL and its receptors," Curr Biol. 7(12):R750-R753 (1997).
Gomella, L.G. et al., "Phase I Study of Intravesical Vaccinia Virus As a Vector for Gene Therapy of Bladder Cancer", J. Urology, 166: 1291-1295 (2001).
Gómez, C.E. and M. Esteban, "Recombinant proteins produced by vaccinia virus vectors can be incorporated within the virion (IMV form) into different compartments," Arch. Virol., 146: 875-892 (2001).
Gorecki, "Prospects and problems of gene therapy: an update" Expert Opin. Emerging Drugs 6(2):187-198 (2001).
Graff, C. and K. Wittrup, "Theoretical Analysis of Antibody Targeting of Tumor Spheroids: Importance of Dosage for Penetration, and Affinity for Retention", Cancer Res., 63: 1288-1296 (2003).
Gray, J., "Evidence emerges for early metastasis and parallel evolution of primary and metastatic tumors", Cancer Cell, 4(1): 4-6 (2003).
Greco et al., "Development of a novel enzyme/prodrug combination for gene therapy of cancer: horseradish peroxidase/indole-3-acetic acid," Cancer Gene Ther. 7(11):1414-1420 (2000).
Green et al., "Necrotizing Fasciitis," Chest 110(1):219-229 (1996).
Green, D. and G. Evan, "A matter of life and death", Cancer Cell, 1: 19-30 (2002).
Greer III, L. and A. Szalay, "Imaging of light emission from the expression of luciferases in living cells and organisms: a review," Luminescence. 17(1):43-74 (2002).
Greinwald et al., "Treatment of lymphangiomas in children: an update of Picibanil (Ok-432) sclerotherapy," Otolaryngol Head Neck Surg 121(4): 381-387 (1999).
Gribskov et al., "Sigma factors from *E. coli*, *B. subtilis*, phage SPO1, and phage T4 are homologous proteins," Nucl. Acids Res. 14:6745-6763 (1986).
Gridley et al., "Evaluation of radiation effects against C6 glioma in combination with vaccinia virus-p53 gene therapy," Int J Oncol. 13(5):1093-1098 (1998).
Gridley et al., "Proton radiation and TNF-α/Bax gene therapy for orthotopic C6 brain tumor in Wistar rats," Technol Cancer Res Treat. 3(2):217-227 (2004).
Griffin, D.E., "A Review of Alphavirus Replication in Neurons", Neuroscience and Biobehavioral Reviews, 22(6): 721-723 (1998).
Grote et al., "Live attenuated measles virus induces regression of human lymphoma xenografts in immunodeficient mice," Blood 97(12):3746-3754 (2001).
Grove et al. "Virus-directed enzyme prodrug therapy using CB1954" Anti-Cancer Drug Design 14(6) 461-472 (1999).
Gura, T., "Systems for identifying new drugs are often faulty," Science, 278:1041-1042, (1997).
Guy et al., "Expression of the neu protooncogene in the mammary epithelium of transgenic mice induces metastatic disease," Proc. Natl. Acad. Sci.USA 89: 10578-10582 (1992).
Hacein-Bey-Abina, S. et al., "A Serious Adverse Event after Successful Gene Therapy for X-Linked Severe Combined Immunodeficiency", N. Engl. J. Med., 348(3): 255-266 (2003).
Hadley, R.G. et al., "Conservation of DNA regions adjacent to nifKDH homologous sequences in diverse slow-growing *Rhizobium* strains," J Mol Appl Genet. 2(3):225-36 (1983).
Haghighat et al. "Antitumor effect of IL-2, p53, and bax gene transfer in C6 glioma cells," Anticancer Res. 20(3A):1337-42 (2000).
Hall et al., "Adenovirus-mediated herpes simplex virus thymidine kinase gene and ganciclovir therapy leads to systemic activity against spontaneous and induced metastasis in an orthotopic mouse model of prostate cancer," Int J Cancer. 70(2):183-7 (1997).
Hall et al., "In vitro efficacy of transferrin-toxin conjugates against glioblastoma multiforme," J Neurosurg. 76(5):838-44 (1992).
Hall et al., "In vivo efficacy of intrathecal transferrin-*Pseudomonas* exotoxin A immunotoxin against LOX melanoma," Neurosurgery 34(4):649-55; discussion 655-6 (1994).
Hall, F., et al., "Targeting retroviral vectors to vascular lesions by genetic engineering of the MoMLV gp70 envelope protein," Human Gene Therapy, 8:2183-2192 (1997).
Halsell, J.S. et al., "Myopericarditis Following Smallpox Vaccination Among Vaccinia-Naïve US Military Personnel", J. Am. Med. Assoc., 289(24): 3283-3289 (2003).
Hamblin et al., "Rapid control of wound infections by targeted photodynamic therapy monitored by in vivo bioluminescence imaging," Photochemistry and Photobiology 75(1): 51-57 (2002).
Hanahan, D. and R.A. Weinberg, "The Hallmarks of Cancer", Cell, 100: 57-70 (2000).
Hansen et al., "Assessment of GFP fluorescence in cells of *Streptococcus gordonii* under conditions of low pH and low oxygen concentration," Microbiology 147: 1383-1391 (2001).
Hansen, R.M. and J.A. Libnoch, "Remission of Chronic Lymphocytic Leukemia After Smallpox Vaccination", Arch. Intern. Med., 138: 1137-1138 (1978).
Harrison et al., "Gene-modified PA1-STK cells home to tumor sites in patients with malignant pleural mesothelioma," Ann Thorac Surg. 70(2):407-11 (2000).
Hasegawa et al., "Avoidance of bone marrow suppression using A-5021 as a nucleoside analog for retrovirus-mediated herpes simplex virus type I thymidine kinase gene therapy,." Cancer Gene Ther. 7(4):557-62 (2000).
Hasegawa et al., "In vivo tumor delivery of the green fluorescent protein gene to report future occurrence of metastasis," Cancer Gene Therapy 7: 1336-1340 (2000).
Hatta, "Antitumor Mechanisms of *Eubacterium lentum* and its Components," Asian Pacific Journal of Allergy and Immunology 13: 129-137 (1995).
Hawkins, L.K. et al., "Oncolytic biotherapy: a novel therapeutic platform", The Lancet Oncology, 3: 17-26 (2002).

(56) References Cited

OTHER PUBLICATIONS

Hemann et al., "High-Copy Expression Vector Based on Amplification-Promoting Sequences", DNA and Cell Biology 13:437-445 (1994).
Hermiston, T.W. and I. Kuhn, "Armed therapeutic viruses: Strategies and challenges to arming oncolytic viruses with therapeutic genes", Cancer Gene Therapy, 9: 1022-1035 (2002).
Hen-linger et al., "Neural precursor cells for delivery of replication-conditional HSV-1 vectors to intracerebral gliomas," Mol Ther. 1(4):347-57 (2000).
Hershey, P. et al., "Adjuvant Immunotherapy of Patients With High-Risk Melanoma Using Vaccinia Viral Lysates of Melanoma: Results of a Randomized Trial", Journal of Clinical Oncology, 20(20): 4181-4190 (2002).
Hess et al., "*Listeria monocytogenes* p60 supports host cell invasion by and in vivo survival of attenuated *Salmonella typhimurium*," Infect Immun. 63(5):2047-53 (1995).
Hetz et al., "Microcin E492, a channel-forming bacteriocin from *Klebsiella pneumoniae*, induces apoptosis in some human cell lines," Proc Natl Acad Sci U S A. 99(5):2696-701 (2002).
Hiller et al., "Characterization of Intracellular and Extracellular Vaccinia Virus Variants: $N_1$-Isonicotinoyl-$N_2$-3-Methyl-4-Chlorobenzoylhydrazine Interferes with Cytoplasmic Virus Dissemination and Release," Journal of Virology 39(3): 903-913 (1981).
Hollinshead, M. et al., "Vaccinia virus utilizes microtubules for movement to the cell surface," Journal of Cell Biology, 154: 389-402 (2001).
Holló, G et al., "Evidence for a megareplicon covering megabases of centromeric chromosome Segments," Chromosome Res. 4(3):240-7 (1996).
Hosokawa et al., "Pituitary Carcinoma of Pars Distalis as a Common Neoplasm in Fischer-344 Rats," Toxicol. Pathol. 21: 283-287 (1993).
Hostanska et al., "Aqueous ethanolic extract of St. John's wort (*Hypericum perforatum* L.) induces growth inhibition and apoptosis in human malignant cells in vitro," Pharmazie 57(5):323-31 (2002).
Hsueh et al., "Outbreak of *Pseudomonas fluorescens* bacteremia among oncology patients," J Clin Microbiol. 36(10):2914-7 (1998).
Huang et al., "Bacterial penetration across the blood-brain barrier during the development of neonatal meningitis," Microbes and Infection 2(10):1237-1244 (2000).
Huang et al., "Impact of liver P450 reductase suppression on cyclophosphamide activation, pharmacokinetics and antitumoral activity in a cytochrome P450-based cancer gene therapy model," Cancer Gene Ther. 7(7):1034-42 (2000).
Huang et al., "Oncolysis of hepatic metastasis of colorectal cancer by recombinant vesicular stomatitis virus in immune-competent mice," Mol. Ther. 8(3): 434-440 (2003).
Hughes, R.G. and N. Turner, "Financial Aspects of Clinical Trials", Chapter 42 in Principles and Practice of Pharmaceutical Medicine, A.J. Fletcher, et al.(eds.), pp. 501-512, John Wiley & Sons, Ltd. (2002).
Humlova, Z. et al., "Vaccinia virus induces apoptosis of infected macrophages," J. General Virol., 83: 2821-2832 (2002).
Hurst et al., "A novel model of a metastatic human breast tumour xenograft line," Br. J. Cancer 68: 274-276 (1993).
Ianaro et al., "A nitric oxide synthase inhibitor reduces inflammation, down-regulates inflammatory cytokines and enhances interleukin-10 production in carrageenin-induced oedema in mice," Immunology. 82(3):370-5 (1994).
Ianaro et al., "Expression of TGF-β in attenuated *Salmonella typhimurium*: oral administration leads to the reduction of inflammation, Il-2 and IFN-β, but enhancement of IL-10, in carrageein-induced oedema in mice," Immunology 84:8-15 (1995).
Isaacs et al., "Vaccinia virus complement-control protein prevents antibody-dependent complement-enhanced neutralization of infectivity and contributes to virulence," Proc Natl Acad Sci U S A. 89:628-632 (1992).
Jacobs et al., "Positron Emission Tomography-based Imaging of Transgene Expression Mediated by Replication-conditional, Oncolytic Herpes Simplex Virus Type I Mutant Vectors in Vivo," Cancer Research 61: 2983-2995 (2001).
Jain, R.K. and B.T. Fenton, "Intratumoral Lymphatic Vessels: A Case of Mistaken Identity or Malfunction?", Journal of the National Cancer Institute, 94(6): 417-421 (2002).
Jain, R.K. and N.S. Forbes, "Can engineered bacteria help control cancer," Proc. Natl. Acad. Sci. USA 98(26): 14748-14750 (2001).
Jain, R.K., "Molecular regulation of vessel maturation", Nat. Med., 9(6): 685-693 (2003).
Jemal, A. et al., "Cancer Statistics, 2003", CA Cancer J Clin, 53(1): 5-26 (2003).
Jeong, K.J. and S.Y. Lee, "Secretory Production of Human Leptin in *Escherichia coli*," Biotechnol.Bioeng. 67:398-407 (2000).
Jiang et al. "Apoptosis in human hepatoma cell lines by chemotherapeutic drugs via Fas-dependent and Fas-independent pathways," Hepatology. 29(1):101-10 (1999).
Johnson et al., "An update on the vaccinia virus genome," Virology 196: 381-401 (1993).
Johnson et al., "Improved tumor-specific immunotoxins in the treatment of CNS and leptomeningeal neoplasia," J Neurosurg. 70(2):240-8 (1989).
Joklik, W.K., "The Purification of Four Strains of Poxviruses," Virology 18:9-18 (1962).
Jordan et al., "Melanocyte-Directed enzyme prodrug therapy (MDEPT): development of second generation prodrugs for targeted treatment of malignant melanoma," Bioorg Med Chem. 9(6):1549-58 (2001).
Kaklij et al., "Antitumor activity of *Streptococcus thermophilus* against fibrosarcoma: role of T-cells," Cancer Lett. 56(1):37-43 (1991).
Kaklij, G.S. and S.M. Kelkar, "Tumor-specific transplantation resistance in mice after treatment of initial tumors with *Streptococcus thermophilus*," Microbiol Immunol. 40(1):55-8 (1996).
Kammertoens et al., "Combined chemotherapy of murine mammary tumors by local activation of the prodrugs ifosfamide and 5-fluorocytosine," Cancer Gene Ther. 7(4):629-36 (2000).
Kan et al., "Direct retroviral delivery of human cytochrome P450 2B6 for gene-directed enzyme prodrug therapy of cancer," Cancer Gene Ther. 8(7):473-82 (2001).
Kaniga et al., "Homologs of the Shigella IpaB and IpaC Invasins are Required for *Salmonella typhimurium* Entry into Cultured Epithelial Cells," J. Bacteriol. 177: 3965-3971 (1995).
Kantor et al., "Antitumor Activity and Immune Responses Induced by a Recombinant Carcinoembryonic Antigen-Vaccinia Virus Vaccine," J. Natl. Cancer Inst. 84: 1084-1091 (1992).
Kaplitt et al.,, "Mutant herpes simplex virus induced regression of tumors growing in immunocompetent rats," J. Neurooncol 19(2): 137-147 (1994).
Kato et al., "Antitumor activity of *Lactobacillus casei* in mice," Gann. 72(4):517-23 (1981).
Kato et al., "Correlation between increase in Ia-bearing macrophages and induction of T cell-dependent antitumor activity by *Lactobacillus casei* in mice," Cancer Immunol Immunother. 26(3):215-21 (1988).
Katz et al., "Mutations in the vaccinia virus A33R and B5R envelope proteins that enhance release of extracellular virions and eliminate formation of actin-containing microvilli without preventing tyrosine phosphorylation of the A36R protein," J. Virology 77:12266-12275 (2003).
Kaufman et al., "A recombinant vaccinia virus expressing human carcinoembryonic antigen CEA", Int. J. Cancer 48(6):900-907 (1991).
Kaufman, H., et al., "A recombinant vaccinia virus expressing human carcinoembryonic antigen CEA," International Journal of Cancer, 48(6):900-907, (1991).
Kawa, A. and S. Arakawa, "The Effect of Attenuated Vaccinia Virus AS Strain on Multiple Myeloma; A Case Report", Japan. J. Exp. Med. 58(1): 79-81 (1987).
Kawamura et al., "Expression of *Escherichia coli* uracil phosphoribosyltransferase gene in murine colon carcinoma cells augments the antitumoral effect of 5-fluorouracil and induces protective immunity," Cancer Gene Ther. 7(4):637-43 (2000).

(56) References Cited

OTHER PUBLICATIONS

Kaye et al., "A single amino acid substitution results in a retinoblastoma protein defective in phosphorylation and oncoprotein binding" Proc. Natl. Acad. Sci. USA 87:6922-6926 (1990).
Keith, K.A. et al., "Evaluation of Nucleoside Phosphonates and Their Analogs and Prodrugs for Inhibition of Orthopoxvirus Replication," Antimicr. Agents Chemothera., 47(7): 2193-2198 (2003).
Kelkar et al., "Antitumor activity of lactic acid bacteria on a solid fibrosarcoma, sarcoma-180 and Ehrlich ascites carcinoma, " Cancer Lett. 42(1-2):73-7 (1988).
Kelland et al. "Of mice and men: values and liabilities of the athymic nude mouse model in anticancer drug development" European J. Cancer 40:827-836 (2004).
Kerbel et al., "Human Tumor Xenografts as Predictive Preclinical Models for Anticancer Drug Activity in Humans" Cancer Biology & Therapy 2:4 suppl. 1, S134-S139 (2003).
Keresó, J. et al., "De novo chromosome formations by large-scale amplification of the centromeric region of mouse chromosomes," Chromosome Res. 4(3):226-39 (1996).
Kern, E.R., "In vitro activity of potential anti-poxvirus agents", Antiviral Research 57: 35-40 (2003).
Ketlinsky et al., "[Mechanism of the anti-tumoral effect of the blastolysin fraction isolated from *Lactobacillus bulgaricus*]," Vopr Onkol. 33(3):51-6 (1987) [Article in Russian; English abstract on last page of article].
Kihara, A. and I. Pastan, "Analysis of Sequences Required for the Cytotoxic Action of a Chimeric Toxin Composed of *Pseudomonas* Exotoxin and Transforming Growth Factor α,"Bioconj.Chem. 5: 532-538 (1994).
Kim et al. "A tale of two trials: selectively replicating herpesviruses for brain tumors" Gene Therapy 7(10):815-816 (2000).
Kim, E.M. et al., "Overview analysis of adjuvant therapies for melanomaFa special reference to results from vaccinia melanoma oncolysate adjuvant therapy trials", Surgical Oncology, 10: 53-59 (2001).
Kimura et al., "Selective localization and growth of *Bifidobacterium bifidum* in mouse tumors following intravenous administration," Cancer Res. 40(6):2061-8 (1980).
Kirn, D.H. and F. McCormick, "Replicating viruses as selective cancer therapeutics," Mol Med Today 2(12): 519-527 (1996).
Kirn, E.M. et al., "Overview analysis of adjuvant therapies for melanomaFa special reference to results from vaccinia melanoma oncolysate adjuvant therapy trials", Surgical Oncology, 10: 53-59 (2001).
Kleer, C.G. et al., "Molecular biology of breast cancer metastasis Inflammatory breast cancer: clinical syndrome and molecular determinants," Breast Cancer Res. 2: 423-429 (2000).
Kneissl, M. et al., " Interaction and assembly of murine pre-replicative complex proteins in yeast and mouse cells," J Mol Biol. 327(1):111-28 (2003).
Kohler, G., and C. Milstein, "Continuous cultures of fused cells secreting antibody of predefined specificity," Nature, 256:495-497, (1975).
Kohwi et al., "Antitumor effect of *Bifidobacterium infantis* in mice," Gann. 69(5):613-8 (1978).
Kokkinakis et al., "Effect of long-term depletion of plasma methionine on the growth and survival of human brain tumor xenografts in athymic mice," Nutr Cancer. 29(3):195-204 (1997).
Kolowsky K.S. et al., "Length of foreign DNA in chimeric plasmids determines the efficiency of its integration into the chromosome of the *Cyanobacterium synechococcus* R2," Gene 27(3):289-99 (1984).
Kondo et al., "Activity of Immunotoxins Constructed with Modified *Pseudomonas* Exotoxin a Lacking the Cell Recognition Domain," J.Biol.Chem. 263: 9470-9475 (1988).
Kopylova-Sviridova et al., "Transient expression assay in a baculovirus system using firefly luciferase gene as a reporter," Virus Genes. 6(4):379-86 (1992).
Kotwal et al., "Mapping and Insertional Mutagenesis of a Vaccinia Virus Gene Encoding a 13, 800-Da Secreted Protein," Virology 171:579-587 (1989).
Koyama et al., "Combined suicide gene therapy for human colon cancer cells using adenovirus-mediated transfer of *Escherichia coli* cytosine deaminase gene and *Escherichia coli* uracil phosphoribosyltransferase gene with 5-fluorocytosine," Cancer Gene Ther. 7(7):I015-22 (2000).
Kozak, M., "Structural features in Eukaryotic mRNAs that modulate the Initiation of Translation," J. Biol. Chem. 266:19867-19870 (1991).
Krauss, O. et al., "An investigation of incorporation of cellular antigens into vaccinia virus particles", Journal of General Virology, 83: 2347-2359 (2002).
Kruse, M, et al., "Enzyme assembly after de novo synthesis in rabbit reticulocyte lysate involves molecular chaperones and immunophilins," J Biol Chem. 270(6):2588-94 (1995).
Kubes, P., "Introduction: The complexities of leukocyte recruitment", Seminars in Immunol., 14: 65-72 (2002).
Kunik et al., "Genetic transformation of HeLa cells by *Agrobacterium*," Proc Natl Acad Sci U S A. 98(4):1871-6 (2001).
Kunkel, E.J. and E.C. Butcher, "Plasma-cell homing", Nature Reviews Immunology, 3: 822-829 (2003).
Kutinova et al., "Hepatitis B virus proteins expressed by recombinant vaccinia viruses: influence of preS2 sequence on expression surface and nucleocapsid proteins in human diploid cells," Archives of Virology 134:1-15 (1994).
Kutinova et al., "Search for optimal parent for recombinant vaccinia virus vaccines. Study of three vaccinia virus vaccinal strains and several virus lines derived from them," Vaccine 13(5): 487-493 (1995).
Kwak, H. et al., "Poxviruses as vectors for cancer immunotherapy", Curr. Opin. Drug Disc. Develop., 6(2): 161-168 (2003).
Lachmann, R.H. and S. Efstathiou, "Gene transfer with herpes simplex vectors," Curr Opin Mol Ther. 1(5):622-32 (1999).
Lamberton et al., "Construction and characterization of a bioluminescent *Streptococcus pyogene*," Proceedings of the 12th International Symposium on Bioluminescence and Chemiluminescence Progress & Current Appications, Stanley, P.E. and L.J. Kricka et al (Eds). World Scientific Publishing Co. Pte. Ltd., pp. 85-88 (2002).
Lamberton et al., "Generation and characterization of a bioluminescent *Streptococcus pyogenes*," Proceedings of the 12th International Symposium on Bioluminescence & Chemiluminescence: Apr. 5-9, 2002, Robinson College, University of Cambridge, UK, p. 3.22 (2002).
Lamensans et al., "Enhancement of immunity against murine syngeneic tumors by a fraction extracted from non-pathogenic mycobacteria," Proc Natl Acad Sci U S A. 72(9):3656-60 (1975).
Lammertyn et al., "Evaluation of a novel subtilisin inhibitor gene and mutant derivatives for the expression and secretion of mouse tumor necrosis factor alpha by *Streptomyces lividans*," Appl Environ Microbiol. 63(5):1808-13 (1997).
Langridge W.H. et al, "Detection of baculovirus gene expression in insect cells and larvae by low light video image analysis," J Virol Methods. 61(1-2):151-6 (1996).
Langridge W.H. et al., "Uptake of DNA and RNA into cells mediated by electroporation," Methods Enzymol. 153:336-50. (1987).
Langridge, W.H. and , A.A.Szalay, "Bacterial and coelenterate luciferases as reporter genes in plant cells," Chapter 37 in Methods Mol Biol. 82:385-96.(1998).
Larocca et al., "Gene transfer to mammalian cells using genetically targeted filamentous bacteriophage," FASEB Journal, 13:727-734, (1999).
Larson et al. "Triumph over mischance: a role for nuclear medicine in gene therapy," J Nucl Med. 38(8):1230-3 (1997).
Lathe et al., "Tumour prevention and rejection with recombinant vaccinia," Nature (London) 326: 878-880 (1987).
Lattime et al., "In Situ Cytokine Gene Transfection Using Vaccinia Virus Vectors," Semin Oncol 23(1): 88-100 (1996).
Lawrence J.C., "The bacteriology of burns", J. of Hospital Infection 6: 3-17 (1985).
Lee et al. "Prodrug and antedrug: two diametrical approaches in designing safer drugs," Arch. Pharm. Res. 25(2): 111-136 (2002).

(56) References Cited

OTHER PUBLICATIONS

Lee et al., "Molecular attenuation of vaccinia virus: mutant generation and animal characterization," Journal of Virology 66:2617-2630 (1992).
Lee et al., "The lux genes of the luminous bacterial symbiont *Photobacterium leiognathi*, of the ponyfish," Eur. J. Biochem. 201: 161-167 (1991).
Leenders et al., "Blood to brain iron uptake in one Rhesus monkey using [Fe-52]-citrate and positron emission tomography (PET): influence of haloperidol," J. Neural.Transm.Suppl. 43: 123-132 (1994).
Legocki et al., "Bioluminescence in soybean root nodules: Demonstration of a general approach to assay gene expression in vivo by using bacterial luciferase," Proc. Natl. Acad. Sci 83: 9080-9084 (1986).
Lemmon et al., "Anaerobic bacteria as a gene delivery system that is controlled by the tumor microenvironment," Gene Therapy 4: 791-796 (1997).
Lemmon et al., "Anaerobic bacteria as a gene delivery system to tumors," Proceedings of the 85th Annual Meeting of the American Association for Cancer Research, San Francisco, CA Apr. 10-13, 1994, published in: Proc. Am. Cancer Research Assn 35: 374 (1994).
Lewis et al., "Comparison of Four $^{64Cu}$-Labeled Somatostatin Analogues in Vitro and in a Tumor-Bearing Rat Model: Evaluation of New Derivatives for Positron Emission Tomography Imaging and Targeted Radiotherapy," J. Med. Chem. 42: 1341-1347 (1999).
Ley, K., "Integration of inflammatory signals by rolling neutrophils", Immunological Reviews, 186: 8-18 (2002).
Ley, K., "The role of selectins in inflammation and disease", Trends in Molec. Med., 9(6): 263-268 (2003).
Li et al "An engineered and assembled fusion protein of antitumor antibiotic lidamycin and scFV antibody directed against type IV collagenase" Yaoxue Xuebao 35(7) 488-91 (Jul. 2000) [English abstract on last page of article].
Li et al., "*Bifidobacterium* adolescentis as a delivery system of endostatin for cancer gene therapy: Selective Inhibitor of angiogenesis and hypoxic tumor growth," Cancer Gene Therapy 10: 105-111 (2003).
Li et al., "Enzyme/prodrug gene therapy approach for breast cancer using a recombinant adenovirus expressing *Escherichia coli* cytosine deaminase," Cancer Gene Ther. 4(2):113-7 (1997).
Liau et al., "Treatment of intracranial gliomas with bone marrow-derived dendritic cells pulsed with tumor antigens," J. Neurosurg. 90(6): 1115-1124 (1999).
Lindsey, H., "Modified cold virus kills colon cancer," Lancet Oncology, 3(5):264, (2002).
Lindvall et al., "Grafts of Fetal Dopamine Neurons Surive and Improve Motor Function in Parkinson's Disease," Science 237:574-577 (1990).
Liu et al., "An E1B-19 kDa gene deletion mutant adenovirus demonstrates tumor necrosis factor-enhanced cancer selectivity and enhanced oncolytic potency," Molecular Therapy 9(6): 786-803 (2004).
Liu et al., "Anticancer efficacy of systemically delivered anaerobic bacteria as gene therapy vectors targeting tumor hypoxia/necrosis," Gene Ther. 9(4):291-6 (2002).
Liu, H et al., "Detection of GDNF secretion in glial cell culture and from transformed cell implants in the brains of live animals," Mol Genet Genomics. 266(4):614-23. (2001).
Liu, J. et al., "Visualizing and quantifying protein secretion using a Renilla luciferase-GFP fusion protein," Luminescence. 15(1):45-49 (2000).
Lopez et al., "Infections in children with malignant disease in Argentina," Cancer 47(5): 1023-1030 (1981).
Lorenz et al., "Expression of the *Renilla reniformis* luciferase gene in mammalian cells," J Biolumin Chemilumin. 11(1):31-7 (1996).
Lorenz et al., "Isolation and expression of a cDNA encoding *Renilla reniformis* luciferase," PNAS USA 88: 4438-4442 (1991).
Louie, A.Y. et al., "In vivo visualization of gene expression using magnetic resonance imaging", Nature Biotechnology, 18: 321-325 (2000).
Lu et al., "Delivery of adenoviral vectors to the prostate for gene therapy," Cancer Gene Therapy 6(1):64-72 (1999).
Luscinskas, F.W. et al., "Leukocyte transendothelial migration: A junctional affair", Seminars in Immunology, 14: 105-113 (2002).
Luscinskas, F.W. et al., "The role of endothelial cell lateral junctions during leukocyte trafficking", Immunological Reviews, 186: 57-67 (2002).
Lusso, P., "Chemokines and Viruses: The Dearest Enemies", Virology, 273: 228-240 (2000).
Lutz, R., and H. Bujard, "Independent and tight regulation of transcriptional units in *Escherichia coli* via the LacR/O, the TetR/O and AraC/$I_1$-$I_2$ regulatory elements," Nucleic Acids Research, 25:1203-1210, (1997).
Lyford, J., "Gene therapy 'cause T-cell leukemia': Insertional mutagenesis pinpointed as cause of T-cell Leukemia in X-SCID gene therapy trial", The Scientist, (Daily News, Oct. 20, 2003) pp. 1-4 (2003).
MacDonald, I.C. et al., "Cancer spread and micrometastasis development: quantitative approaches for in vivo models", BioEssays, 24: 885-893 (2002).
Mackenzie et al., "Human mesenchymal stem cells persist, demonstrate site-specific multipotential differentiation, and are present in sites of wound healing and tissue regeneration after transplantation into fetal sheep," Blood Cells, Molecules, and Diseases 27(3): 601-604 (2001).
MacLaren et al. "Receptive non-invasive imaging of the dopamine D2 recepter gene in living animals" Gene Therapy (MacMillan Press)v.6 pp. 785-791, (May 1995).
MacLeod R.A .et al., "Expression of genes from the marine bacterium *Alteromonas haloplanktis* 214 in *Escherichia coli* K-12," Arch Microbiol. 142(3):248-52 (1985).
Maeda, H. et al., "Tumor vascular permeability and the EPR effect in macromolecular therapeutics: a review", J. Controlled Release, 65: 271-284 (2000).
Mahy, B.W.J., "An overview on the use of a viral pathogen as a bioterrorism agent: why smallpox?", Antivir. Res., 57: 1-5 (2003).
Maina C.V. et al., "Molecular weight determination program," Nucleic Acids Res. 12(1 Pt 2):695-702 (1984).
Makower, D. et al., "Phase II Clinical Trial of Intralesional Administration of the Oncolytic Adenovirus ONYX-015 in Patients with Hepatobiliary Tumors with Correlative p53 Studies," Clin. Cancer Res., 9: 693-702 (2003).
Martino et al., "Bacteremia due to glucose non-fermenting gram-negative bacilli in patients with hemoatological neoplasias and solid tumors," Eur J Clin Microbiol Infect Dis. 15(7):610-5 (1996).
Mastrangelo, M.J. et al., "Poxvirus vectors: orphaned and underappreciated", J. Clin. Invest., 105(8): 1031-1034 (2000).
Matz et al., "Fluorescent proteins from nonbioluminescent Anthozoa species," Nat.Biotech. 17: 969-973 (1999).
Mayerhofer, R et al., "Monitoring of spatial expression of firefly luciferase in transformed zebrafish," J Biolumin Chemilumin. 10(5):271-5 (1995).
Mayford et al., "CaMKII Regulates the Frequency-Response Function of Hippocampal Synapses for the Production of Both LTD and LTP," Cell 81: 891-904 (1995).
Mayr et al., "The Smallpox Vaccination Strain MVA: Marker, Genetic Structure, Experience Gained with the Parenteral Vaccination and Behavior in Organisms with a Debilitated Defense Mechanism," Zentbl. Bakteriol. Hyg. Abt 1 Orig. B 167: 375-390 (1978) [In German, English abstract on first page of article].
McAllister et al., "Recombinant yellow fever viruses are effective therapeutic vaccines for treatment of murine experimental solid tumors and pulmonary metastases," J. Virol. 74:9197-9205 (2000).
McAneny et al., "Results of a Phase I trial of a recombinant vaccinia virus that expresses carcinoembryonic antigen in patients with advanced colorectal cancer,"Ann. Surg. Oncol. 3(5): 495-500 (1996).
McCart, J.A. et al., "Complex interaction between the replicating oncolytic effect and the enzyme/prodrug effect of vaccinia-mediated tumor regression", Gene Therapy, 7: 1217-1223 (2000).

(56) References Cited

OTHER PUBLICATIONS

McCart, J.A. et al., "Systemic Cancer Therapy with a Tumor-selective Vaccinia Virus Mutant Lacking Thymidine Kinase and Vaccinia Growth Factor Genes", Cancer Research, 61: 8751-8757 (2001).
McCluskie et al., "Route and Method of Delivery of DNA Vaccine Influence Immune Responses in Mice and Non-Human Primates" Mol. Med. 5:287-300 (1999).
McCluskie, M.J., et al., "Route and method of delivery of DNA vaccine influence immune responses in mice and non-human primates," Molecular Medicine, 5:287-300, (1999).
McDonald, D.M. and P.L. Choyke, "Imaging of angiogenesis: from microscope to clinic", Nature Medicine, 9(6): 713-725 (2003).
McIntosh et al., "A probiotic strain of *L. acidophilus* reduces DMH-induced large intestinal tumors in male Sprague-Dawley rats," Nutr Cancer. 35(2):153-9 (1999).
Meadows et al., "Some biological properties and an in vivo evaluation of tyrosine phenol-lyase on growth of B-16 melanoma," Cancer Res. 36(1):167-7 (1976).
Meager, a. et al., "The Development of the Regulatory Process in Europe for Biological Medicines: How it Affects Gene Therapy Products", Chapter 16 in Gene Therapy Technologies, Applications and Regulations, A. Meager (Ed.), John Wiley & Sons Ltd., pp. 319-346 (1999).
Meck et al., "A virus-directed enzyme prodrug therapy approach to purging neuroblastoma cells from hematopoietic cells using adenovirus encoding rabbit carboxylesterase and CPT-11," Cancer Res. 61(13):5083-9 (2001).
Meighen, E.A. and R.B. Szittner, "Multiple Repetitive Elements and Organization of the lux Operons of Luminescent Terrestrial Bacteria," J. Bacteriol. 174(16):5371-5381 (1992).
Mengaud et al., "Expression in *Escherichia coli* and Sequence Analysis of the Listeriolysin O Determinant of *Listeria monocytogenes*," Infectinunun. 56(4): 766-772 (1988).
Meyer et al., "Mapping of deletions in the genome of the highly attenuated vaccinia virus MVA and their influence on virulence," Journal of General Virology 72(Pt 5): 1031-1038 (1991).
Micheau et al., "Sensitization of cancer cells treated with cytotoxic drugs to fas-mediated cytotoxicity," J Natl Cancer Inst. 89(11):783-9 (1997).
Michl et al., "Claudin-4: a new target for pancreatic cancer treatment using *Clostridium perfringens* enterotoxin," Gastroenterology 121(3):678-84 (2001).
Middleton, J. et al., "Leukocyte extravasation: chemokine transport and presentation by the endothelium", Blood, 100(12): 3853-3860 (2002).
Miki et al., "Methioninase gene therapy of human cancer cells is synergistic with recombinant methioninase treatment," Cancer Res. 60(10):2696-702 (2000).
Mikryukov et al., "Structural-functional organization of segment of vaccinia virus genome," Soviet Biotechnology (Biotekhnologiya) 4: 19-25 (1988) [corresponds to pp. 442-449 in the Russian language edition].
Milbrandt, E., "A novel source of enterococcal endocarditis," Clin Cardiol. 21(2):123-6 (1998).
Minton et al., "Chemotherapeutic tumour targeting using clostridial spores," FEMS Microbiol Rev. 17(3):357-64 (1995).
Mirzadeh et al., "Radiometal labeling of immunoproteins: covalent linkage of 2-(4-isothiocyanatobenzyl)diethylenetriaminepentaacetic acid ligands to immunoglobulin," Bioconjug Chem. 1(1):59-65 (1990).
Mizutani et al., "Doxotubicins sensitizes human bladder carcinoma cells to Fas-mediated cytotoxicity," Cancer. 79(6):1180-9 (1997).
Mizutani et al., "Sensitization of human bladder cancer cells to Fas-mediated cytotoxicity by cis-diamminedichloroplatinum (II)," J Urol. 160(2):561-70 (1998).
Mizutani, T and T. Mitsuoka, "Inhibitory effect of some intestinal bacteria on liver tumorigenesis in gnotobiotic C3H/He male mice," Cancer Lett. 11(2):89-95 (1980).

Moats, et al., "A 'smart' magnetic resonance imaging agent that reports on specific enzymatic activity," Angew. Chem. Int. Ed. Eng., 36(7):726-728, (1997).
Mohr et al., "Rabbit cytochrome P450 4B1: A novel prodrug activating gene for pharmacogene therapy of hepatocellular carcinoma," Cancer Gene Ther. 7(7):1008-14 (2000).
Moolten, F.L., "Tumor chemosensitivity conferred by inserted herpes thymidine kinase genes: paradigm for a prospective cancer control strategy," Cancer Res. 46(10):5276-81 (1986).
Moore et al. , "Measuring transferrin receptor gene expression by NMR imaging," Biochimica et Biophysica Acta 1402(3):239-249 (1998).
Moore et al., "Steroid hormone synthesis by a vaccinia enzyme: a new type of virus virulence factor," EMBO J. 1992 11:1973-1980, corrigendum in The EMBO Journal 11(9): 3490 (1992).
Moore, A.E., "Effects of Viruses on Tumors", Annu. Rev. Microbiol., 8: 393-402 (1954).
Moretta, A., "Natural Killer Cells and Dendritic Cells: Rendezvous in Abused Tissues", Nat. Rev. Immunol., 2: 957-964 (2002).
Morinaga et al., "Antitumor Activity and its Properties of *Eubacterium lentum*," Jpn. J. Cancer Res. (Gann) 79: 117-124 (1988).
Morris, D.W. et al., "Plasmid vectors capable of transferring large DNA fragments to yeast," DNA. 1(1):27-36 (1981).
Moss, B., "Poxviridae: the viruses and their replication," Chapter 84 in Field's Virology, 4$^{th}$ Edn., vol. 2, pp. 2849-2883. Edited by D. M. Knipe and P. M. Howley, Philadelphia: Lippincott Williams & Wilkins, (2001).
Moss, B., "Poxviridae: the viruses and their replication," Chapter 83 in Fields Virology, 3rd Edn, pp. 2637-2671. Edited by B. N. Fields, D. M. Knipe & P. M. Howley. Philadelphia: Lippincott—Raven (1996).
Moss, B., "Genetically engineered poxviruses for recombinant gene expression, vaccination, and safety," Proc. Natl. Acad. Sci. USA 93: 11341-11348 (1996).
Moss, B., "Poxvirus vectors: cytoplasmic expression of transferred genes," Curr. Opin. Genet. Dev. 3: 86-90 (1993).
Mountz et al. "Technetium-99m NeoTect imaging in vivo of T cells from hCAR transgenic mice," FASEB J. 16(5):A1211 March Meeting abstract (2002).
Mukherjee et al., "Replication-restricted vaccinia as a cytokine gene therapy vector in cancer: persistent transgene expression despite antibody generation," Cancer Gene Ther. 7(5):663-70 (2000).
Mullen et al., "Viral Oncolysis," The Oncologist 7: 106-119 (2002).
Mulryan et al., "Attenuated recombinant vaccinia virus expressing oncofetal antigen (tumorassociated antigen) 5T4 induces active therapy of established tumors," Mol Cancer Ther 1(12): 1129-1137 (2002).
Munagala et al., "The purine nucleoside phosphorylase from *Trichomonas vaginalis* is a homologue of the bacterial enzyme," Biochemistry 41(33): 10382-10389 (2002).
Muravlev et al., "Protective activity of vaccinia virus envelope proteins isolated with the use of nonionic detergents," Voprosy Virusologii 40(4): 154-8 (1995) ) [article in Russian, English summary on last page of article].
Murosaki et al., "Antitumor effect of heat-killed *Lactobacillus plantarum* L-137 through restoration of impaired interleukin-12 production in tumor-bearing mice," Cancer Immunol Immunother. 49(3):157-64 (2000).
Mutschler et al. "10. Chemotherapy of Malignant Tumors" in: Drug Actions: Basic Principles and Therapeutic Aspects (medpharm (CRC Press), Suttgart, pp. 595-612 (1995).
Myklebust et al., "Eradication of small cell lung cancer cells from human bone marrow with immunotoxins," Cancer Res. 53(16):3784-8 (1993).
Nagahari et al. "Secretion into the culture medium of a foreign gene product from *Escherichia coli*: use of the ompF gene for secretion of human β-endorphin." EMBO J. 4(13A):3589-92 (1985).
Nakamura et al., "Induction of apoptosis in HL60 leukemic cells by anticancer drugs in combination with anti-Fas monoclonal antibody," Anticancer Res. 17(1A):173-9 (1997).
Nakao, H. and T. Takeda, "*Escherichia coli* Shiga toxin," J Nat Toxins. 9(3):299-313 (2000).

(56) References Cited

OTHER PUBLICATIONS

Nauciel, C. and A.F. Goguel, "Inhibition of tumor growth by the peptidoglycan from *Bacillus megaterium*," J Natl Cancer Inst. 59(6):1723-6 (1977).
NCBI Nucleotide AF012825.
NCBI Nucleotide AF380138.
NCBI Nucleotide AX003206.
NCBI Nucleotide AY243312.
NCBI Nucleotide AY484669.
NCBI Nucleotide AY603355.
NCBI Nucleotide M35027.
NCBI Nucleotide M57977.
NCBI Nucleotide U94848.
NCBI Nucleotide X69198.
NCBI Nucleotide X94355.
NCBI Nucleotide. AF095689.
NCBI Nucleotide. AY009089.
NCBI Protein AAA48282.
Needleman et al., "A general method applicable to the search for similarities in the amino acid sequences of two proteins," J. Mol. Biol. 48:443-453 (1970).
Netesova et al., "Structural and functional studies of the HindIII-I-Genome Fragment of Vaccinia virus Strain L-IVP," Mol Biol (Mosk.) Nov.-Dec.; 25(6): 1526-32 (1991) ) [article in Russian, English summary on last page of article].
Nettleton, P.F. et al., "Parapoxviruses are strongly inhibited in vitro by cidofovir," Antivir. Res., 48: 205-208 (2000).
Newton et al. "Expression and characterization of recombinant human eosinophil-derived neurotoxin and eosinophil-derived neurotoxin-anti-transferrin receptor sFv," J. Biol. Chem. 269(43):26739-45, (1994).
Neyts et al., "Therapy and short-term prophylaxis of poxvirus infections: historical background and perspectives", Antivir. Res. 57: 25-33 (2003).
Nibbering et al. "Radiolabelled antimicrobial peptides for imaging of infections: a review," Nucl Med Commun. 19(12):1117-21 (1998).
Nichterlein et al., "Clinafloxacin (CI 960) is Superior to Standard Therapeutics in the Treatment of Murine Listeriosis and Salmonellosis," Zentralbl.Bakteriol. 286: 401-412 (1997).
Nisato, R.E. et al., "Lymphangiogenesis and tumor metastasis", Thromb. Haemost., 90: 591-597 (2003).
Nogrady, T., Medicinal Chemistry A Biochemical Approach, New York: Oxford University Press, pp. 388-392 (1985).
Nolan G.P., et al., "Plasmid mapping computer program," Nucleic Acids Res. 12(1 Pt 2):717-29 (1984).
Norton et al., "Expression of Secreted Platelet-Derived Growth Factor-B by Recombinant Nonreplicating and Noncytopathic Vaccinia Virus," Annals of Surgery 224(4):555-562 (1996).
Noti J.D. et al., "Organization and characterization of genes essential for symbiotic nitrogen fixation from *Bradyrhizobium japonicum* I110," J Bacteriol. 167(3):774-83 (1986).
Noti J.D. et al., "Site-directed Tn5 and transplacement mutagenesis: methods to identify symbiotic nitrogen fixation genes in slow-growing Rhizobium," Methods Enzymol. 154:197-217 (1987).
Nuyts et al., "*Clostridium* spores for tumor-specific drug delivery," Anticancer Drugs. 13(2):115-25 (2002).
Ober, B.T. et al., "Immunogenicity and Safety of Defective Vaccinia Virus Lister:Comparison with Modified Vaccinia Virus Ankara", J. Virol., 76(15): 7713-7723 (2002).
O'Brien et al., "Shiga toxin: biochemistry, genetics, mode of action, and role in pathogenesis," Curr Top Microbiol Immunol. 180:65-94 (1992).
Oertli et al., "Non-replicating recombinant vaccinia virus encoding murine B-7 molecules effective costimulation of naive CD4+ splenocytes in vitro," J. Gen. Virol. 77: 3121-3125 (1996).
Okamoto et al., "Severe impairment of anti-cancer effect of lipoteichoic acid-relatedmolecule isolated from a penicillin-killed *Streptococcus pyogenes* in toll-like receptor 4-deficient mice," International Immunopharmacology 1(9-10): 1789-1795 (2001).

O'Kane et al., "Visualization of Bioluminescence as a Marker of Gene Expression in Rhizobium-Infected Soybean Root Nodules," J. Plant Mol. Biol. 10: 387-399 (1988).
Olsson et al., "Engineering of monomeric bacterial luciferases by fusion of luxA and luxB genes in *Vibrio harveyi*," Gene 81(2):335-47 (1989).
Olsson, O. et al., "The use of the luxA gene of the bacterial luciferase operon as a reporter gene,"Mol Gen Genet. 215(1):1-9 (1988).
O'Mahony et al., "Probiotic impact on microbial flora, inflammation and tumour development in IL-10 knockout mice," Aliment Pharmacol Ther. 15(8):1219-25 (2001).
Overholser et al., "Experimental Bacterial Endocarditis after Dental Extractions in Rats with Periodontitis," J. Infect. Dis. 155(1):107-112 (1987).
Overwijk et al., "Vaccination with a recombinant vaccinia virus enclding a 'self' antigen induces autoimmune vitiligo and tumor cell destruction in mice: Requirement for CD4+ T lymphocytes," Proc. Natl. Acad. Sci. USA 96: 2982-2987 (1999).
Pace, B., "Strep Throat," JAMA, 284(22):2964, (2000).
Padera, T.P. et al., "Lymphatic Metastasis in the Absence of Functional Intratumor Lymphatics", 296: 1883-1886 (2002).
Pak et al., "Cloning of the growth factor gene from vaccinia virus LIVP strain in *Escherichia coli* cells," Mol Gen Mikrobiol Virusol Sep.-Oct.; (9-10):19-21 (1992) ) [article in Russian, English summary on last page of article].
Pan et al., "Regression of Established B16F10 Melanoma with a Recombinant *Listeria monocytogenes* Vaccine," Cancer Research 59:5264-5269 (1999).
Paniacli, D. et al., "Vaccinia virus vectors utilizing the /?-galactosidase assay for rapid selection of recombinant viruses and measurement of gene expression", Gene, 47: 193-199 (1986).
Pardal, R. et al., "Applying the principles of stem-cell biology to cancer," Nature Reviews Cancer, 3: 895-902 (2003).
Parish, C.R., "Cancer immunotherapy: The past, the present and the future", Immunology and Cell Biology, 81: 106-113 (2003).
Parrish et al., "Targeting widespread sites of damage in dystrophic muscle: engrafted macrophages as potential shuttles," Gene Therapy, 3:13-20 (1996).
Patel et al., "A poxvirus-derived vector that directs high levels of expression of cloned genes in mammalian cells," Proc. Natl. Acad. Sci. USA 85: 9431-9435 (1988).
Paul et al., "Redirected cellular cytotoxicity by infection of effector cells with a recombinant vaccinia virus encoding a tumor-specific monoclonal antibody," Cancer Gene Ther. 7(4):615-23 (2000).
Pawelek et al., "Tumor-targeted *Salmonella* as a novel anticancer vector," Cancer Res. 57(20):4537-4544 (1997).
Pawelek, J.M. et al., "Bacteria as tumour-targeting vectors," The Lancet Oncology, 4: 548-556 (2003).
Pearson et al., "Improved tools for biological sequence comparison," Proc. Natl. Acad. Sci. USA 85:2444-2448 (1988).
Pecora, A.L. et al., "Phase I Trial of Intravenous Administration of PV701, an Oncolytic Virus, in Patients With Advanced Solid Cancers", Journal of Clinical Oncology, 20(9): 2251-2266 (2002).
Pekhov AA, Zhukova OS, Ivanova TP, Zanin VA, Dobrynin IaV. [Cytotoxic effect of methioninegamma-lyase on neoplastic cells in culture] Biull Eksp Biol Med. 95(5):87-8 (1983) [Article in Russian; English abstract on last page of article].
Peplinski et al., "In vivo gene therapy of a murine pancreas tumor with recombinant vaccinia virus encoding human interleukin-1beta," Surgery 118:185-191 (1995).
Peplinski, G.R. et al., "Vaccinia Virus for Human Gene Therapy", Surgical Oncology Clinics of North America, 7(3): 575-588 (1998).
Perkus et al. "Recombinant Vaccinia Virus: Immunization Against Multiple Pathogens," Science 229(4717):981-984(1985).
Perkus et al., "Deletion of 55 open reading frames from the termini of vaccinia virus," Virology 180:406-410 (1991).
Pfeifer, A., and I. Verma, "Gene therapy: promises and problems," Annual Review of Genomics and Human Genetics, 2:177-211, (2001).
Pfleidercr et al., "A novel vaccinia virus expression system allowing construction of recombinants without the need for selection markers, plasmids and bacterial hosts," J. General Virology 76:2957-2962 (1995).

(56) References Cited

OTHER PUBLICATIONS

Phillips-Jones, M.K., "Bioluminescence (lux) expression in the anaerobe *Clostridium perfringens*," FEMS Microbiology Letters 106: 265-270 (1993).
Phillips-Jones, M.K., "Use of lux reporter system for monitoring rapid changes in α-toxin gene expression in *Clostridium perfringens* during growth," FEMS Microbiology Letters 188: 29-33 (2000).
Picot et al., "*Pseudomonas fluorescens* as a potential pathogen: adherence to nerve cells," Microbes Infect. 3(12):985-95 (2001).
Pilcher, H., "GM Bug activates cancer drug: Bacteria targets medicine to shrivel mouse tumours," news @ nature.com, Published online: Apr. 22, 2004; http://www.nature.com/news/2004/040419/full/040419-9.html, (accessed on Nov. 18, 2004).
Pinkert et al., "An albumin enhancer located 10 kb upstream functions along with its promoter to direct efficient, liver-specific expression in transgenic mice," Genes & Dev. 1: 268-76 (1987).
Pluccienniczak et al., "Nuceltoide sequence of a cluster and late genes in a conserved segment of the vaccinia virus genome," Nucleic Acids Research 13(3): 993-998 (1985).
Pluen, A. et al., "Role of tumor—host interactions in interstitial diffusion of macromolecules: Cranial vs. subcutaneous tumors", Proc. Natl. Acad. Sci. U.S.A., 98(8): 4628-4633 (2001).
Polverini et al., "Assay and Purification of Naturally Occuring Inhibitor of Angiogenesis," Methods in Enzymology 198:440-450 (1991).
Pongor S. and A.A. Szalay, "Prediction of homology and divergence in the secondary structure of Polypeptides," Proc Natl Acad Sci U S A. 82(2):366-70 (1985).
Pongor S. et al., "Microcomputer programs for prediction and comparative evaluation of protein secondary structure from nucleotide sequence data: application to ribulose-1,5-bisphosphate carboxylase sequences," DNA. 4(4):319-26 (1985).
Poptani et al., "Monitoring thymidine kinase and ganciclovir-induced changes in rat malignant glioma in vivo by nuclear magnetic resonance imaging," Cancer Gene Ther 5(2): 101-109 (1998).
Prasher et al., "Primary structure of the *Aequorea victoria* green-fluorescent protein," Gene 111: 229-233 (1992).
Prasher et al., "Sequence Comparison of Complementary DNAs Encoding Aequorin Isotypes," Biochemistry 26: 1326-1332 (1987).
Prikhod'ko, G. G. and IV Babkin, "5'-variable genome sequence of vaccinia virus LIVP. Possible role of short direct repeats in formation of DNA deletions," Genetika 27(1): 13-26 (1991) [article in Russian, English summary on last page of article].
Prikhod'ko, G. G. et al., "Cloning, Sequencing and Translation Analysis of the Vaccinia Virus LIVP HindIII N Fragment," Genetika 27(6): 955-963 (1991) ) [article in Russian, English summary on last page of article].
Proudfoot, A.E.I. et al., "Strategies for Chemokine Antagonists as Therapeutics", Seminars in Immunology, 15: 57-65 (2003).
Puhlmann et al. "Thymidine kinase-deleted vaccinia virus expressing purine nucleoside phosphorylase as a vector for tumor-directed gene therapy." Hum Gene Ther. 10(4):649-57 (1999).
Puhlmann et al., "Vaccinia virus as a vector for tumor-directed gene therapy: biodistribution of a thymidine kinase-deleted mutant," Cancer Gene Therapy 7(1): 66-73 (2000).
Qazi et al, "Real-time monitoring of intracellular *Staphylococcus aureus* replication," J Bacteriol. 186(4): 1065-1077 (2004).
Qin, H. and S.K. Chatterjee, "Cancer gene therapy using tumor cells infected with recombinant vaccinia virus expressing GM-CSF," Human Gene Ther. 7: 1853-1860 (1996).
Quenelle, D.C. et al., "Efficacy of Multiple- or Single-Dose Cidofovir against Vaccinia and Cowpox Virus Infections in Mice", Antimicrobial Agents and Chemotherapy, 47(10): 3275-3280 (2003).
Ramirez, J.C. et al., "Tissue distribution of the Ankara strain of vaccinia virus (MVA) after mucosal or systemic administration", Arch. Virol., 148: 827-839 (2003).
Rangarajan, A. and R.A. Weinberg, "Comparative biology of mouse versus human cells: modeling human cancer in mice", Nature Reviews Cancer, 3: 952-959 (2003).
Ransohoff, R.M. et al., "Three or more routes for leukocyte migration into the central nervous system", Nat. Rev. Immunol., 3: 569-581 (2003).
Rao et al., "Il-12 is an effective adjuvant to recombinant vaccinia virus-based tumor vaccines," J. Immunol. 156: 3357-3365 (1996).
Reddy et al. "Folate-mediated targeting of therapeutic and imaging agents to cancers," Crit Rev Ther Drug Carrier Syst. 15(6):587-627 (1998).
Rehemtulla, A., et al., "Rapid and quantitative assessment of cancer treatment response using in vivo bioluminescence imaging," Neoplasia, 2(6):491-495, (2000).
Reno, F., "Non-clinical Toxicology", Principles and Practice of Pharmaceutical Medicine, A.J. Fletcher et al.(eds.), ch.6: 55-64 (c2002) John Wiley & Sons Ltd.
Rezmer et al., "Identification and localization of transformed cells in *Agrobacterium tumefaciens*-induced plant tumors," Planta. 209(4):399-405 (1999).
Ribas, A. et al., "Current Developments in Cancer Vaccines and Cellular Immunotherapy", Journal of Clinical Oncology, 21(12): 2415-2432 (2003).
Ring, C.J.A., "Cytolytic viruses as potential anti-cancer agents", J. Gen. Virol., 83: 491-502 (2002).
Rocchetta et al., "Validation of a Noninvasive, Real-Time Imaging Technology Using Bioluminescent *Escherichia coli* in the Neutropenic Mouse Thigh Model of Infection," Antimicrobial Agents and Chemotherapy 45(1): 129-137 (2001).
Rodriguez et al., "Highly attenuated vaccinia virus mutants for the generation of safe recombinant viruses," Proc. Natl. Acad. Sci. USA 86: 1287-1291 (1989).
Rodriguez, J.F. et al., "Expression of the firefly luciferase gene in vaccinia virus: A highly sensitive gene marker to follow virus dissemination in tissues of infected animals," Proc. Natl. Acad. Sci. U.S.A., 85: 1667-1671 (1988).
Rolston et al., "In vitro activity of LY264826, a new glycopeptide antibiotic, against gram-positive bacteria isolated from patients in cancer," Antimicrob. Agents Chemother. 34(11):2137-2141 (1990).
Roseman et al., "The vaccinia virus HindIII fragment: nucleotide sequence of the left 6.2kb," Virology 178: 410-418 (1990).
Roth et al "p53 as a target for cancer vaccines: recombinant canarypox virus vectors expressing p53 protect mice against lethal tumor cell challenge," Proc. Natl. Acad. Sci. USA 93: 4781-4786 (1996).
Rothenberg, M.L. et al., "Improving the evaluation of new cancer treatments: challenges and opportunities," Nat. Rev. Cancer, 3: 303-309 (2003).
Rubanyi et al., "The future of human gene therapy" Molecular Aspects of Medicine 22:113-142 (2001).
Rudinger, "Characteristics of the amino acids as components of a peptide hormone sequence", Peptide Hormones, Parsons, University Park Press, Baltimore, p. 1-7 (1976).
Ruef et al. "Sternal wound infection after heart operations in pediatric patients associated with nasal carriage of *Staphylococcus aureus*" J. of Thoracic and Cardiovascular Surgery 112(3): 681-686 (1996).
Saito, H. and T. Watanabe T., "Effects of a bacteriocin from *Mycobacterium smegmatis* on BALB/3T3 and simian virus 40-transformed BALB/c mouse cells," Microbiol Immunol. 25(1):13-22 (1981).
Sakamoto et al., "Antitumor Effect of Normal Intestinal Microflora on Ehrlich Ascites Tumor," Jpn. J. Cancer Res. (Gann) 79: 109-116 (1988).
Santoro, J. and M.E. Levison, "Rat Model of Experimental Endocarditis," Infect. Immun. 19(3): 915-918 (1978).
Schempp et al., "Inhibition of tumour cell growth by hyperforin, a novel anticancer drug from St. John's wort that acts by induction of apoptosis," Oncogene 21(8):1242-50 (2002).
Schirrmacher et al., "Antitumor effects of Newcastle Disease Virus in vivo: local versus systemic effects," Int J Oncol. 18(5):945-52 (2001).
Schlör et al., "In vivo and in vitro studies on interactions between the components of the hemolysin (HlyA) secretion machinery of *Escherichia coli*," Mol.Gen.Genet. 256: 306-319 (1997).
Schmidt et al. "Generation of effective cancer vaccines genetically engineered to secrete cytokines using adenovirus-enhanced transferrinfection (A VET)," Gene. 190(1):211-6 (1997).

(56) References Cited

OTHER PUBLICATIONS

Schoen et al., "Bacterial delivery of functional messenger RNA to mammalian cells," Cell Microbiol. 7(5):709-24 (2005).
Scholl et al., "Recombinant Vaccinia Virus Encoding Human MUC1 and IL2 as Immunotherapy in Patients with Breast Cancer," J. Immunother 23(5): 570-580 (2000).
Schroder, J.M., "Epithelial antimicrobial peptides: innate local host response elements," Cell Mol Life Sci. 56(1-2):32-46 (1999).
Schuller et al., "Investigation and management of *Clostridium difficile* colonisation in a paediatric oncology unit.," Arch Dis Child. 72(3):219-222 (1995).
Schwartz and Dayhoff, eds., Atlas of Protein Sequence and Structure, National Biomedical Research Foundation, pp. 353-358 (1979).
Sekine et al., "A new morphologically characterized cell wall preparation (whole peptidoglycan) from *Bifidobacterium infantis* with a higher efficacy on the regression of an established tumor in mice," Cancer Res. 45(3):1300-7 (1985).
Sekine et al., "Analysis of antitumor properties of effector cells stimulated with a cell wall preparation (WPG) of *Bifidobacterium infantis*," Biol Pharm Bull. 18(1):148-53 (1995).
Shapiro, D. and A.W. Fox, "Biotechnology Products and Their Development", Principles and Practice of Pharmaceutical Medicine, A.J. Fletcher, et al.(eds.), ch.17: 191-201, c2002 John Wiley & Sons.
Shariatmadari et al., "Improved technique for detection of enhanced green fluorescent protein in transgenic mice," Biotechniques 30:1282-1285 (2001).
Sharma et al., "Death the Fas way: regulation and pathophysiology of CD95 and its ligand," Pharmacol Ther. 88(3):333-47 (2000).
Shata, M.T. et al., "Optimization of recombinant vaccinia-based ELISPOT assay," J. Immunological Methods, 283: 281-289 (2003).
Shchelkunov et al., "The gene encoding the late nonstructural 36K protein of vaccinia virus is essential for virus reproduction," Virus Research 28: 273-283 (1993).
Shenk, T., "Delivery systems for gene therapy: the adenovirus," Stem Cell Biology and Gene Therapy, Quesenberry, P.J. et al. (Eds.), ch.6: pp. 161-178, c1998 Wiley-Liss, Inc.
Shepherd, A.J., "Good Laboratory Practice in the Research and Development Laboratory," Gene Therapy Technologies, Applications and Regulations, A. Meager (Ed.), ch.19: 375-381 (c1999) John Wiley & Sons Ltd.
Shilo, B. and R.A. Weinberg, "DNA sequences homologous to vertebrate oncogenes are conserved in *Drosophila melanogaster*," Proc. Natl. Acad. Sci. USA 78:6789-6792 (1981).
Shimizu et al, "Significance of priming of hosts with virus in the tumor-specific immunotherapy model utilizing virus-reactive helper T cell activity," Nippon Gan Chiryo Gakkai Shi. May 20, 1989;24(5):1007-14. [Article in Japanese; English abstract on second page of article].
Shimizu et al., "Antitumor activity of 2-keto-3-deoxyoctonate-free lipopolysaccharide of *Vibrio anguillarum* in mice," Gann 74(2): 279-284 (1983).
Shimizu et al., "Antitumor activity of marine bacteria, vibrio anguillarum, in mice," Gann 70: 429-433 (1979).
Shimizu et al., "Immunotherapy of tumor-bearing mice utilizing virus help," Cancer Inununol Immunother. 27(3):223-7 (1988).
Shinozaki et al., "Oncolysis of multifocal hepatocellular carcinoma in the rat liver by hepatic artery infusion of vesicular stomatitis virus," Mol. Ther. 9(3): 368-376 (2004).
Silva et al., "Cloning, overexpression, and purification of functional human purine nucleoside phosphorylase," Protein Expr. Purif. 27(1): 158-164 (2003).
Simon et al., "Surveillance for nosocomial and central line-related infections among pediatric hematology-oncology patients," Infect Control Hosp Epidemiol. 21(9):592-6 (2000).
Simonds et al., "Deoxyribonucleic acid hybridization among strains of *Lactobacilli*," J Bacteriol. 107(1):382-4 (1971).
Sinkovics, J. and J. Horvath, "New Developments in the Virus Therapy of Cancer: A Historical Review," Intervirology, 36: 193-214 (1993).
Sinkovics, J.G. and J.C. Horvath, "Newcastle disease virus (NDV): brief history of its oncolytic strains," J. Clin. Virol., 16: 1-15 (2000).
Sinkovics, J.G. and J.C. Horvath, "Virus therapy of human cancers," Melanoma Research, 13: 431-432 (2003).
Sivanandham et al., "Therapeutic effect of a vaccinia colon oncolysate prepared with interleukin-2-gene encoded vaccinia virus studied in a syngeneic CC-36 murine colon hepatic metastasis model" Cancer Immunological Immunotherapy 38:259-264 (1994).
Sivanandham et al., "Colon cancer cell vaccine prepared with replication-deficient vaccinia viruses encoding B7.1 and interleukin-2 induce antitumor response in syngeneic mice," Cancer Immunol Immunother 46(5):261-7 (1998).
Skolnick et al., "From genes to protein structure and function: novel applications of computational approaches in the genomic era" Trends in Biotech. 18:34-39 (2000).
Smee, D.F. and R.W. Sidwell, "A review of compounds exhibiting anti-orthopoxvirus activity in animal models," Antiviral Research, 57: 41-52 (2003).
Smee, D.F. et al., "Effects of cidofovir on the pathogenesis of a lethal vaccinia virus respiratory infection in mice", Antivir. Res., 52: 55-62 (2001).
Smith, G.L. and B. Moss, "Infectious poxvirus vectors have capacity for at least 25000 base pairs of foreign DNA", Gene, 25: 21-28 (1983).
Smith, G.L. et al., "The formation and function of extracellular enveloped vaccinia virus," J. Gen. Virol., 83: 2915-2931 (2002).
Smith, T.F. and M.S.Waterman, "Comparison of biosequences," Adv. Appl. Math. 2:482-489 (1981).
Smyth et al., "Bovine enterovirus as an oncolytic virus: foetal calf serum facilitates its infection of human cells," Int J Mol Med. 10(1):49-53 (2002).
Soby et al., "Catabolite-repressor-like protein regulates the expression of a gene under the control of the *Escherichia coli* lac promoter in the plant pathogen *Xanthomonas campestris* pv. Campestris," Appl Microbiol Biotechnol. 46(5-6):559-61 (1996).
Somia, N. and I.M. Verma, "Gene Therapy: Trial and Tribulations," Nat. Rev. Genet., 1(2): 91-99 (2000).
Sorscher et al., "Tumor cell bystander killing in colonic carcinoma utilizing the *Escherichia coli* DeoD gene to generate toxic purines," Gene Therapy 1(4): 233-238 (1994).
Spencer et al., "Unilateral Transplantation of Human Fetal Mesencephalic Tissue Into the Caudate Nucleus of Patients with Parkinson's Disease", New England Journal of Medicine 327: 1541-1548 (1992).
Spooner et al., "In suicide gene therapy, the site of subcellular localization of the activating enzyme is more important than the rate at which it activates prodrug," Cancer Gene Ther. 7(10):1348-56 (2000).
Steffens et al., "Enhanced green fluorescent protein fusion proteins of herpes simplex virus type 1 thymidine kinase and cytochrome P450 4B1: applications for prodrug-activating gene therapy," Cancer Gene Ther. 7(5):806-12 (2000).
Stehle, G. et al., "Plasma protein (albumin) catabolism by the tumor itself—implications for tumor metabolism and the genesis of cachexia", Critical Reviews in Oncology/Hematology, 26: 77-100 (1997).
Stevens, D.L., "Stretococcal toxic-shock syndrome: spectrum of disease, pathogenesis, and new concepts in treatment," Emerg. Infect. Dis. 1(3): 69-78 (1995).
Stojdl, D.F. et al., "VSV strains with defects in their ability to shutdown innate immunity are potent systemic anti-cancer agents", Cancer Cell, 4:263-275 (2003).
Studeny et al., "Bone Marrow-derived Mesenchymal Stem Cells as Vehicles for Interferon-β Delivery into Tumors," Cancer Research 62: 3603-3608 (2002).
Sudimack et al. "Targeted drug delivery via the folate receptor." Adv Drug Deliv Rev. 41(2):147-62 (2000).
Sugimoto et al., "Gene structures of low-neurovirulent vaccinia virus LC16m0, LC16m8, and their Lister Original (LO) strains," Microbial. Immuol. 29: 421-428 (1985).
Sugimoto, M. and K.Yamanouchi, "Characteristics of an attenuated vaccinia virus strain, LC16m0, and its recombinant virus vaccines," Vaccine 12(8): 675-681 (1994).

(56) References Cited

OTHER PUBLICATIONS

Sutton et al. "In vivo adenovirus-mediated suicide gene therapy of orthotopic bladder cancer." Mol Ther. 2(3):211-7 (2000).
Suvorov et al., "Physical and genetic chromosomal map of an M type 1 strain of *Streptococcus pyogenes*," J. Bacteriol. 178(18): 5546-5549 (1996).
Suzuki et al., "Management of orbital lymphangioma using intralesional injection of OK-432," Br. J. Opthalmol. 84(6): 614-617 (2000).
Suzuki M., Szalay A.A., "Bacterial transformation using temperature-sensitive mutants deficient in peptidoglycan synthesis," Methods Enzymol. 68:331-342 (1979).
Suzuki, S. et al. "Coexpression of the partial androgen receptor enhances the efficacy of prostate-specific antigen promoter-driven suicide gene therapy for prostate cancer cells at low testosterone concentrations," Cancer Research 61(4):1276-1279 (2001).
Symons, J.A. et al., "A study of the vaccinia virus interferon-γ receptor and its contribution to virus virulence", Journal of General Virology, 83: 1953-1964 (2002).
Szalay A.A .et al, "Genetic engineering of halotolerance in microorganisms: a summary," Basic Life Sci. 14:321-32 (1979).
Szalay A.A. et al., "Separation of the complementary strands of DNA fragments on polyacrylamide gels," Nucleic Acids Res. 4(5):1569-78 (1977).
Sze et al., "Dr. Gary J. Becker Young Investigator Award: intraarterial adenovirus for metastatic gastrointestinal cancer: activity, radiographic response, and survival," J. Vasc. Interv. Radiol. 14(3): 279-290 (2003).
Takahashi-Nishimaki et al., "Genetic analysis of vaccinia virus Lister strain and its attenuated mutant LC16m8: production of intermediate variants by homologous recombination," J. Gen. Virol. 68: 2705-2710 (1987).
Tanaka et al, "Preliminary evaluation of intratumoral injection of a *Streptococcus pyogenes* preparation in patients with malignant brain tumors," Cancer 46(7):1688-94 (1980).
Tartaglia et al., "NYVAC: a highly attenuated strain of vaccinia virus," Virology 188(1):217-32 (1992).
Technology Evaluation Center, "Special Report: Vaccines for the Treatment of Malignant Melanoma", TEC Assessment Program, 16(4): 1-46 (2001).
t'Hart, B.A. et al., "Gene thereapy in nonhuman primate models of human autoimmune disease", Gene Therapy, 10: 890-901 (2003).
Thatcher et al., "The potential of acetaminophen as a prodrug in gene-directed enzyme prodrug therapy," Cancer Gene Ther. 7(4):521-5 (2000).
Theuer et al., "A recombinant form of *Pseudomonas* exotoxin directed at the epidermal growth factor receptor that is cytotoxic without requiring proteolytic processing," J.Biol.Chem. 267(24): 16872-16877 (1992).
Theys et al., "Specific targeting of cytosine deaminase to solid tumors by engineered *Clostridium acetobutylicum*," Cancer Gene Ther. 8(4):294-7 (2001).
Theys et al., "Stable *Escherichia coli—Clostridium acetobutylicum* shuttle vector for secretion of murine tumor necrosis factor alpha," Appl Environ Microbiol. 65(10):4295-4300 (1999).
Theys et al., "Tumor-specific gene delivery using genetically engineered bacteria," Curr Gene Ther 3(3): 207-221 (2003).
Tietze et al., "Highly selective glycosylated prodrugs of cytostatic CC-1065 analogues for antibody-directed enzyme tumor therapy," Chembiochem. 2(10):758-65 (2001).
Timiriasova et al., "[Analysis of reporter gene expression at different segments of the vaccinia virus genome]," Mol. Biol. (Mosk.) 27(2): 392-401 (1993) [article in Russian, English abstract on last page of article].
Timiryasova et al., "Construction of recombinant vaccinia viruses using PUV-inactivated virus as a helper," BioTechniques 31: 534-540 (2001).
Timiryasova et al., "Radiation enhances the anti-tumor effects of vaccinia-p53 gene therapy in glioma," Technol Cancer Res Treat. 2(3):223-35 (2003).
Timiryasova, T.M. et al., "Antitumor Effect of Vaccinia Virus in Glioma Model", Oncology Research, 11(3): 133-144 (1999).
Timiryasova, T.M. et al., "Visualization of Vaccinia Virus Infection Using the *Renilla-Luciferase*-GFP Fusion Protein", Bioluminescence & chemiluminescence: Proceedings of the 11th International Symposium on Bioluminescence Chemiluminescence: Asilomar Conference Grounds, Pacific Grove, Monterey, California: Sep. 6-10, 2000 / (eds.): Case, J.F. et al., World Scientific Publishing Co. (c2001), pp. 457-460.
Timiryasova, T.M. et al., "Replication-deficient vaccinia virus gene therapy vector: evaluation of exogenous gene expression mediated by PUV-inactivated virus in glioma cells," Journal of Gene Medicine, 3: 468-477 (2001).
Timiryasova, T.M. et al., "Vaccinia virus-mediated expression of wild-type p53 suppresses glioma cell growth and induces apoptosis." Int J Oncol. 14(5):845-54 (1999).
Timpl, "Antibodies to Collagens and Procollagens," Methods Enzymol. 82: 472-498 (1982).
Tjuvajev et al., "Imaging Adenoviral-mediated Herpes Virus Thymidine Kinase Gene Transfer and Expression In Vivo," Cancer Research 59: 5186-5193 (1999).
Tjuvajev et al., "Imaging Herpes Virus Thymidine Kinase Gene Transfer and Expression by Positron Emission Tomography,"Cancer Res. 58(19): 4333-4341 (1998).
Tjuvajev et al., "Imaging the Expression of Transfected Genes in Vivo," Cancer Res. 55(24): 6126-6132 (1995).
Tjuvajev et al., "Noninvasive Imaging of Herpes Virus Thymidine Kinase Gene Therapy and Expression: A Potential Method for Monitoring Clinical Gene Therapy," Cancer Res 56(18): 40874095 (1996).
Tjuvajev, J. et al., "*Salmonella*-based tumor-targeted cancer therapy: tumor amplified protein expression therapy (TAPET™) for diagnostic imaging," J. Controlled Release, 74: 313-315 (2001).
Toguchi et al., "Suicide Gene Therapy of C6 Glioma Cells Mediated by Replication-Deficient and Replication Competent Vaccinia Viruses," Cancer Gene Therapy 10: S32 (2003) presented at the Eleventh International Conference on Gene Therapy of Cancer, Dec. 12-14, 2002, San Diego California.
Tokugawa et al., "A model system for the continuous production of a heterologous protein using a novel secretion promoting factor which operates in *Escherichia coli*," J.Biotechnol. 37:33-37 (1994).
Tokugawa et al., "A novel protein secretion factor from a Vibrio species which operates in *Escherichia coli*," J.Biotechnol. 35: 69-76 (1994).
Tonetti DA et al "Stable transfection of an estrogen receptor beta cDNA isoform into MDA-MB-231 breast cancer cells," J Steroid Biochem Mol Biol. 87(1):47-55 (2003).
Torrente et al. "Intraarterial injection of muscle-derived CD34+Sca-1+ stem cells restores dystrophin in mdx mice," J. Cell Biol. 152(2):335-348 (2001).
Toso et al, "Phase I study of the intravenous administration of attenuated *Salmonella typhimurium* to patients with metastatic melanoma," J Clin Oncol. 20(1):142-52 (2002).
Toth et al., "An oncolytic adenovirus vector combining enhanced cell-to-cell spreading, mediated by the ADP cytolytic protein, with selective replication in cancer cells with deregulated Wnt signaling," Cancer Research 64: 3638-3644 (2004).
Tresco et al., "Polymer-encapsulated PC12 Cells: Long-Term Survival and Associated Reduction in Lesion-Induced Rotational Behavior," Cell Transplantation 1:255-264 (1992).
Tscharke, D.C. et al., "A model for vaccinia virus pathogenesis and immunity based on intradermal injection of mouse ear pinnae," J. Gen. Virol., 80: 2751-2755 (1999).
Tscharke, D.C. et al., "Dermal infection with vaccinia virus reveals roles for virus proteins not seen using other inoculation routes," Journal of General Virology, 83: 1977-1986 (2002).
Tseng, J.C. et al., "In Vivo Antitumor Activity of Sindbis Viral Vectors," Journal of the National Cancer Institute, 94(23): 1790-1802 (2002).
Tseng, J.C. et al., "Systemic tumor targeting and killing by Sindbis viral vectors," Nat. Biotechnol., 22(1): 70-77 (2004).
Tsung et al. "Gene expression and cytopathic effect of vaccinia virus inactivated by psoralen and long-wave UV light," J. Virol. 70: 165-171 (1996).

(56) References Cited

OTHER PUBLICATIONS

Tsung, K. et al., "Immune Response Against Large Tumors Eradicated by Treatment with Cyclophosphamide and IL-12," J. Immunol., 160: 1369-1377 (1998).
Ullrich C.I. and R. Aloni, "Vascularization is a general requirement for growth of plant and animal tumours," Journal of Experimental Botany 51(353):1951-60 (2000).
Umphress et al., "Vaccinia virus mediated expression of human APC induces apoptosis in colon cancer cells," Transgenics 4:19-33 (2003).
Van Damme et al. "Bone Marrow Stromal Cells as Targets for Gene Therapy," Curr. Gene Ther. 2:195-209 (2002).
Vanderplasschen, A. et al., "Antibodies against vaccinia virus do not neutralize extracellular enveloped virus but prevent virus release from infected cells and comet formation," Journal of General Virology, 78: 2041-2048 (1997).
Vanderplasschen, A. et al., "Intracellular and extracellular vaccinia virions enter cells by different mechanisms," Journal of General Virology, 79: 877-887 (1998).
Varghese, S. and S.D. Rabkin, "Oncolytic herpes simplex virus vectors for cancer virotherapy," Cancer Gene Therapy, 9: 967-978 (2002).
Veijola et al., "Cloning, Baculovirus Expression, and Characterization of the α Subunit of Prolyl 4-Hydroxylase from the nematode *Caenorhabditis elegans*," J. Biol. Chem. 269: 26746-26753 (1994).
Vento, S. and F. Cainelli, "Infections in patients with cancer undergoing chemotherapy: aetiology, prevention, and treatment," Lancet, 4: 595-604 (2003).
Verma et al., "Gene therapy—promises, problems and prospects" Nature 389:239-242 (1997).
Vestweber, D., "Regulation of endothelial cell contacts during leukocyte extravasation," Curr. Opin. Cell Biol., 14: 587-593 (2002).
Vidal et al., "Tissue-specific control elements of the Thy-1 gene," EMBO J. 9(3): 833-840 (1990).
Vile, R. et al., "The oncolytic virotherapy treatment platform for cancer: Unique biological and biosafety points to consider," Cancer Gene Therapy, 9: 1062-1067 (2002).
Vogel, J.R., "Outsourcing Clinical Drug Development Activities to Contract Reseach Organizations (CROs): Critical Success Factors," Principles and Practice of Pharmaceutical Medicine, A.J. Fletcher et al.(eds.), ch.40: 461-482 (c2002) John Wiley & Sons Ltd.
Vogt et al., "Untersuchungen über die Möglichkeit der Tumorlokalisation in vivo auf ser Basis eines szintigrafischer Klostridienstäbchen-Nachweises mit $^{131}$J-markierten Antikörpern und F(ab')$_2$-Antikörperfragmenten," Zeitschrift für Experimentelle Chirurgie 12(4): 209-215 (1979) [article in German, English summary on the last page of the article].
Voisey et al., "Elimination of internal restriction enzyme sites from a bacterial luminescence (luxCDABE) operon," Biotechniques 24(1):56, 58 (1998).
Volm et al., "Enhancement of Incorporation of $^{131}$Iododeoxyuridine into Tumors after Application of *Clostridium oncolyticum* s. butyricum (M 55)," Eur. J. Nucl. Med. 2(2): 117-120 (1977).
Wahl et al., "Improved Radioimaging and Tumor localization with Monoclonal F(ab')$_2$", J. Nucl. Med. 24:316-325 (1983).
Wahl, R., et al., "Improved radioimaging and tumor localization with monoclonal F(ab')$_2$," Journal of Nuclear Medicine, 24:316-325, (1983).
Wallack, M.K. et al., "A Phase III Randomized, Double-Blind, Multiinstitutional Trial of Vaccinia Melanoma Oncolysate-Active Specific Immunotherapy for Patients with Stage II Melanoma," Cancer, 75(1): 34-42 (1995).
Wallack, M.K. et al., "Increased Survival of Patients Treated With a Vaccinia Melanoma Oncolysate Vaccine," Annals of Surgery, 226(2): 198-206 (1997).
Wallack, M.K. et al., "Surgical Adjuvant Active Specific Immunotherapy for Patients with Stage III Melanoma: The Final Analysis of Data From a Phase III, Randomized, Double-Blind, Multicenter Vaccinia Melanoma Oncolysate Trial," J. Am. Coll. Surg., 187(1): 69-79 (1998).

Wang Y. et al., "A study of protein-protein interactions in living cells using luminescence resonance energy transfer (LRET) from *Renilla luciferase* to Aequorea GFP," Mol Gen Genet. 264(5):578-87 (2001).
Wang Y. et al., "*Renilla luciferase*—Aequorea GFP (Ruc-GFP) fusion protein, a novel dual reporter for real-time imaging of gene expression in cell cultures and in live animals," Mol Genet Genomics. 268(2):160-8 (2002).
Wang, Y. et al., "The *Renilla luciferase*-Modified GFP Fusion Protein is Functional in Transformed Cells," Bioluminescence & chemiluminescence: Proceedings of the 9th International Symposium on Bioluminescence Chemiluminescence: Woods Hole, Massachusetts, Oct. 1996 / (eds.) Hastings, J.W. et al., John Wiley & Sons Ltd. (c1997), pp. 419-422.
Warrington et al. "Developing VDEPT for DT-diaphorase (NQO1) using an AAV vector plasmid," Int J Radiat Oncol Biol Phys. 42(4):909-12 (1998).
Watson et al. Molecular Biology of the Gene, 4th Edition, 1987, The Benjamin/Cummings Pub. co., p. 224.
Webley et al., "Measurement of the critical DNA lesions produced by antibody-directed enzyme prodrug therapy (ADEPT) in vitro, in vivo and in clinical material," Br J Cancer. 84(12):1671-6 (2001).
Weedon et al., "Sensitisation of human carcinoma cells to the prodrug CB1954 by adenovirus vector-mediated expression of *E. coli* nitroreductase," Int J. Cancer. 86(6):848-54 (2000).
Wegner et al., "Cis-acting suquences from mouse rDNA promote plasmid DNA amplification and persistence in mouse cells: implication of HMG-I in their function", Nucleic Acids Research 17:9909-9932 (1989).
Wehl et al., "Trends in infection morbidity in a pediatric oncology ward, 1986-1995," Med Pediatr Oncol. 32(5):336-43 (1999).
Weissleder et al. "Drug targeting in magnetic resonance imaging," Magnetic Resonance Quarterly. 8(1):55-63 (1992).
Weissleder et al., "In vivo imaging of tumors with protease-activated near-infrared fluorescent probes," Nature Biotech. 17:375-378 (1999).
Weissleder, T. et al., "In vivo magnetic resonance imaging of transgene expression," Nat. Med. 6(3): 351-354 (2000).
Welling et al "Radiochemical and biological characteristics of $^{99m}$Tc-UBI 29-41 for imaging of bacterial infections." Nucl Med Biol. 29(4):413-22 (2002).
Welling et al "Technetium-99m labelled antimicrobial peptides discriminate between bacterial infections and sterile inflammations." Eur J Nucl Med. 27(3):292-301 (2000).
Weng et al., "HO-1 expression in type II pneumocytes after transpulmonary gene delivery," Am. J. Physiol. Lung Cell Mol. Physol 278:L1273-L1279 (2000).
West et al. "Identification of a somatodendritic targeting signal in the cytoplasmic domain of the transferrin receptor." J Neurosci. 17(16):6038-47 (1997).
Westphal et al., "The nitroreductase/CB1954 combination in Epstein-Barr virus-positive B-cell lines: induction of bystander killing in vitro and in vivo," Cancer Gene Ther. 7(1):97-106 (2000).
Wharton, M. et al., "Recommendations for Using Smallpox Vaccine in a Pre-Event Vaccination Program", MMWR, 52(RR-7): 1-16 (2003).
Whitley, R.J., "Smallpox: a potential agent of bioterrorism", Antiviral Research 57: 7-12 (2003).
Williams J.G. and Szalay A.A., "Stable integration of foreign DNA into the chromosome of the *Cyanobacterium synechococcus* R2," Gene. 24(1):37-51 (1983).
Williams, W Sanders "Southwestern Internal Medicine Conference: Prospects for Gene Therapy of Ischemic Heart Disease" The American Journal of the Medical Sciences 306(2):129-136 (1993).
Winn et al., "Behavioral Recovery following Intrastriatal Implantation of Microencapsulated PC12 Cells," Experimental Neurology 113:322-329 (1991).
Winn, S.R. et al., "Polymer-encapsulated cells genetically modified to secrete human nerve growth factor promote the survival of axotomized septal cholinergic neurons," Proceedings of the National Academy of Sciences U.S.A. , 91:2324-2328 (1994).
Wisher, M., "Biosafety and product release testing issues relevant to replication-competent oncolytic viruses," Cancer Gene Therapy, 9: 1056-1061 (2002).

(56) References Cited

OTHER PUBLICATIONS

Wittrup, D., "Tumor Targeting Theory", IBC's 15th Annual International Antibody Engineering Conference entitled Antibody Engineering: Forging the Future of Antibody Therapeutics, Nov. 30-Dec. 3, 2003—The Paradise Point Resort—San Diego, CA, pp. 1-17.
Wlodaver, C.G. et al., "Laboratory-acquired vaccinia infection," Journal of Clinical Virology, 29(3): 167-170 (2004).
Wolfe et al., "Deletion of the vaccinia virus B5R gene encoding a 42-kilodalton membrane glycoprotein inhibits extracellular virus envelope formation and dissemination," Journal of Virology 67(8): 4732-4741 (1993) and erratum in Journal of Virology, vol. 67, pp. 5709-5711 (1993).
Wollowski et al., "Protective role of probiotics and prebiotics in colon cancer," Am J Clin Nutr. 73 (2 Suppl):451S-455S (2001).
Wong, M.M. and E.N. Fish, Chemokines: attractive mediators of the immune response, Semin. Immunol. 15: 5-14 (2003).
Wu et al., "Biological purging of breast cancer cells using an attenuated replication-competent herpes simplex virus in human hematopoietic stem cell transplantation," Cancer Res. 61(7):3009-15 (2001).
Wu et al., "High resolution microPET imaging of carcino-embryonic antigen-positive xenografts by using a copper-64-labeled engineered antibody fragment," PNAS USA 97(15): 8495-8500 (2000).
Xie et al., "Adenovirus-mediated Tissue-targeted Expression of a Caspase-9-based Artificial Death Switch for the Treatment of Prostate Cancer," Cancer Research 61: 6795-6804 (2001).
Yadav, R. et al., "Migration of leukocytes through the vessel wall and beyond," Thromb. Haemost., 90: 598-606 (2003).
Yamamoto et al., "Production of L-forms of *Streptococcus pyogenes* and their antitumor effects," Jpn J Exp Med. 50(5):383-8 (1980).
Yang et al., "Effects of growth medium composition, iron sources and atmospheric oxygen concentrations on production of luciferase-bacterial magnetic particle complex by a recombinant *Magnetospirillum magneticum* AMB-1," Enzyme Microb. Technol. 29: 13-19 (2001).
Yang et al., "Visualizing gene expression by whole-body fluorescence imaging," PNAS 97(22): 12278-12282 (2000).
Yang et al., "Whole-body optical imaging of green fluorescent protein-expressing tumors and metastases," Proc. Natl. Acad. Sci. USA 97(3):1206-1211 (2000).
Yansura, D.G. and D.J. Henner, "Use of the *Escherichia coli* lac repressor and operator to control gene expression in *Bacillus subtilis*," Proc. Natl. Acad. Sci USA 81: 439-443 (1984).
Yazawa et al., "*Bifidobacterium longum* as a delivery system for cancer gene therapy: Selective localization and growth in hypoxic tumors," Cancer Gene Ther. 7(2):269-74 (2000).
Yazawa et al., *Bifidobacterium longum* as a delivery system for gene therapy of chemically induced rat mammary tumors. Breast Cancer Res Treat. 66(2):165-70 (2001).
Yazawa et al., "Current progress in suicide gene therapy for cancer," World J. Surg 26(7): 783-789 (2002).
Yong et al., . Visualization of tumors and metastases in live animals with bacteria and vaccinia virus encoding light-emitting proteins, Nature Biotechnology 22(3):313-320 (2004).
Yoshida et al., "Cell growth-inhibitory action of SAGP, an antitumor glycoprotein from *Streptococcus pyogenes* (Su strain)," Jpn. J. Pharmacol. 45(2): 143-147 (1987).
Yoshida et al., "Characterization of a streptococcal antitumor glycoprotein (SAGP)," Life Sciences 62(12): 1043-1053 (1998).
Yoshida et al., "Growth-inhibitory effect of streptococcal antitumor glycoprotein on human epidermoid carcinoma A431 cells: involvement of dephosphorylation of epidermal growth factor receptor," Cancer Research 61(16): 6151-6157 (2001).
Yu Y.A. et al., "A *Renilla luciferase*-Aequorea GFP (ruc-gfp) fusion gene construct permits real-time detection of promoter activation by exogenously administered mifepristone in vivo," Mol Genet Genomics. 268(2):169-78 (2002).
Yu Y.A. et al., "Optical imaging: bacteria, viruses, and mammalian cells encoding light-emitting proteins reveal the locations of primary tumors and metastases in animals," Anal Bioanal Chem. 377(6):964-72 (2003).
Yu Y.A., "Visualization of molecular and cellular events with green fluorescent proteins in developing embryos: a review," Luminescence. 18(1):1-18 (2003) Erratum in: Luminescence. Jul.-Aug. 2003; 18(4):243.
Yu, Y.A. et al. "Visualization of tumors and metastases in live animals with bacteria and vaccinia virus encoding light-emitting proteins," Nat Biotech. 22(3): 313-320 (2004).
Yun a.C. et al. "Nitrogenase promoter-lacZ fusion studies of essential nitrogen fixation genes in *Bradyrhizobium japonicum* I110," J Bacteriol. 167(3):784-91 (1986).
Zambryski et al., "Tumor induction by *Agrobacterium tumefaciens*: analysis of the boundaries of T-DNA," J Mol Appl Genet. 1(4):361-70 (1982).
Zamir et al., "Stable chromosomal integration of the entire nitrogen fixation gene cluster from *Klebsiella pneumoniae* in yeast," Proc Natl Acad Sci U S A. 78(6):3496-500 (1981).
Zaucha, G.M. et al., "The Pathology of Experimental Aerosolized Monkeypox Virus Infection in Cynomolgus Monkeys (*Macaca fascicularis*)," Lab. Invest., 81: 1581-1600 (2001).
Zeh, H.J. and D.L. Bartlett, "Development of a replication-selective, oncolytic poxvirus for the treatment of human cancers," Cancer Gene Therapy, 9: 1001-1012 (2002).
Zhang et al., "Urothelium-specific Expression of an Oncogene in Transgenic Mice Induced the Formation of Carcinoma in Situ and Invasive Transitional Cell Carcinoma," Cancer Res.59: 3512-3517 (1999).
Zhao et al., "Spatial-temporal imaging of bacterial infection and antibiotic response in intact animals," Proceeding of the National Academy of Sciences 98(17): 9814-9818 (2001).
Zheng et al., "Tumor amplified protein expression therapy: *Salmonella* as a tumor-selective protein delivery vector," Oncology Research 12(3):127-135 (2000).
Zhu et al., "Smad3 Mutant Mice Develop Metastatic Colorectal Cancer," Cell 94: 703-714 (1998).
Zimmermann et al., "Independent regulatory elements in the nestin gene direct transgene expression to neural stem cells," Neuron 12: 11-24 (1994).
Zinkernagel, R.M., "Uncertainties—discrepancies in immunology", Immunological Reviews, 185: 103-125 (2002).
Zinn et al. "Noninvasive monitoring of gene transfer using a reporter receptor imaged with a high-affinity peptide radiolabeled with 99mTc or 188Re," J Nucl Med. May 2000;41(5):887-95.
Zinn et al., "Simulataneous evaluation of dual gene transfer to adherent cells by gamma-ray imaging," Nuclear Medicine and Biology 28(2):135-144 (2001).
Zinoviev et al., "Identification of the gene encoding vaccinia virus immunodominant protein p35," Gene 147: 209-214 (1994).
Zolotukhin et al., "A "Humanized" Green Fluorescent Protein cDNA adapted for high-level expression in mammalian cells," J. Virol. 70:4646-4654 (1996).
zur Hausen, H., Papillomaviruses and cancer: from basic studies to clinical application. Nature Reviews Cancer 2(5):342-50 (2002).
First complaint, filed in the Superior Court for the State of California, County of Los Angeles, dated Dec. 21, 2005 (Case No. BC344912) *Genelux Corporation*, a Delaware corporation (Plaintiff) vs. *Dr. Bernard Huber*, an individual; Patentanwälte Huber & Schüssler, a partnership under the Code Gesellschaft des Burgerlichen Rechts; Dr. Gerd Stehle, an individual; and Does I through 10, inclusive (Defendants).
Stipulation and Order of Dismissal. Case No. CV06-1462 AG(FMOx).
Petition for Retroactive Grant of Foreign Filing License, filed on May 9, 2008, in connection with U.S. Appl. No. 10/872,156.
Joint Stipulation Regarding Defendants' Motion to Compel: (I) Deposition Testimony on Identified Subjects Pursuant to Rule 30(B)(6), and (2) The Production of Documents [Local Rule 37-2.1] . Case No. CV06-1462 AG (FMOx).
Notice of Removal of Action Under 28 U.S.C. 1441 (Diversity) Case No. CV06-1462 AG (FMOx), *Genelux Corporation*, a Delaware corporation(Plaintiff) vs. *Dr. Bernard Huber*, an individual; Patentanwälte Huber & Schüssler, a partnership under the Code Gesellschaft des Burgerlichen Rechts; Dr. Gerd Stehle, an individual; and Does 1 through 10, inclusive (Defendants).

(56) References Cited

OTHER PUBLICATIONS

Answer and Counterclaims for Fraud, Negligent Misrepresentation, Breach of Fiduciary Duty; Breach of Contract; and Indemnity. Case No. CV06-1462 AG (FMOx), *Genelux Corporation*, a Delaware corporation (Plaintiff) vs. *Dr. Bernard Huber*, an individual; Patentanwälte Huber & Schüssler, a partnership under the Code Gesellschaft des Burgerlichen Rechts; Dr. Gerd Stehle, an individual; and Does 1 through 10, inclusive (Defendants); Dr. Bernard Huber, an individual; Patentanwälte Huber & Schüssler, a partnership under the Code Gesellschaft des Burgerlichen Rechts; Dr. Gerd Stehle, an individual (Counterclaimants) vs. Genelux Corporation, a Delaware corporation, Ronald Simus, an individual, David Wood, an individual, and Aladar A. Szalay, an individual (Counterdefendants).
Report of Parties' Planning Meeting for Scheduling Conference. Case No. CV06-1462 AG (FMOx).
Notice of Motion and Motion to Compel Further Responses by Defendant/Counterclaimant Dr. Bernard Huber to Interrogatories; Joint Stipulation of the Parties; Declaration of Howard M. Loeb. Case No. CV06-1462 AG (FMOx).
Order Regarding Discovery Motions. Case No. CV06-1462 AG (FMOx).
Declaration of Paula K. Schoeneck.
Notice of Motion and Motion to Dismiss Counterclaimants Huber and Stehle's Fourth Cause of Action for Failure to State a Claim upon which Relief can be Granted; Memorandum of Points and Authorities; Declaration Pursuant to Local Rule 7-3. Case No. CV06-1462 GHK (FMOx).
Counterclaimants' Opposition to Counterdefendant Genelux's Motion to Dismiss. Case No. CV06-1462 GHK (FMOx).
Reply to Opposition to Motion to Dismiss Counterclaimants Huber and Stehle's Fourth Cause of Action for Failure to State a Claim upon which Relief can be Granted. Case No. CV06-1462 GHK (FMOx).
Court Order granting Genelux's motion to dismiss. Case No. CV06-1462 GHK (FMOx).
First Amended Counterclaims for Fraud; Negligent Misrepresentation, Breach of Fiduciary Duty; Breach of Contract; Breach of the Implied Covenant of Good Faith and Fair Dealing; and Indemnity. Case No. CV06-1462 GHK (FMOx).
Notice of Motion and Motion to Dismiss Counterclaimants Huber and Stehle's Seventh Cause of Action for Failure to State a Claim Upon Which Relief Can be Granted; Memorandum of Points and Authorities; Declaration Pursuant to Local Rule 7-3. Case No. CV06-1462 GHK (FMOx).
Counterclaimants' Opposition to Motion to Dismiss Seventh Cause of Action. Case No. CV06-1462 GHK (FMOx).
Reply to Opposition to Motion to Dismiss Counterclaimants Huber and Stehle's Seventh Cause of Action for Failure to State a Claim Upon Which Relief can be Granted Case No. CV06-1462 AG(FMOx).
(In Chambers) Order Denying Motion to Dismiss Counterclaimants' Seventh Cause of Action. Case No. CV06-1462 AG(FMOx).
Reply to First Amended Counterclaims. Case No. CV06-1462 AG(FMOx).
Letter, dated Jun. 3, 2004, from Istvan Fodor and Tatyana Timiryasova to the Editorial Office of *Analytical and Bioanalytical Chemisty*.
Letter, dated Jun. 3, 2004, from Istvan Fodor and Tatyana Timiryasova, to the *Editor of Nature Biotechnology*.
Letter, dated Feb. 23, 2004, from Aladar A. Szalay, Yong Aa. Yu, Shahrokh Shabahang, Richard E. Beltz, and Qian Zhang to Istvan Fodor.
E-Mail, dated Jul. 27, 2004, from Andrew Marshall to Aladar A. Szalay.
E-Mail, dated Jul. 28, 2004, from Aladar A. Szalay to Andrew Marshall.
Letter, dated May 16, 2004, from Richard E. Beltz, to Dr. Istvan Fodor.
"Detection of tumors in live animal models: localization of tumor development by light emission and tumor regression by light extinction," *Invention Disclosure Form LL64* (Filed with the Intellectual Property Office at Loma Linda University in 2001).
"Detection of tumors in live animal models: localization of tumor development by light emission and tumor regression by light extinction," *Invention Disclosure Form LL72* (Filed with the Intellectual Property Office at Loma Linda University in 2001).
Letter from Barry L. Taylor, Vice Chancellor for Research Affairs, Loma Linda University, to Tatana Timiryasova, dated Oct. 30, 2001.
Office Action, issued Nov. 26, 2006, in connection with U.S. Appl. No. 10/866,606.
Office Action, issued Aug. 1, 2007, in connection with U.S. Appl. No. 10/866,606.
Translation of Office Action, issued Mar. 24, 2008, in connection with corresponding Japanese Patent Application No. 2003-519509.
Kelly et al. Novel oncolytic agent GLV-1h68 is effective against malignant pleural mesothelioma. *Hum Gene Ther*. 19(8):774-82 (2008).
Kelly et al., "Real-time intraoperative detection of melanoma lymph node metastases using recombinant vaccinia virus GLV-1h68 in an immunocompetent animal model" Int. J. Cancer (accessed on Oct. 21, 2008) (30 pages) (2008).
Li et al., Oncolytic Vaccinia Virotherapy of Anaplastic Thyroid Cancer In Vivo. J Clin Endocrinol Metab (accessed on Oct. 21, 2008) (16 pages) (2008).
Lin S-F, Yu Z, Riedl C, et al. "Treatment of anaplastic thyroid carcinoma in vitro with a mutant vaccinia virus." Surgery 2007;142(6):976-83.
Lin SF, Price DL, Chen CH, et al. Oncolytic Vaccinia Virotherapy of Anaplastic Thyroid Cancer In Vivo. *J Clin Endocrinol Metab* (accessed on Oct. 21, 2008) (16 pages) (2008).
Karupiah et al., "Vaccinia virus-mediated damage of murine ovaries and protection by virus-expressed interleukin-2," Immunol. Cell Biol. 68: 325-333 (1990).
Fisher, K., "Striking out at disseminated metastases: the systemic delivery of oncolytic viruses," Curr. Opin. Mol. Ther. 8(4):301-313 (2006).
Genbank Accession No. M57977 (accessed at www.ncbi.nlm.nih.gov/entrez/viewer.fcgi?db=nuccore&id=335694) (11 pgs.) (accessed on Sep. 12, 2008).
Hung et al., "Vaccinia virus preferentially infects and controls human and murine ovarian tumors in mice," Gene Ther. 14:20-29 (2007).
Peplinsky et al., "In vivo murine tumor gene delivery and expression by systemic recombinant vaccinia virus encoding interleukin-1 beta," Cancer J. Sci. Am. 2(1):21-27 (1996) [abstract].
Sandman et al., "Rapid fluorescence-based reporter-gene assays to evaluate the cytotoxicity and antitumor drug potential of platinum complexes," Chem. Biol. 6:541-551 (1999).
Zhu et al., "A cellular protein binds vaccinia virus late promoters and activates transcription in vitro," J. Virol. 72(5):3893-3899 (1998).
Office Action, issued Feb. 3, 2010, in connection with U.S. Appl. No. 10/485,179.
Office Action, issued May 18, 2010, in connection with U.S. Appl. No. 11/982,035.
Office Action, issued May 18, 2010, in connection with U.S. Appl. No. 11/982,102.
Office Action, issued May 19, 2010, in connection with U.S. Appl. No. 11/982,040.
Examination Report, issued May 28, 2010, in connection with Canadian Patent Application Serial No. 2,456,055.
Office Action, issued Oct. 21, 2010, in connection with U.S. Appl. No. 10/485,179.
Office Action, issued Nov. 2, 2010, in connection with U.S. Appl. No. 10/866,606.
Gentschev et al., "Regression of human prostate tumors and metastases in nude mice following treatment with the recombinant oncolytic vaccinia virus GLV-1h68," J. Biomed. Biotechnol. 2010:1-11 (2010).
Zhang et al., "The highly attenuated oncolytic recombinant vaccinia virus GLV-1h68: comparitive genomic features and the contribution of F14.5L inactivation," Mol. Genet. Genomics 282(4):417-435 (2009).
Singapore Examination Report, issued Dec. 7, 2010, in connection with Singapore Patent Application No. 200602906-0.

(56) References Cited

OTHER PUBLICATIONS

Advani et al., "Radiotargeting systemically administered oncolytic vaccinia virus to preferentially replicate in radiated gliomas," Abstract, ASTRO 53rd Annual Meeting, Miami Beach, FL, Oct. 2-6, 2011 [1 page].

Gentschev et al., "Significant growth inhibition of canine mammary carcinoma xenografts following treatment with oncolytic vaccinia virus GLV-1h68," J. Oncol. 2010:1-10 (2010).

Gentschev et al., "Efficient colonization and therapy of human hepatocellular carcinoma (HCC) using the oncolytic vaccinia virus strain GLV-1h68," PLoS One. 6(7): 1-9 (2011).

Hoffman et al., "Vaccinia virus GLV-1h237 carrying a Walker A motif mutation of mouse Cdc6 protein enhances human breast tumor therapy in mouse xenografts," Int. J. Oncol. 38(3):871-878 (2011) [Published online Jan. 18, 2011].

Seubert et al., "Enhanced tumor therapy using vaccinia virus strain GLV-1h68 in combination with a β-galactosidase-activatable prodrug seco-analog of duocarmycin SA," Cancer Gene Ther. 18:42-52 (2011).

Examination Report, issued Dec. 7, 2010, in connection with corresponding Singapore Patent Application Serial No. 200602906-0 [9 pages].

Office Action, issued Jul. 13, 2011, in connection with corresponding U.S. Appl. No. 10/866,606 [9 pages].

Office Action, issued Jul. 20, 2011, in connection with corresponding U.S. Appl. No. 10/485,179 [25 pages].

Bischoff et al., "An adenovirus mutant that replicates selectively in p53-deficient human tumor cells," Science, 274(5286):373-376 (1996).

Buller et al., In: "Vaccinia Viruses as Vectors for Vaccine Antigens," New York: Elsevier, Quinnan, G.V. ed.,pp. 37-46 (1985).

Casado et al, "Strategies to accomplish targeted expression of transgenes in ovarian cancer for molecular therapeutic applications," Clin. Cancer Res. 7(8):2496-2504 (2001).

Certified English Translation of Chernos et al., "Tests for safety, 'Take'—Rate, Reactogenicity and Antigenic Properties of a Live Recombinant Smallpox-Hepatitis B Vaccine in Volunteers," Vopr. Virusol. (Moscow) 35:132-135 (1990).

Chemos et al., "Tests for safety, 'Take' - Rate, Reactogenicity and Antigenic Properties of a Live Recombinant Smallpox-Hepatitis B Vaccine in Volunteers", Vopr. Virusol. (Moscow) 35:132-135 (1990).

Coupar et al., "Insertion sites for recombinant vaccinia virus construction: effects on expression of a foreign protein," J. Gen. Virol. 81:431-439 (2000).

Demkowicz et al., "Human cytotoxic T-cell memory: long-lived responses to vaccinia virus," J. Virol. 70(4):2627-2631 (1996).

DiStefano et al., "Viral-induced remission in chronic lymphocytic leukemia?" Arch. Intern. Med. 139(8):946 (1979).

Enserink, "Treating vaccine reactions: two lifelines, but no guarantees," Science, 298(5602):2313 (2002).

Etoh et al., "Oncolytic viral therapy for human pancreatic cancer cells by reovirus," Clin. Cancer Res. 9:1218-1223 (2003).

Galmiche et al., "Expression of a functional single chain antibody on the surface of extracellular enveloped vaccinia virus as a step towards selective tumour cell targeting," J. Gen. Virol. 78:3019-3027 (1997).

Hamid et al., "Phase II trial of intravenous Cl-1042 in patients with metastatic colorectal cancer," J. Clin. Oncol. 21(8):1498-1504 (2003).

Hoshi et al., "Antitumoral effects of defective herpes simplex virus-mediated transfer of tissue inhibitor of metalloproteinases-2 gene in malignant glioma U87 in vitro: consequences for anticancer gene therapy," Cancer Gene Ther. 7(5):799-805 (2000).

Lane et al., "Complications of smallpox vaccination, 1968: results of ten statewide surveys," J. Infect. Dis. 122:303-309 (1970).

Lane et al., "Complications of smallpox vaccinations, 1968: national surveillance in the United States," New Engl. J. Med. 281:1201-1208 (1969).

Meighen et al., "Molecular biology of bacterial bioluminescence," Microbiol. Rev. 55(1):123-142 (1991).

Orkin et al., "Report and recommendations of the panel to assess the NIH investment in research on gene therapy," (1995).

Payne, "Significance of extracellular enveloped virus in the in vitro and in vivo dissemination of vaccinia," J. Gen. Virol. 50(1):89-100 (1980).

Sanz et al., "Identification of a transcription factor, encoded by two vaccinia virus early genes, that regulates the intermediate stage of viral gene expression," Proc. Natl. Acad. Sci. 96(6):2692-2697 (1999).

Sidwell et al., "In vivo antiviral properties of biologically active compounds," Appl. Microbiol. 16(2):370-392 (1968).

Smith et al., "Oncolytic viruses as novel anticancer agents: turning one scourge against another," Exp. Opin. Invest. Drugs, 9(2):311-327 (2000).

Stienlauf et al., "Kinetics of formation of neutralizing antibodies against vaccinia virus following re-vaccination," Vaccine, 17:201-204 (1999).

Taubes et al., "Firefly gene lights up lab animals inside out," Science, 276:1993 (1997).

Tjuvajev et al., "Comparison of radiolabeled nucleoside probes (FIAU, FHBG, and FHPG) for PET imaging of HSV1-tk gene expression," J. Nucl. Med. 43:1072-83 (2002).

Vanderplasschen et al., "A novel virus binding assay using confocal microscopy: demonstration that the intracellular and extracellular vaccinia virions bind to different cellular receptors," J. Virol. 71(5):4032-41(1997).

Weir et al., "Determination of the transcriptional regulatory region of a vaccinia virus late gene," J. Virol. 61(1):75-80 (1987).

Yettra, "Remission of chronic lymphocytic leukemia after smallpox vaccination," Arch. Intern. Med. 139(5):603 (1979).

Translation, dated Apr. 4, 2006, of Office Action, issued in connection with Chinese Patent Application No. 02819339.3.

Examination Report, issued Feb. 9, 2006, in connection with Australian Patent Application No. 2002355500.

Summons to Oral Proceedings, issued Apr. 11, 2006, in connection with European Patent Application No. 02794632.6.

Translation of Office Action, issued Nov. 15, 2007, in connection with Israeli Patent Application No. 160,052.

Examination Report, issued Mar. 14, 2006, in connection with New Zealand patent Application No. 530818.

Examination Report, issued Jun. 7, 2006, in connection with New Zealand patent Application No. 530818.

Examination Report, issued Jun. 9, 2006, in connection with Turkish patent Application No. TR 2004/00149.

Office Action, issued Jun. 1, 2006, in connection with U.S. Appl. No. 10/485,179.

Office Action, issued Feb. 27, 2007, in connection with U.S. Appl. No. 10/485,179.

Office Action, issued Nov. 19, 2007, in connection with U.S. Appl. No. 10/485,179.

Office Action, issued Oct. 4, 2007, in connection with Canadian patent Application No. 2,456,055.

Examination Report, issued Jun. 22, 2007, in connection with European patent Application No. 03735553.4.

MedicineNet.com, definition of Tumor www.medterms.com/script/main/art.asp?articlekey=5863 (Accessed on May 30, 2007).

Letter/Written Disclosure of the Information Disclosure Statement for the above referenced application (U.S. Appl. No. 11/981,976) mailed on Feb. 21, 2012, 3 pages.

Advani et al., "Oncolytic vaccinia virus encoding an anti-VEGF antibody improves the therapeutic efficacy of fractionated radiotherapy in lung tumor xenografts," Abstract, ASTRO 53rd Annual Meeting, Miami Beach, FL, Oct. 2-6, 2011, 2 pages.

Advani et al., "Oncolytic vaccinia virus encoding an anti-VEGF antibody improves the therapeutic efficacy of fractionated radiotherapy in tumor xenografts," poster, ASTRO 53rd Annual Meeting, Miami Beach, FL, Oct. 2-6, 2011, 1 page.

Ascierto et al., "Permissivity of the NCI-60 cancer cell lines to oncolytic vaccinia virus GLV-1H68," BMC Cancer 11(1): [epub ahead of print] (2011), 27 pages.

Browne et al., "Cancer screening by systemic administration of a gene delivery vector encoding tumor-selective secretable biomarker expression," PLoS One 6:(5):e19530 (2011), 9 pages.

(56) References Cited

OTHER PUBLICATIONS

Chen et al., "Replication efficiency of oncolytic vaccinia virus in cell cultures prognosticates the virulence and antitumor efficacy in mice," J. Translational Med. 9(1):164 epub date Sep. 27, 2011, 11 pages.
Corral et al., "Phase I clinical trial of genetically modified and oncolytic vaccinia virus GL-ONC1 with green fluorescent protein imaging," 7th NCRI Cancer Conference, Liverpool, UK. Nov. 6-9, 2011, poster, 1 page.
Corral et al., "Phase I clinical trial of genetically modified and oncolytic vaccinia virus GL-ONC1 with green fluorescent protein imaging," 7th NCRI Cancer Conference, Liverpool, UK. Nov. 6-9, 2011, abstract, 2 pages.
Haddad et al., "A novel genetically modified oncolytic vaccinia virus is effective against a wide range of human cancers," Annals of Surgical Oncology, (2011) [epub ahead of print Jan. 19, 2012] DOI: 10.1245/s10434-011-2198-x, 10 pages.
Harrington, K., "GL-ONC1 phase I trial at Royal Marsden Hospital," Roche-Genelux Meeting, Penzberg, Germany, Sep. 19, 2011 [poster], 25 pages.
Hess et al., "Bacterial glucuronidase as general marker for oncolytic virotherapy or other biological therapies," J. Translational Medicine 9:172, 12 pages.
Pedersen et al., "A phase I clinical trial of genetically modified and imageable oncolytic vaccinia virus GL-ONC1 with clinical green fluorescent protein (GFP) imaging," J. Clin. Oncol 29: 2011, [Abstract No. 2577] ASCO Annual Meeting, Jun. 3-7, 2011, 2 pages.
Pedersen et al., "A phase I clinical trial of genetically modified and imageable oncolytic vaccinia virus GL-ONC1 with clinical green fluorescent protein (GFP) imaging," J. Clin. Oncol 29: 2011, [Poster] ASCO Annual Meeting, Jun. 3-7, 2011, 1 page.
Sturm et al., "Functional hyper-IL-6 from vaccinia virus-colonized tumors triggers platelet formation and helps to alleviate toxicity of mitomycin C enhanced virus therapy," J. Trans!. Med. 10(1):9 [epub ahead of print, Jan. 11, 2012], 40 pages.
Notice of Allowance, issued Jun. 10, 2011, in connection with corresponding Canadian Patent Application Serial No. 2,456,055, 6 pages.
Instructions for Response to Office dated Sep. 16, 2011, mailed Jan. 18, 2012, in connection with corresponding Chinese Patent Application No. 200810130048.9, 8 pages.
Examination Report, issued Dec. 21, 2011, in connection with corresponding Israeli Patent Application No. 160052, 4 pages.
Instructions for Response to Official Action dated Nov. 21, 2011, mailed Jan. 31, 2012, in connection with corresponding Israeli Patent Application No. 160052, 17 pages.
Letter/Written Disclosure of the Information Disclosure Statement for the above referenced application (U.S. Appl. No. 11/981,976) mailed on Mar. 13, 2008, 6 pages.
Letter/Written Disclosure of the Information Disclosure Statement for the above referenced application (U.S. Appl. No. 11/981,976) mailed on Oct. 15, 2009, 4 pages.
Letter/Written Disclosure of the Information Disclosure Statement for the above referenced application (U.S. Appl. No. 11/981,976) mailed on Nov. 12, 1009, 3 pages.
Translation, dated Apr. 4, 2006, of Office Action, issued in connection with Chinese Patent Application No. 02819339.3, 4 pages.
Examination Report, issued Feb. 9, 2006, in connection with Australian Patent Application No. 2002355500, 2 pages.
Summons to Oral Proceedings, issued Apr. 11, 2006, in connection with European Patent Application No. 02794632.6, 10 pages.
Translation of Office Action, issued Nov. 15, 2007, in connection with Israeli Patent Application No. 160,052, 6 pages.
Examination Report, issued Mar. 14, 2006, in connection with New Zealand patent Application No. 530818, 2 pages.
Examination Report, issued Jun. 7, 2006, in connection with New Zealand patent Application No. 530818, 2 pages.
Examination Report, issued Jun. 9, 2006, in connection with Turkish patent Application No. TR 2004/00149, 4 pages.
Office Action, issued Jun. 1, 2006, in connection with U.S. Appl. No. 10/485,179, 16 pages.
Office Action, issued Feb. 27, 2007, in connection with U.S. Appl. No. 10/485,179, 33 pages.
Office Action, issued Nov. 19, 2007, in connection with U.S. Appl. No. 10/485,179, 29 pages.
Office Action, issued Oct. 4, 2007, in connection with Canadian patent Application No. 2,456,055, 5 pages.
Examination Report, issued Jun. 22, 2007, in connection with European patent Application No. 03735553.4, 5 pages.
Massoud et al., "Molecular imaging in living subjects: seeing fundamental biological processes in a new light", Genes & Develop. 17:545-580 (2003).
MedicineNet.com, "Definition of tumor," [retrieved on May 30, 2007] Retrieved from:<URL:medterms.com/script/main/art.asp?articlekey=5863 [2 pages].
Office Action, issued Apr. 9, 2009, in connection with U.S. Appl. No. 10/485,179, 43 pages.
"Safety Study of GL-ONC1, an Oncolytic Virus, in Patients with Advanced Solid Tumors", www.clinicaltrials.gov/ct2/show/NCT00794131?term—genelux&rank=1 (accessed on Dec. 2, 2008, 5 pages).
Brown, "Killer into cure—oncolytic viruses," Microbiology Today 56:128-131 (2005).
Chang et al., "Targeting vaccinia to solid tumors with local hyperthermia," Hum. Gene Ther. 16:435-444 (2005).
Denes et al. "Attenuation of a vaccine strain of vaccinia virus via inactivation of interferon viroceptor," J. Gene Med. 8(7):814-823 (2006).
Everts et al., "Replication-selective oncolytic viruses in the treatment of cancer," Cancer Gene Ther. 12:141-161 (2005).
Frentzen et al., "Anti-VEGF single chain antibody GLAF-1 encoded by oncolytic vaccinia virus significantly enhances antitumor therapy," Proc. Natl. Acad. Sci. USA 106(31):12915-12920 (2009).
Gentschev et al., "Use of an oncolytic vaccinia virus for treatment of canine breast cancer in nude mice: preclinical development of a therapeutic agent," Cancer Gene Ther. 16(4):320-328 (2009).
Hermiston et al., "Genetically based therapeutics for cancer: similarities and contrasts with traditional drug discovery and development," Mol. Ther. 11(4):496-507 (2005).
Li et al., "Oncolytic virotherapy as personalized cancer vaccine," Int. J. Cancer 123:493-499 (2008).
Martinez et al., "Specific antibody to *Cryptococcus neoformans* glucurunoxylomannan antagonizes antiftingal drug action against cryptococcal biofilms in vitro," J. Infect. Diseases 194:261-266 (2006).
Naik et al., "Intravenous and isolated limb perfusion delivery of wild type and a tumor-selective replicating mutant vaccinia virus in non-human primates," Hum. Gene Ther. 17:1-15 (2006).
Okuse et al., "Enhancement of antiviral activity against hepatitis C virus in vitro by interferon combination therapy," Antiviral Res. 65:23-34 (2005).
Sui et al., "Cell cycle-dependent antagonistic interactions between paclitaxel and gamma-radiation in combination therapy," Clin. Canc. Res. 10:4848-4857 (2004).
Thorne et al., "Vaccinia virus and oncolytic virotherapy of cancer," Curr. Opin. Mol Ther. 7(4):359- 365 (2005).
Tysome et al., "Lister strain of vaccinia virus armed with endostatin-angiostatin fusion gene as a novel therapeutic agent for human pancreatic cancer," Gene Ther. (2009) (Epub ahead of print).
Westphal et al., "Containment of tumor-colonizing bacteria by host neutrophils," Cancer Res. 68(8):2952-2960 (2008).
Worschech et al., "The immunologic aspects of poxvirus oncolytic therapy," Cancer Immunol. Immunother. 58(9):1355-1362 (2009).
Worschech et al., "Systemic treatment of xenografts with vaccinia virus GLV1h68 reveals the immunologic facet of oncolytic therapy," BMC Genomics 10:301 (2009).
Xiong et al., "Cell cycle dependent antagonistic interactions between paclitaxel and carboplatin in combination therapy" Cancer Biol. Ther. 6(7):1067-1073 (2007).
Yu et al., "Regression of human pancreatic tumor xenografts in mice after a single systemic injection of recombinant vaccinia virus GLV-1h68," Mol.Cancer Ther. 8:141-151 (2009).
Yu et al., "Oncolytic vaccinia therapy of squamous cell carcinoma," Mol.Cancer 8:45 (2009).

(56) References Cited

OTHER PUBLICATIONS

Zacal et al., "Enhanced expression from the human cytomegalovirus immediate early promoter in a non-replicating adenovirus encoded reporter gene following cellular exposure to chemical DNA damaging agents," Biochem. Biophys. Res.Commun. 332(2):441-449 (2005).
Zhan et al., "Tumor-specific intravenous gene delivery using oncolytic adenoviruses." Cancer Gene Ther. 12(1):19-25 (2005).
Office Action, issued Oct. 8, 2009, in connection with Japanese Patent Application No. 2003-519509, 27 pages.
Office Action, issued Feb. 4, 2013, in connection with corresponding Chinese Patent Application No. 200810130048.9, 6 pages. [in Chinese with English translation provided].
Genelux Press Release Jun. 14, 2012, "Genelux corporation announces first patient dosed in phase I combination clinical trial of GL-ONC1," [online] Published on Jun. 14, 2012 [online][retrieved on Jan. 28, 2013] Retrieved from:<URL:genelux.com/genelux2012/?page_id=2701 [2 pages].
Genelux Press Release May 31, 2012, "Genelux corporation announces treatment of first patient in phase I/II clinical trial of GL-ONC1 in advanced peritoneal cavity cancers," [online] Published on May 31, 2012 [online][retrieved on Jan. 28, 2013] Retrieved from:<URL:genelux.com/genelux2012/?page_id=2691 [2 pages].
Genelux Press Release May 30, 2012, "Genelux corporation announces phase I data presentation at 2012 Asco Annual Meeting of GL-Onc I , its oncolytic virus lead product candidate," [online] Published on May 30, 2012 [online][retrieved on Jan. 28, 2013] Retrieved from:<URL:genelux.com/genelux2012/?page_id=2686 &preview=true [2 pages].
Genelux Press Release Jun. 6, 2011, "ASCO poster presentation unveils preliminary results of phase I clinical trial involving intraveneous administration of GL-ONC1 to patients with advanced solid tumor cancers," [online] Published on Jun. 6, 2011 [retrieved on Jan. 28, 2013] Retrieved from:<URL: genelux.com/genelux2012/?page_id=1357 [1 page].
Gentschev et al., "Preclinical evaluation of oncolytic vaccinia virus for therapy of canine soft tissue sarcoma," PLoS One 7:(5) 37239, 12 pages, (2012).
Gentschev et al., "Characterization and evaluation of a new oncolytic Vaccinia Virus strain L1VP6.1.1 for canine cancer therapy," Bioengineered 4:2 1-6, (2013).
Gholami et al., "Vaccinia virus GLV-1h153 is effective in treating and preventing metastatic triple-negative breast cancer," Annals of Surgery 256(3), 437-445 (2012).
Haddad et al., "Imaging characteristics, tissue distribution, and spread of a novel oncolytic vaccinia virus carrying the human sodium iodide symporter," PLoS One 7(8):e41647, 9 pages (2012).
Haddad et al., "A vaccinia virus encoding the human sodium iodide symporter facilitates long-term image monitoring of virotherapy and targeted radiotherapy of pancreatic cancer," J. Nucl. Med. 53:1933-1942, (2012).
Macken et al., "General method for production and selection of infectious vaccinia virus recombinants expressing foreign. genes," J. Virol., 49(3): 857-864, (1984).
Patil et al., "Virotherapy of canine tumors with oncolytic vaccinia virus GLV-1h109 expressing an anti-VEGF single-chain antibody," PLoS One 7(10):e47472, 13 pp. (2012).
Reinboth et al., "Correlates between host and viral transcriptional program associated with different oncolytic vaccinia virus isolates," Hum Gene Ther Methods, 23(5):285-296, (2012).
Reinboth et al., "Correlation between human and oncolytic vaccinia virus transcriptional profile," 27th Annual Meeting Final Program, Society for Immunotherapy of Cancer (SITC), Oct. 26-28, 2012, North Bethesda MD. [Poster 82 abstract] 2 pages.
Schaefer et al., "Vaccinia virus-mediated intra-tumoral expression of matrix metalloproteinase 9 enhances oncolysis of Pc-3 xenograft tumors," BMC Cancer 12(1): 366, (2012).
Stritzker et al., "Vaccinia virus-mediated melanin production allows MR and optoacoustic deep tissue imaging and laser-induced thermotherapy of cancer," Proc. Natl. Acad. Sci. Feb. 11, 2013 [Epub ahead of print PMID 23401518], 1-5, (2013).
Wang et al., "Oncolytic vaccinia virus GLV-1h68 strain shows enhanced replication in human breast cancer stem-like cells in comparison to breast cancer cells," J. Transl. Med. 10(1):167, (2012).
Weibel et al., "Imaging of intratumoral inflammation during oncolytic virotherapy of tumors by 19F-Magnetic resonance imaging (MRI)," PLoS One 8(2):e56317, 12 pages, (2013).
Weintraub, A., "Pet dogs help biotech startups find new weapons to fight cancer," Xconomy, Jul. 25, 2012, [online] [retrieved on Jan. 28, 2013] [retrieved from http://www.xconomy.com/san-diego/2012/07/25/pet-dogs-help-biotech-startups-find-new-weapons-to-fight-cancer/?single_page=true].
Yu et al., "Real-time imaging of tumors using replication-competent light emitting microorganisms," Methods Mol. Biol. 872: 159-175, (2012).
Office Action, issued Sep. 25, 2012, in connection with corresponding U.S. Appl. No. 10/866,606, 15 pages.
Response to Office Action issued May 24, 2012, in connection with corresponding Chinese Application No. 200810130048.9, mailed Oct. 8, 2012 [Response in Chinese with instructions to Foreign Associate in English] 17 pages.
Letter/Written Disclosure of the Supplemental Information Disclosure Statement for the above-referenced application, mailed on the same date herewith, 2 pages.
Examination Report, issued May 2, 2013, and received May 30, 2013, in connection with Israeli Patent Application No. 160052 [in Hebrew, provided with English translation], 7 pages.
AACR Press Release Sep. 15, 2011, Virus shows promise for imaging and treating pancreatic cancer, Published on Sep. 15, 2011 [online][retrieved on Jan. 28, 2013] Retrieved from:<URL:aacr.org/home/public—media/aacr-press-releases.aspx?d=2438 [2 pages].
Advani, et al., "Preferential replication of systemically delivered oncolytic vaccinia virus to focally irradiated glioma xenografts," Clin Cancer Res. 18(9):2579-2590, (2012).
Chen et al., "Oncolytic viruses," Advances in Virology, 2, (2012).
Chen et al., "Oncolytic vaccinia virus: a theranostic agent for cancer," Future Virology, 5(6):763-784 (2010).
Chen et al., "Tropism of oncolytic vaccinia virus constructs for human mononuclear cell subsets," 27th Annual Meeting Final Program, Society for Immunotherapy of Cancer (SITC), Oct. 26-28, 2012, North Bethesda MD. [oral presentation abstract] 1 page.
Donat et al., "Preferential colonization of metastases by oncolytic vaccinia virus strain GLV-1h68 in a human PC-3 prostate cancer model in nude mice," PLOS ONE 7(9):e45942, 13 pages (2012).
Genelux Press Release Nov. 1, 2012, "Genelux corporation announces early results of a phase I/II clinical trial of virotherapeutic GL-ONC1 in advanced peritoneal cavity cancers," [online] Published on Nov. 1, 2012 [online][retrieved on Jan. 28, 2013] Retrieved from:<URL:genelux.com/genelux2012/?page_id=4157 [3 pages].
Genelux Press Release Jun. 28, 2012, " Genelux corporation announces ground-breaking clinical study evaluating oncolytic vaccinia virus in canine cancer patients," [online] Published on Jun. 28, 2012 [online][retrieved on Jan. 28, 2013] Retrieved from:<URL:genelux.com/genelux2012/?page_id=3824 [2 pages].

\* cited by examiner

LIGHT EMITTING MICROORGANISMS AND CELLS FOR DIAGNOSIS AND THERAPY OF TUMORS

This application is a continuation of U.S. application Ser. No. 10/866,606, to Aladar Szalay, filed Jun. 10, 2004, entitled "Light emitting microorganisms and cells for diagnosis and therapy of tumors," which is a continuation of U.S. application Ser. No. 10/189,918, to Aladar Szalay, filed Jul. 3, 2002 now abandoned, entitled "Light emitting microorganisms and cells for diagnosis and therapy of tumors," which claims the benefit of priority, under U.S.C. §119 (a)-(d), to European Application No. 01125911.6, to Aladar Szalay, filed Oct. 30, 2001, entitled "Light Emitting Microorganisms and cells for diagnosis and therapy of tumors," and to European Application No. 01 118 417.3, to Aladar Szalay, filed Jul. 31, 2001, entitled "Light Emitting Microorganisms and cells for diagnosis and therapy of tumors." The subject matter of these applications is incorporated herein in its entirety.

The present invention relates to diagnostic and pharmaceutical compositions comprising a microorganism or cell containing a DNA sequence encoding a detectable protein or a protein capable of inducing a detectable signal, e.g. a luminescent or fluorescent protein. The present invention also relates to the use of said microorganism or cell for tumor-targeting or tumor-imaging. For therapeutic uses, said microorganism or cell additionally contain an expressible DNA sequence encoding a protein suitable for tumor therapy, e.g. a cytotoxic or cytostatic protein.

Presence of bacteria in tumors was reported approximately fifty years ago. Several publications substantiated the earlier clinical findings that unexpectedly large numbers of bacteria were discovered in excised tumors from human patients. Investigators argue that chronic infections may predispose cells to malignant growth. Chronic infections of various strains of *Chlamydia* have been associated with lung and cervical cancer as well as malignant lymphoma. Another well described association between the presence of a specific bacterial species and cancer development is *Helicobacter pylori* in patients with gastric ulcers. Elevated levels of *H. pylori*-associated antibodies have been found in patients with duodenal ulcer and gastric adenocarcinoma. These observations demonstrate a concomitant presence of bacteria at tumor sites; however, it was yet not clear whether the microorganisms were the cause of tumor formation or whether the tumorous tissues were more susceptible to bacterial colonization. Intravenously injected strict anaerobic bacteria, *Clostridium pasteurianum*, into mice replicated selectively in the tumor suggesting a hypoxic microenvironment in the necrotic center. Intravenous injection of attenuated *Salmonella typhimurium* mutants resulted in elevated bacterial titers in the tumor tissues in comparison to the other organs of mice upon histologic and bacteriologic analyses.

Similarly, the presence of virus particles was reported in excised human breast tumors as early as 1965. More recently, based on polymerase chain reaction (PCR) data, the human papillomavirus has been claimed to be associated with anogenital tumors and esophageal cancers, breast cancers, and most commonly, cervical cancers. In addition, the presence of hepatitis C virus in human hepatocellular carcinoma, Epstein-Barr virus in squamous cell carcinoma in Kirnura's disease, mouse mammary tumor virus-like particles (MMTV) in human breast cancer, SV40 virus in macaque astrocytoma, and herpesvirus in turtle fibropapilloma has also been reported. Surprisingly, the concentration of virus particles in the tumors shows variations among patients. The presence of human papillomavirus in squamous cell carcinomas of the esophagus ranges from 0 to 72% (10-15). In contrast to tumor tissues, no virus particles have been found in tumor-free areas of the esophageal epithelium of the same patient suggesting that the virus particles are located only in the tumor tissues.

However, so far it could not undoubtedly been shown whether the above discussed microorganisms are responsible for the development of disorders like tumors (except for papillomaviruses) or whether, e.g., tumors can attract and/or protect viruses or bacteria. Accordingly, there was no basis for the use of such microorganisms for the diagnosis or therapy of tumors. Conventional tumor diagnostic methods, such as MRI (Magnetic Resonance Imaging) and therapeutic methods, e.g. surgery, are invasive and not very sensitive.

Therefore, it is the object of the present invention to provide a means for the efficient and reliable diagnosis as well as the therapy of tumors which overcomes the disadvantages of the diagnostic and therapeutic approaches presently used.

According to the present invention this is achieved by the subject matters defined in the claims. When Vaccinia virus (LIVP strain) carrying the light emitting fusion gene construct rVV-ruc-gfp was injected intravenously into nude mice, the virus particles were found to be cleared from all internal organs within 4 days, as determined by extinction of light emission. In contrast, when the fate of the injected Vaccinia virus was similarly followed in nude mice bearing tumors grown from subcutaneously implanted C6 rat glioma cells, virus particles were found to be retained over time in the tumor tissues, resulting in lasting light emission. The presence and amplification of the virus-encoded fusion proteins in the same tumor were monitored in live animals by observing GFP fluorescence under a stereomicroscope and by collecting luciferase-catalyzed light emission under a low-light video-imaging camera. Tumor-specific light emission was detected 4 days after viral injection in nude mice carrying subcutaneous C6 glioma implants ranging in size from 25 to 2500 mm$^3$. The signal became more intense after the 4th postinjection day and lasted for 30 to 45 days, indicating continued viral replication. Tumor accumulation of rVV-ruc-gfp virus particles was also seen in nude mice carrying subcutaneous tumors developed from implanted PC-3 human prostate cells, and in mice with orthotopically implanted MCF-7 human breast tumors. Further, intracranial C6 rat glioma cell implants in immunocompetent rats and MB-49 human bladder tumor cell implants in C57 mice were also targeted by the Vaccinia virus. Cross sections of a C6 glioma revealed that light emission was clustered in "patches" at the periphery of the tumor where the fast-dividing cells reside. In contrast, cross sections of breast tumors revealed that fluorescent "islands" were distributed throughout the tumors. In addition to primary breast tumors, small metastatic tumors were also detected externally in the contralateral breast region, as well as in nodules on the exposed lung surface, suggesting metastasis to the contralateral breast and lung. In summary, light-emitting cells or microorganisms, e.g. Vaccinia virus can be used to detect and treat primary and metastatic tumors.

Similar results were obtained with light-emitting bacteria (Salmonella, *Vibrio, Listeria, E. coli*) which were injected intravenously into mice and which could be visualized in whole animals under a low light imager immediately. No light emission was detected twenty-four hours after bacterial injection in both athymic (nu/nu) mice and immunocompetent C57 mice as a result of clearing by the immune system. In the cutaneous wound of an intravenously injected animal, the bacterial light emission increases and remains detectable up to six days post-injection. In nude mice bearing tumors developed from implanted C6 glioma cells, light emission was abolished from the animal entirely twenty-four hours after delivery of bacteria, similar to mice without tumors. However, forty-eight hours post-injection, unexpectedly, a strong, rapidly increasing light emission originated only from the tumor regions was observed. This observation indicates a continuous bacterial replication in the tumor tissue. The extent of light emission is dependent on the bacterial strain used. The homing-in process together with the sustained light emission was also demonstrated in nude mice carrying prostate, bladder, and breast tumors. In addition to primary tumors, metastatic tumors could also be visualized as exemplified in the breast tumor model. Tumor-specific light emission was also observed in immunocompetent C57 mice with bladder tumors as well as in Lewis rats with brain glioma implants. Once in the tumor, the light-emitting bacteria were not observed to be released into the circulation and to recolonize subsequently implanted tumors in the same animal. Further, mammalian cells expressing the Ruc-GFP fusion protein, upon injection into the bloodstream, were also found to home into and propagate in glioma tumors.

These findings open the way for (a) designing multifunctional viral vectors useful for the detection of tumors based on signals like light emission and/or for suppression of tumor development and/or angiogenesis signaled by, e.g., light extinction and (b) the development of bacterium- and mammalian cell-based tumor targeting systems in combination with therapeutic gene constructs for the treatment of cancer. These systems have the following advantages: (a) They target the tumor specifically without affecting normal tissue; (b) the expression and secretion of the therapeutic gene constructs are, preferably, under the control of an inducible promoter, enabling secretion to be switched on or off; and (c) the location of the delivery system inside the tumor can be verified by direct visualization before activating gene expression and protein delivery.

Accordingly, the present invention relates to a diagnostic or pharmaceutical composition comprising a microorganism or cell containing a DNA sequence encoding a detectable protein or a protein capable of inducing a detectable signal.

Any microorganism or cell is useful for the diagnostic method of the present invention, provided that they replicate in the organism, are not pathogenic for the organism e.g. attenuated and, are recognized by the immune system of the organism, etc.

In a preferred embodiment, the diagnostic or pharmaceutical composition comprises a microorganism or cell containing a DNA sequence encoding a luminescent and/or fluorescent protein.

As used herein, the term "DNA sequence encoding a luminescent and/or fluorescent protein" also comprises a DNA sequence encoding a luminescent and fluorescent protein as fusion protein.

In an alternative preferred embodiment, the diagnostic or pharmaceutical composition of the present invention comprises a microorganism or cell containing a DNA sequence encoding a protein capable of inducing a signal detectable by magnetic resonance imaging (MRI), e.g. metal binding proteins. Furthermore, the protein can bind contrast agents, chromophores, ligands or compounds required for visualization of tissues.

Preferably, for transfecting the cells the DNA sequences encoding a luminescent and/or fluorescent protein are present in a vector or an expression vector. A person skilled in the art is familiar with examples thereof. The DNA sequences can also be contained in a recombinant virus containing appropriate expression cassettes. Suitable viruses that may be used in the diagnostic or pharmaceutical composition of the present invention include baculovirus, vaccinia, sindbis virus, Sendai virus, adenovirus, an AAV virus or a parvovirus, such as MVM or H-1. The vector may also be a retrovirus, such as MoMULV, MoMuLV, HaMuSV, MuMTV, RSV or GaLV. For expression in mammals, a suitable promoter is e.g. human cytomegalovirus "immediate early promoter" (pCMV). Furthermore, tissue and/or organ specific promoters are useful. Preferably, the DNA sequences encoding a luminescent and/or fluorescent protein are operatively linked with a promoter allowing high expression. Such promoters, e.g. inducible promoters are well-known to the person skilled in the art.

For generating the above described DNA sequences and for constructing expression vectors or viruses which contain said DNA sequences, it is possible to use general methods known in the art. These methods include e.g. in vitro recombination techniques, synthetic methods and in vivo recombination methods as described in Sambrook et al., Molecular Cloning, A Laboratory Manual, $2^{nd}$ edition (1989) Cold Spring Harbor Laboratory Press, Cold Spring Harbor, N.Y., for example. Methods of transfecting cells, of phenotypically selecting transfectants and of expressing the DNA sequences by using the above described vectors are known in the art.

The person skilled in the art knows DNA sequences encoding luminescent or fluorescent proteins that can be used in the diagnostic or pharmaceutical of the present invention. During the past decade, the identification and isolation of structural genes encoding light-emitting proteins from bacterial luciferase from *Vibrio harveyi* (Belas et al., Science 218 (1982), 791-793) and from *Vibrio fischerii* (Foran and Brown, Nucleic acids Res. 16 (1988), 177), firefly luciferase (de Wet et al., Mol. Cell. Biol. 7 (1987), 725-737), aequorin from *Aequorea Victoria* (Prasher et al., Biochem. 26 (1987), 1326-1332), *Renilla* luciferase from *Renilla reniformis* (Lorenz et al., PNAS USA 88 (1991), 4438-4442) and green fluorescent protein from *Aequorea victoria* (Prasher et al., Gene 111 (1987), 229-233) have been described that allow the tracing of bacteria or viruses based on light emission. Transformation and expression of these genes in bacteria allows detection of bacterial colonies with the aid of the low light imaging camera or individual bacteria under the fluorescent microscope (Engebrecht et al., Science 227 (1985), 1345-1347; Legocki et al., PNAS 83 (1986), 9080-9084; Chalfie et al., Science 263 (1994), 802-805).

Luciferase genes have been expressed in a variety of organisms. Promoter activation based on light emission, using lux AB fused to the nitrogenase promoter, was demonstrated in *Rhizobia* residing within the cytoplasm of cells of infected root nodules by low light imaging (Legocki et al., PNAS 83 (1986), 9080-9084; O'Kane et al., J. Plant Mol. Biol. 10 (1988), 387-399). Fusion of the lux A and lux B genes resulted in a fully functional luciferase protein (Escher et al., PNAS 86 (1989), 6528-6532). This fusion gene (Fab2) was introduced into *Bacillus subtilis* and *Bacillus megatherium* under the xylose promoter and then fed into insect larvae and was injected into the hemolymph of worms. Imaging of light emission was conducted using a low light video camera. The movement and localization of pathogenic bacteria in transgenic *arabidopsis* plants, which carry the pathogen-activated PAL promoter-bacterial luciferase fusion gene construct, was demonstrated by localizing *Pseudomonas* or *Erwinia* spp. infection under the low light imager as well as in tomato plant and stacks of potatoes (Giacomin and Szalay, Plant Sci. 116 (1996), 59-72).

All of the luciferases expressed in bacteria require exogenously added substrates such as decanal or coelenterazine for light emission. In contrast, while visualization of GFP fluorescence does not require a substrate, an excitation light source is needed. More recently, the gene cluster encoding the bacterial luciferase and the proteins for providing decanal within the cell, which includes luxCDABE was isolated from *Xenorhabdus luminescens* (Meighen and Szittner, J. Bacteriol. 174 (1992), 5371-5381) and *Photobacterium leiognathi* (Lee et al., Eur. J. Biochem. 201 (1991), 161-167) and transferred into bacteria resulting in continuous light emission independent of exogenously added substrate (Fernandez-Pinas and Wolk, Gene 150 (1994), 169-174). Bacteria containing the complete lux operon sequence, when injected intraperitoneally, intramuscularly, or intravenously, allowed the visualization and localization of bacteria in live mice indicating that the luciferase light emission can penetrate the tissues and can be detected externally (Contag et al., Mol. Microbiol. 18 (1995), 593-603).

Preferably, the microorganism is a bacterium, e.g. attenuated. Particularly preferred is attenuated *Salmonella thyphimurium*, attenuated *Vibrio cholerae* or attenuated *Listeria monocytogenes* or *E. coli*. Alternatively, viruses such as Vaccinia virus, AAV, a retrovirus etc. are also useful for the diagnostic and therapeutic compositions of the present invention. Preferably, the virus is Vaccinia virus.

Preferably, the cell of the diagnostic or therapeutic composition of the present invention is a mammalian cell such as stem cells which can be autologous or heterologous concerning the organism.

In a further preferred embodiment of the diagnostic or therapeutic composition of the present invention the luminescent or fluorescent protein is a luciferase, green fluorescent protein (GFP) or red fluorescent protein (RFP).

In a particularly preferred embodiment, the microorganism or cell of the diagnostic or pharmaceutical composition of the present invention additionally contains a gene encoding a substrate for the luciferase. In an even more preferred embodiment, the microorganism or cell of the diagnostic or pharmaceutical composition of the present invention contains a ruc-gfp expression cassette which contains the *Renilla* luciferase (ruc) and *Aequorea* gfp cDNA sequences under the control of a strong synthetic early/late (PE/L) promoter of Vaccinia or the luxCDABE cassette.

A preferred use of the microorganisms and cells described above is the preparation of a diagnostic composition for tumor-imaging. The diagnostic composition of the present invention can be used e.g. during surgery, to identify tumors and metastasis. Furthermore, the diagnostic composition of the present invention is useful for monitoring a therapeutic tumor treatment. Suitable devices for analyzing the localization or distribution of luminescent and/or fluorescent proteins in an organism, organ or tissue are well known to the person skilled in the art and, furthermore described in the literature cited above as well as the Examples, below. Additionally, the microorganisms and cells can be modified in such a way that they bind metals and consequently are useful in MRI technology to make this more specific.

The present invention also relates to a pharmaceutical composition containing a microorganism or cell as described above, wherein said microorganism or cell furthermore contains one or more expressible DNA sequence(s) encoding (a) protein(s) suitable for tumor therapy and/or elimination of metastatic tumors, such as a cytotoxic protein, a cytostatic protein, a protein inhibiting angiogenesis, or a protein stimulating apoptosis. Such proteins are well-known to the person skilled in the art. Furthermore, the protein can be an enzyme converting an inactive substance (pro-drug) administered to the organism into an active substance, i.e. toxin, which is killing the tumor or metastasis. For example, the enzyme can be glucuronidase converting the less toxic form of the chemotherapeutic agent glucuronyldoxorubicin into a more toxic form. Preferably, the gene encoding such an enzyme is directed by a promoter which is inducible additionally ensuring that the conversion of the pro-drug into the toxin only occurs in the target tissue, i.e. tumor. Such promoters are e.g. IPTG-, antibiotic-, heat-, pH-, light-, metall-, aerobic-, host cell-, drug-, cell cycle- or tissue specific-inducible promoters. Additional examples of suitable proteins are human endostatin and the chimeric PE37/TGF-alpha fusion protein. Endostatin is a carboxyterminal peptide of collagen XVIII which has been characterized (Ding et al., PNAS USA 95 (1998), 10443). It has been shown that endostatin inhibits endothelial cell proliferation and migration, induces G1 arrest and apoptosis of endothelial cells in vitro, and has antitumor effect in a variety of tumor models. Intravenous or intramuscular injection of viral DNA and cationic liposome-complexed plasmid DNA encoding endostatin result in limited expression levels of endostatin in tumors. However intratumoral injection of purified endostatin shows remarkable inhibition of tumor growth. *Pseudomonas* exotoxin is a bacterial toxin secreted by *Pseudomonas aeruginosa*. PE elicits its cytotoxic effect by inactivating elongation factor 2 (EF-2), which results in blocking of protein synthesis in mammalian cells. Single chain PE is functionally divided into three domains: domain Ia is required for binding to cell surface receptor, domain II is required for translocating the toxin into the target cell cytosol, and domain III is responsible for cytotoxicity by inactivating EF-2. PE40 is derived from wild type *Pseudomonas* exotoxin that lacks the binding domain Ia. Other proteins such as antibody fragments or protein ligands can be inserted in place of the binding domain. This will render the PE40-ligand fusion protein specific to its receptor. One of the highly specific engineered chimeric toxins is the TGF alpha/PE40 fusion protein, where the C-terminus of TGF alpha polypeptide has been fused in frame with the N-terminus of the PE40 protein. TGF alpha is one of the ligands of epidermal growth factor receptor (EGFR), which has been shown to be preferentially expressed on the surface of a variety of tumor cells. TGF alpha-PE40 fusion protein has been shown to be highly toxic to tumor cells with elevated EGFRs on the cell surface and while it is less toxic to nearby cells displaying fewer numbers of surface EGFR. The toxicity of TGF alpha-PE40 chimeric protein is dependent on a proteolytic processing step to convert the chimeric protein into its active form, which is carried out by the target. To overcome the requirement for proteolysis, a new chimeric toxin protein that does not require processing has been constructed by Theuer and coworkers (J. Biol. Chem. 267 (1992), 16872). The novel fusion protein is termed PE37/TGF alpha, which exhibited higher toxicity to tumor cells than the TGF alpha-PE40 fusion protein.

Thus, in a preferred embodiment of the pharmaceutical composition, the protein suitable for tumor therapy is endostatin (for inhibition of tumor growth) or recombinant chimeric toxin PE37/transforming growth factor alpha (TGF-alpha) (for cytotoxicity to tumor cells).

Moreover, the delivery system of the present application even allows the application of compounds which could so far not be used for tumor therapy due to their high toxicity when systemically applied. Such compounds include proteins inhibiting elongation factors, proteins binding to ribosomal subunits, proteins modifying nucleotides, nucleases, proteases or cytokines (e.g. IL-2, IL-12 etc.), since experimental data suggest that the local release of cytokines might have a positive effect on the immunosuppressive status of the tumor.

Furthermore, the microorganism or cell can contain a BAC (Bacterial Artificial Chromosome) or MAC (Mammalian Artificial Chromosome) encoding several or all proteins of a specific pathway, e.g. anti-angionesis, apoptosis, woundhealing-pathway or anti-tumor growth. Additionally the cell can be cyber cell or cyber virus endocing these proteins.

For administration, the microorganisms or cells of the present invention are preferably combined with suitable pharmaceutical carriers. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the microorganisms or cells may be effected by different ways, e.g. by intravenous, intrapereotoneal, subcutaneous, intramuscular, topical or intradermal administration. The preferred route of administration is intravenous injection. The route of administration, of course, depends on the nature of the tumor and the kind of microorganisms or cells contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind, size and localization of the tumor, general health and other drugs being administered concurrently.

Preferred tumors that can be treated with the microorganisms or cells of the present invention are bladder tumors, breast tumors, prostate tumors, glioma tumors, adenocarcinomas, ovarial carcinomas, and pancreatic carcinomas; liver tumors, skin tumors.

C6 glioma cells ($5\times10^5$) were implanted subcutaneously into the right lateral thigh of nude mice. Ten days after tumor cell implantation, the animals were infected intravenously with $1\times10^8$ pfu of rVV-ruc-gfp. GFP expression was monitored 7 days post-viral injection. Vascularization at the surface of the subcutaneous C6 glioma tumor is shown against the bright green fluorescent background in the tumor following Vaccinia-mediated gene expressions. Bright field (A), fluorescence (B), and bright field, fluorescence overlay (C) images of subcutaneous glioma tumor are illustrated. (Bars=5 mm.)

Figure 3:
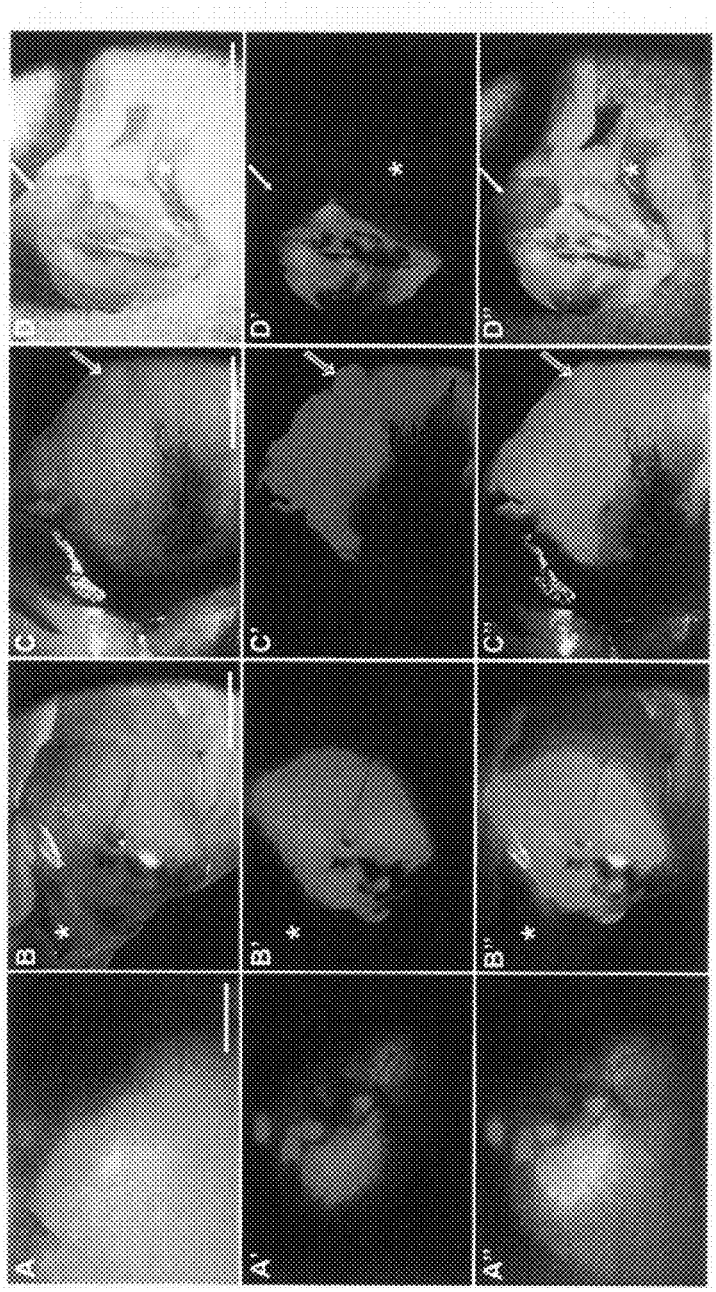

FIG. 3: Expression of GFP in Subcutaneous Glioma Tumor of the Same Animal

Five days after the subcutaneous implantation of $5\times10^5$ C6 glioma cells into the right lateral thigh, $10^8$ of rVV-ruc-gfp virus particles were injected intravenously. Five days after viral injection, the animal was anesthetized and sacrificed for analysis of GFP expression under fluorescence microscope. The tumor was visualized externally (A-A"), with the overlying skin reflected (B-B"), in cross section (C-C"), and in the amputated leg (D-D"). Bright field (A), fluorescence (B), and bright field, fluorescence overlay (C) images of subcutaneous glioma tumor are illustrated. The strongest GFP expressions are seen as patches located along the outer surface of the tumor on the right (double arrows in C-C"). Sharp difference of GFP expression in tumor tissue and in the normal muscle tissue (arrows in D-D") is clearly visible. Asterisks mark the reflected skin (B-B" and D-D"). (Bars=5 mm.)

Figures 4, 5:
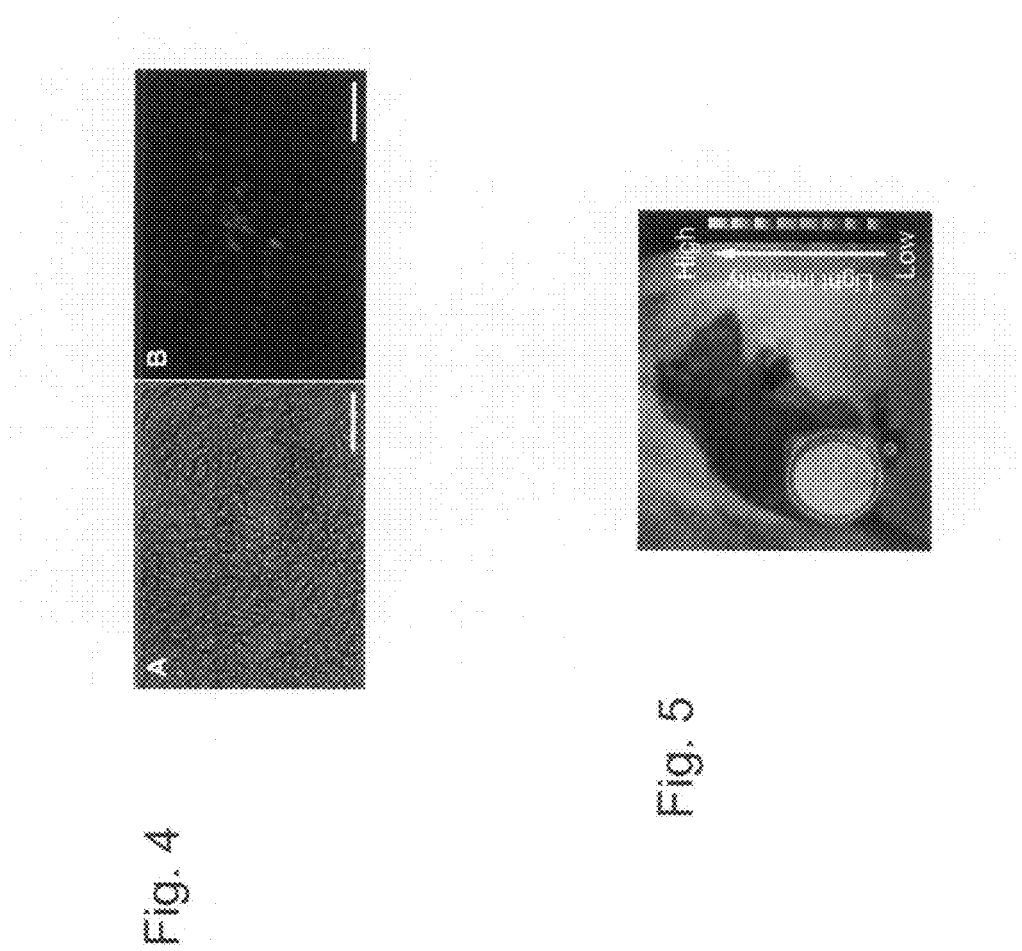

FIG. 4: Bright Field (A) and Fluorescence (B) Images of Tumor Cells Expressing GFP Frozen sections (30 μm thick) of the glioma tumor tissues were prepared from a nude mouse that has been intravenously injected with $1\times10^8$ of rVV-rucgfp virus particles. (Bars=50 μm.)

FIG. 5: Low Light Image of the Anesthetized Nude Mouse to Indicate the Location of *Renilla* luciferase-Triggered Light Emission in the Presence of Intravenously Injected Substrate Coelenterazine (5 μg Ethanol Solution)

Figure 6:
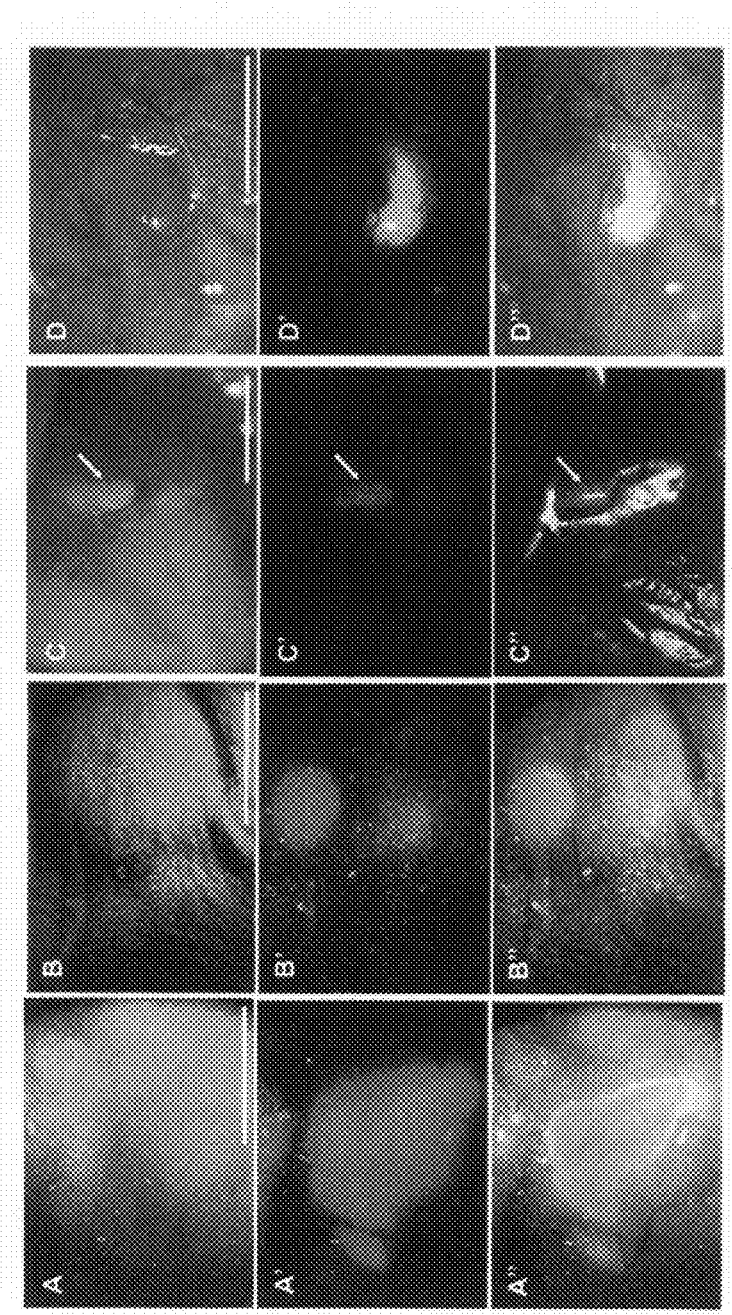

FIG. 6: Monitoring Tumor-Specific Viral Infection Based on GFP Gene Expression in a Variety of Tumor Models GFP gene expression was monitored in a variety of tumor models including subcutaneous PC-3 human prostate tumor (A-A") and MCF-7 human breast tumor (B-B") in nude mice, intracranial C6 rat glioma tumor (C-C", arrows indicate the location of the tumor) in Lewis rats, and MB-49 human bladder tumor (D-D") in C57 mice. Animals were monitored 7 days after intravenous injections of $1\times10^8$ of rVV-ruc-gfp virus particles. Bright field (top), fluorescence (middle), and bright field, fluorescence overlay (bottom) images of the tumor are illustrated. (Bars=5 mm.)

Figure 7:
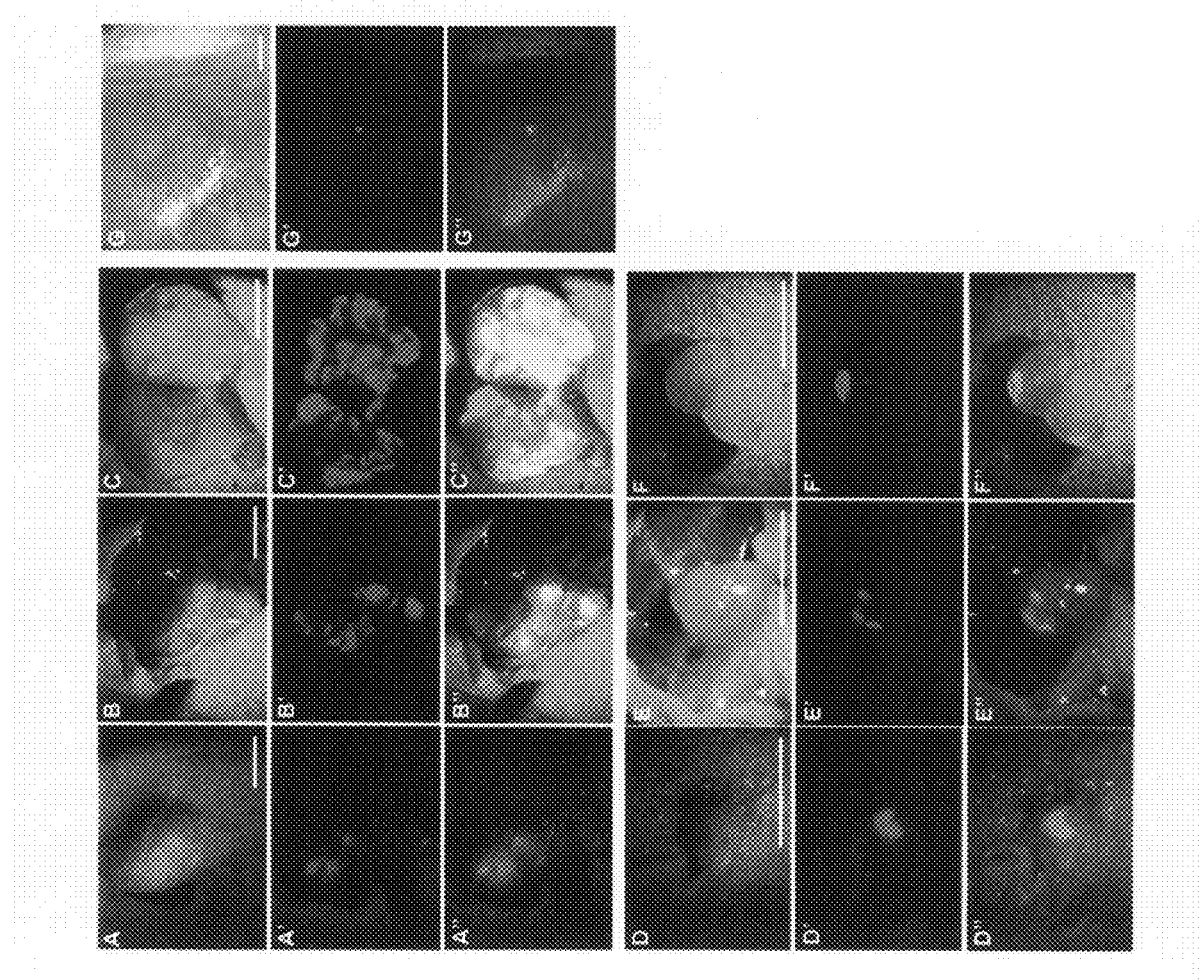

FIG. 7: Monitoring Vaccinia-Mediated GFP Expression in a Breast Tumor Model

Nude mouse carrying breast tumor was injected intravenously with $1\times10^8$ of rVV-ruc-gfp virus particles. Both the primary tumor (A-A", B-B", and C-C") and the metastasized tumor (D-D", E-E", and F-F") were visualized externally (A-A" and D-D"), with overlying skin removed (B-B" and E-E"), and when they were split open (C-C" and F-F") in a set of bright field, fluorescence (') and bright field, fluorescence overlay (") images. GFP expression in lung metastases in the same animal was also visualized (G-G"). (Bars=5 mm (A-A" to F-F"), and Bars=1 mm (G-G").

Figure 8:
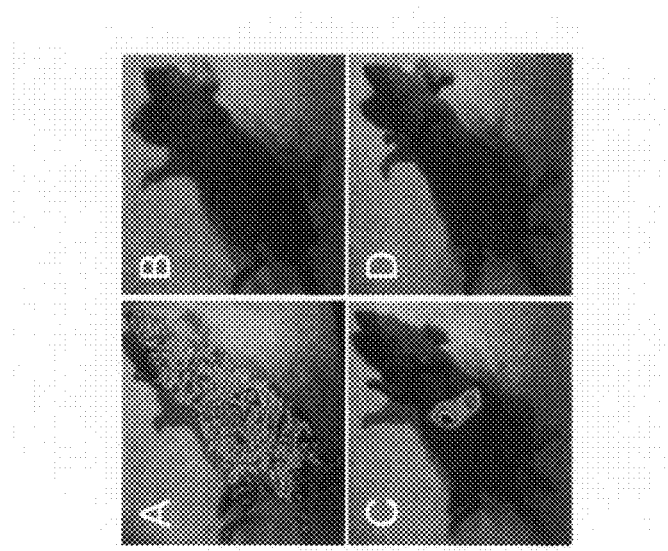

FIG. 8: Visualization of the Clearance of Light Emitting Bacteria From Nude Mice Based on the Detection of Light Emission Under the Low Light Imager Nude mice were intravenously injected with $10^7$ cells of attenuated *S. typhimurium* (A, B) and *V. cholera* (C, D). Both strains were transformed with pLITE201 carrying the lux operon. Photon collection was done 20 min (A, C) and 2 days (B, D) after bacterial injections.

Figure 9:
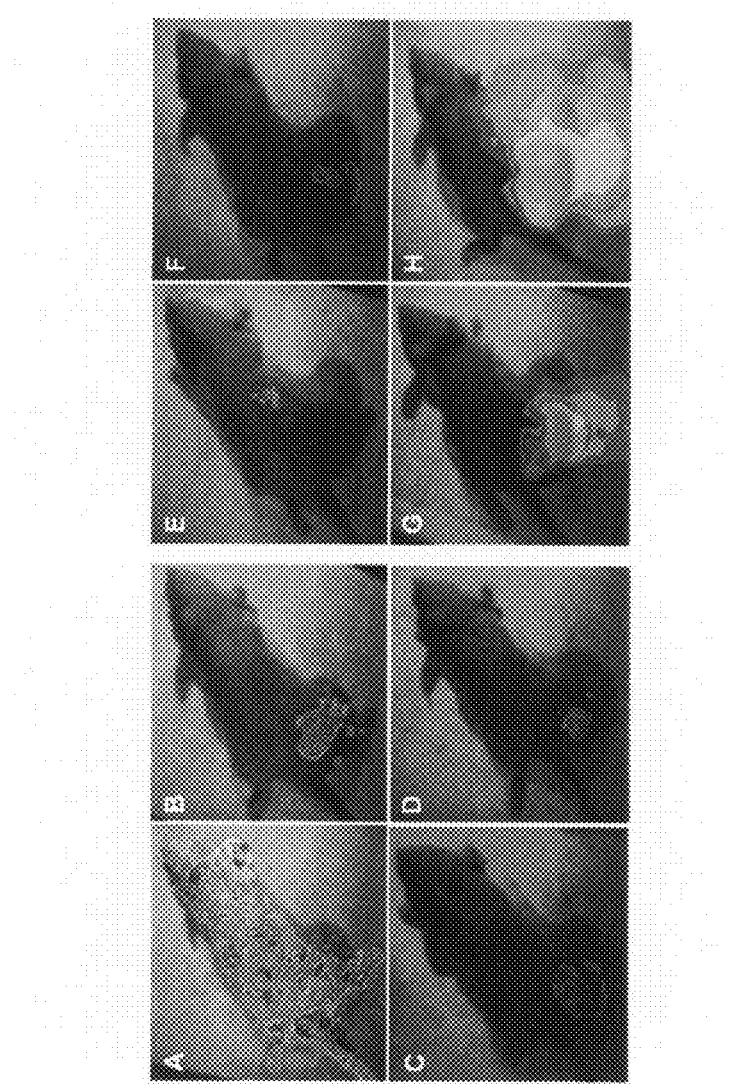

FIG. 9: Homing of Glioma Tumors by Attenuated Bacteria

Nude mice with a C6 glioma tumor in the right hind leg were intravenously injected with $10^7$ attenuated *S. typhimurium* (A-D) and with *V. cholera* (E-H) both transformed with pLITE201 plasmid DNA encoding the lux operon. Photon collection was carried out for one minute under the low light imager. Mice injected with *S. typhimurium* exhibited luminescence immediately through the whole animal (A). In contrast, luminescence in the mice injected with *V. cholera* was visible in the liver area (E). Two days after bacterial injection, both groups of mice demonstrated luminescence only in the tumor region (B, F). The light emission in the tumors infected with *S. typhimurium* slowly diminished four (C) and six (D) days after bacterial injection. Tumors infected with *V. cholera* showed enormously increased light emission four (G) and six (H) days after injection suggesting continued replication of the bacteria in the tumor tissues.

Figure 10:
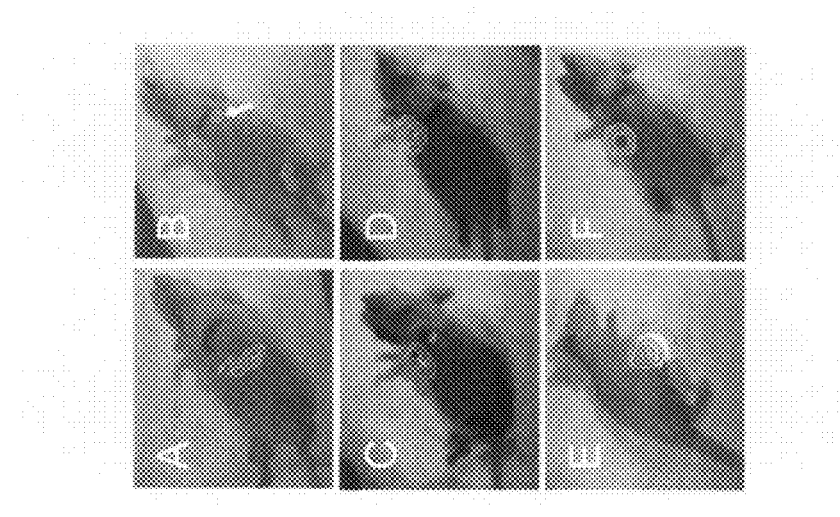

FIG. 10: Homing in of Bacteria onto Breast Tumors

Nude mice with breast tumors in the right breast pad were intravenously injected with $10^7$ attenuated *V. cholera* (A-D) and with $10^7$ *E. coli* (E-F) transformed with pLITE201 plasmid DNA encoding the lux operon. Photon collection was carried out for one minute under the low light imager. Twenty minutes after bacterial delivery, luminescent *V. cholera* were observed in the liver (A). Forty-eight hours after injection, light emission was noted in the primary breast tumor in the right breast area and a metastatic tumor (arrow) in the left breast area, and in the incision wound (B). At five days, the light emission was visible only in the tumor regions, and non at the wound (C). Eight days after bacterial injection, the luminescent activity was abolished from the smaller tumor region but remained strong in the primary breast tumor (D). Homing in of *E. coli* onto breast tumors in nude mice was also observed two days after intravenous bacterial injection (E: side view, F: ventral view).

Figure 11:
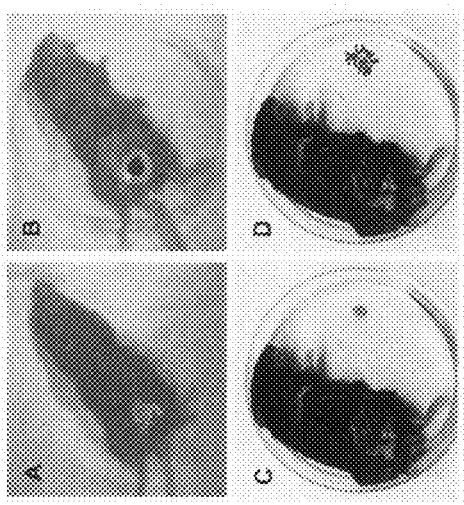

FIG. 11: Homing in of Bacteria Onto Bladder Tumors in C57 Mice

C57 mice were intravenously injected with $10^7$ attenuated *V. cholera* transformed with pLITE201 encoding the lux operon. Nine days after bacterial delivery, luminescence was noted in the bladder region of the whole animal (A). The animal was sacrificed and an abdominal incision was made to expose the bladder. The light emission was limited to the bladder region (B). With the removal of the bladder (C) from the mouse, the entire source of light emission was removed (D) as demonstrated by the overlay of the low light photon emission image over the photographic image of the excised bladder.

Figure 12:
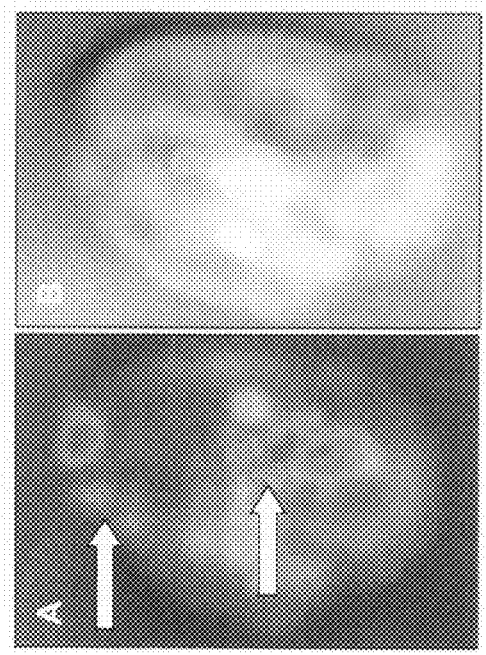

FIG. 12: Homing in of Bacteria onto Brain Glioma Tumors in Lewis Rats

Lewis rats were intravenously injected with $10^8$ cells of attenuated *V. cholera* transformed with pLITE201 encoding the lux operon. Twenty-four hours after bacterial injection, faint luminescence was noted in the head region of the whole animal during visualization under the low light imager. The animals were sacrificed and their brain removed. Photon collection was carried out for one minute from rats with (A) and without (B) brain tumors. Strong luminescence was confirmed in regions of the brain of the rats with the brain tumor (marked with arrows in A). Luminescence was completely absent in the control brain tissues (B).

Figure 13:
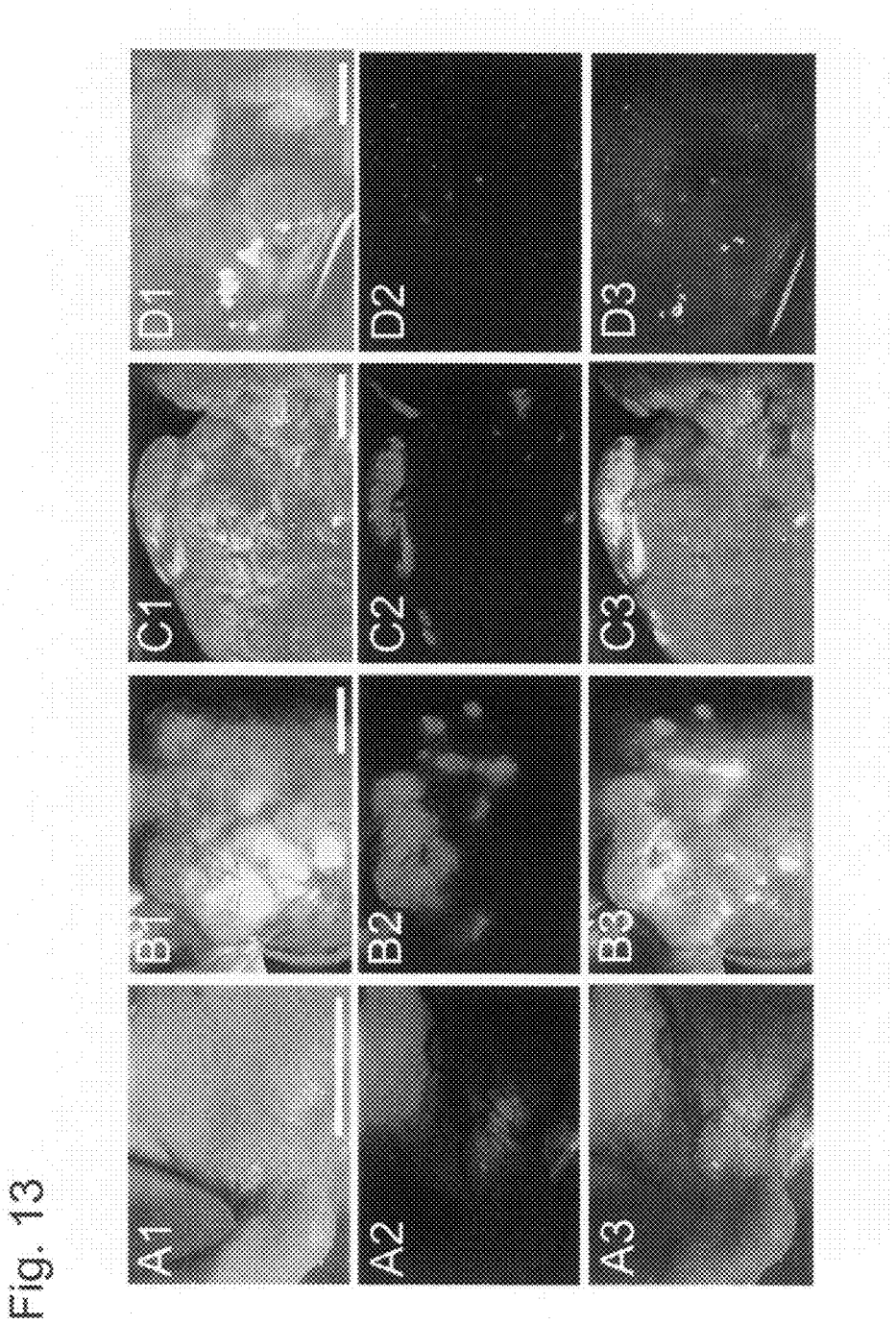

FIG. 13: Transformed Human Fibrosarcoma Cells Home in on Subcutaneous Glioma Tumors in Nude Mice Nude mice with human breast tumors were injected intravenously with $5 \times 10^5$ human fibrosarcoma cells, which were permanently transformed with retrovirus derived from pLEIN. Seven days post-injection, the animals were anesthetized and monitored under a fluorescent stereomicroscope. Fluorescent cells were noted only in the tumor region of the whole mice through the skin (A1-3). Upon exposure of the tumor tissues by reflection of the overlying skin (B1-3), and in cross sections of the tumors (C1-3), fluorescent patches were visible in distinct regions. Close examination of the organs of the mice showed the presence of small clusters of fluorescent cells in the lungs of the animals, demonstrating the affinity of the fibrosarcoma cells for the lungs in addition to the tumorous tissues (D1-3). (Bars=5 mm (A1-C3), =1 mm (D1-D3)).

Figure 14:
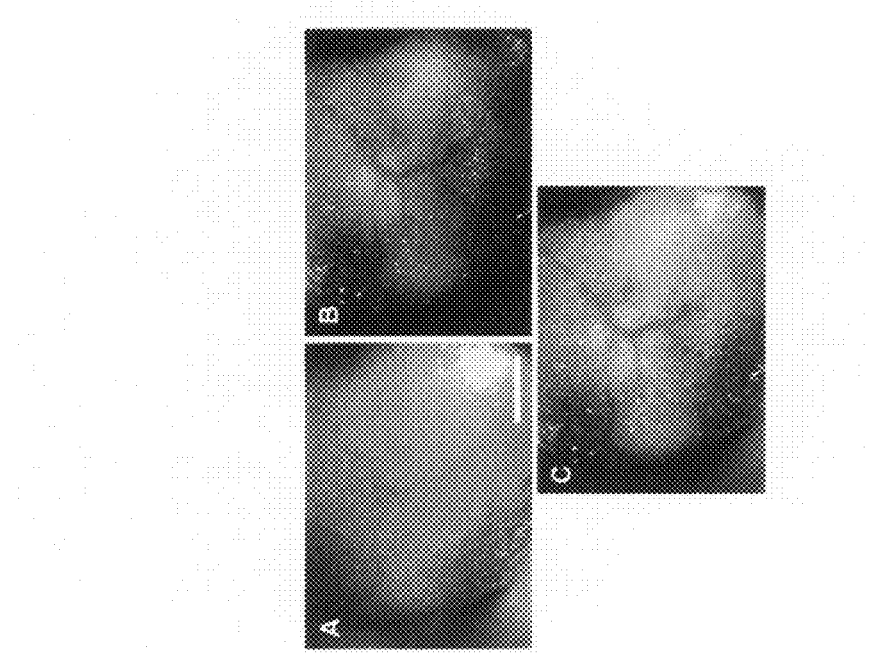

FIG. 14: Homing of Attenuated *Listeria monocytogenes* into Subcutaneous Prostate Tumors Nude mice with subcutaneous human PC3 prostate tumor in the right hind leg were intravenously injected with $10^7$ attenuated *L. monocytogenes* transformed with pSOD-gfp plasmid DNA carrying the gfp cDNA. GFP fluorescence was observed under a fluorescence stereo microscope. Twenty-seven hours after bacterial injection, GFP signal was detected only in the tumor region. The tumor is shown in a set of visible light (a), fluorescent (b), and visible and fluorescent light overlay (C) images. (Bars=5 mm.)

The present invention is explained by the examples.

EXAMPLE 1

Materials and Methods (A) Bacterium strains. The bacterial strains used were attenuated *Salmonella typhimurium* (SL7207 hisG46, DEL407[aroA544::Tn10]), attenuated *Vibrio cholerae* (Bengal 2 Serotyp 0139, M010 DattRS1), and attenuated *Listeria monocytogenes* (D2 mpl, actA, plcB). The bacterial strains were kindly provided by Prof. W. Gobel (University of Wurzburg, Germany).

(B) Plasmid constructs. The plasmid pLITE201 containing the luxCDABE cassette was obtained from (Voisey and Marincs, Biotech 24, 1998, 56-58). The plasmid pXylA-dual with the operon sequence of gfp-cDNA, lux AB, lux CD, and lux E under the control of the Xylose promoter was kindly provided by Dr. Phil Hill (University of Nottingham, UK).

(C) Transformation of Bacteria

The bacteria were transformed by electroporation.

(D) Tumor Cell lines. The rat C6 nitrosourea-induced glioma cell line (ATCC, Rockville, Md.) was cultured in RPMI-1640 medium (Cellgro®, Mediatech, Inc., Herndon, Va.) supplemented with 10% (v/v) FBS and 1× penicillin/streptomycin. The human PC3 prostate carcinoma cell line (ATCC, Rockville, Md.) and the Human MB-49 bladder tumor cells and rat 9L glioma cells were maintained in DMEM medium (Cellgro®, Mediatech, Inc., Herndon, Va.) supplemented with L-glutamine and 10% (v/v) FBS. HT1080 fibrosarcoma cells (ATCC, Manassas, Va.) were cultured in F12 minimal essential media (Cellgro®, Mediatech, Inc., Herndon, Va.) supplemented with 10% FBS and 1× penicillin/streptomycin. The MCF-7 human mammary carcinoma cell line (ATCC, Rockville, Md.), permanently transformed with a plasmid carrying pro-IGF-II cDNA (obtained from Dr. Daisy De Leon, Loma Linda University, Loma Linda, Calif.) was cultured in DMEM/F12 medium supplemented with 5% FBS and 560 µg/ml of G418 (Life Technologies, Grand Island, N.Y.).

(E) Production and propagation of retrovirus to generate a light-emitting stably transformed cell line. PT67 packing cells (Clontech, Palo Alto, Calif.) were cultured in DMEM medium supplemented with 10% (v/v) FBS. At 70% confluence, PT67 cells were transformed with pLEIN (Clontech, Palo Alto, Calif.) using calcium phosphate precipitation method (Profection Mammalian Transfection Systems, Promega, Madison, Wis.) for 12 hours. Fresh medium was replenished at this time. Retroviral supernatant collected from PT67 cells 48 hours post transformation were filtered through a 0.45 µm filter and was added to target HT1080 cells along with polybrene to a final concentration of 4 µg/ml. The medium was replaced after 24 hours and the cells were treated with G418 selection at 400 µg/ml and stepwise increased to 1200 µg/ml.

(F) Recipient animals and tumor models. Five- to six-week-old male BALB/c athymic nu/nu mice (25-30 g in body weight) and Lewis rats (250-300 g in body weight) were purchased from Harlan (Frederick, Md.). C57BL/6J Min/+ mice were obtained from Jackson Laboratories (Bar Harbor, Me.), Min (multiple intestinal neoplasia) is an autosomal dominant trait involving a nonsense mutation in codon 850 of the murine Apc gene, which renders these animals susceptible to spontaneous intestinal adenoma formation. Female BALB/c athymic nu/nu mice bearing MCF-7 human breast tumor implants were generated and kindly provided by Dr. Daisy DeLeon and Dr. Tian (Loma Linda University, Loma Linda, Calif.). C57 mice with orthotopically implanted human MB-49 tumor cells in the bladder were generated and kindly provided by Dr. Istvan Fodor (Loma Linda University, Loma Linda, Calif.). All animal experiments were carried out in accordance with protocol approved by the Loma Linda University animal research committee. The animals containing recombinant DNA materials and attenuated pathogens were kept in Loma Linda University animal care facility under biosafety level two.

(G) Propagation of recombinant vaccinia Virus. Vaccinia virus Lister strain (LIVP) was used as a wild type virus. Recombinant Vaccinia virus rVV-ruc-gfp was constructed by inserting, via homologous recombination, the ruc-gfp-cassette into the Vaccinia virus genome (Wang et al., Proc. Biolumin. Chemilumin. 9, 1996, 419-422). The virus was amplified in CV-1 cells by addition of virus particles at a multiplicity of infection (MOI) of 0.1 pfu/cell to CV-1 cell monolayers followed by incubation at 37° C. for 1 h with brief agitation every 10 min. At this time, the supernatant fluid with virus particles was removed, and the cell monolayers were washed once with serum free medium. Complete growth medium was then added and the cells were incubated at 37° C. rVV-ruc-gfp virions propagated in CV-1 cells were purified through a sucrose gradient. A plaque assay was used 72 h after infection to determine the titer of recombinant virus by staining the cells with 50% crystal violet solution in ethanol.

(H) Generation of mice carrying tumor implants. To obtain tumors in nude mice, C6 glioma cells were grown, harvested and the cell number was determined by the Trypan Blue exclusion method. Disinfectant was applied to the skin surface, then approximately $5 \times 10^5$ cells were suspended in 100 µl of phosphate buffered saline (PBS) and injected subcutaneously into the right lateral thigh of each mouse. Tumor growth was monitored by recording the size of the tumor with a digital caliper. Tumor volume ($mm^3$) was estimated by the formula (L×H×W)/2, where L is the length, W is the width, and H is the height of the tumor in mm.

Intracerebral glioma tumors were generated by injecting C6 glioma cells into the head of rats. Prior to injection, rats were anesthetized with sodium pentobarbital (Nembutal® Sodium solution, Abbot Laboratories, North Chicago, Ill.; 60 mg/kg body weight). A midline scalp incision (0.5-1 cm) was made, the skin was retracted, and a 1 mm burr hole was made in the skull at a location 2 mm to the left and 2.5 mm posterior to the brigma. Tumor cells were pipetted into an insulin syringe, which was fitted with a 29-gauge needle and mounted in a stereotactic holder. The needle was inserted vertically through the burr hole to a depth of 3 mm. After injection into the brain of $5 \times 10^5$ C6 cells in a 10 µl volume, the needle was kept in place for 15 sec and then withdrawn. The skin incision was closed with surgical clips. Mice bearing subcutaneous prostate tumors were generated over a period of one month following subcutaneous implantation of $3 \times 10^6$ PC3 human prostate cells.

MB-49 human bladder tumor cells were implanted in the C57 mouse bladder to produce animals with bladder tumors. To generate animals with breast cancer (Tian and DeLeon, submitted for publication), female nude mice were first implanted with 0.72 mg/90 day-release 17β-estradiol pellets (Innovative Research, Rockville, Md.) in the skin to facilitate breast tumor development and metastasis. One day after estrogen pellet implantation, $1 \times 10^6$ MCF-7 human breast carcinoma cells transformed with pro-IGF-II (Dull et al., Nature 310 (1984), 777-781) were implanted in the mammary fat pad. For orthotopic transplants, tumors developed from implanted cells were resected and minced into 1-$mm^3$ cubes for tissue transplantation into the mammary fat pad.

(I) Assay of Renilla luciferase in live animals. Mice were anesthetized with Nembutal (60 mg/kg body weight) before every Renilla luciferase assay. Renilla luciferase activities were determined after intravenous injection of a mixture of 5 µl of coelenterazine (0.5 µg/µl diluted ethanol solution) and 95 µl of luciferase assay buffer (0.5 M NaCl; 1 mM EDTA; and 0.1 M potassium phosphate, pH 7.4). Whole live animals were then imaged in a dark box using a Hamamatsu low light video camera, and the images were recorded using Image Pro Plus 3.1 software (Media Cybernetics, Silver Spring, Md.). The pseudocolored photon emission image was superimposed onto the gray scale image of the animal in order to precisely locate the site of light emission.

(J) Fluorescence microscopy of live animals. Mice were anesthesized with Nembutal (60 mg/kg body weight) before tumor visualization. External imaging of GFP expression in live animals was performed using a Leica MZ8 stereo fluorescence microscope equipped with a mercury lamp power supply and a GFP filter (excitation at 470 nm). Images were captured using a SONY DKC-5000 3CCD digital photo camera.

(K) Detection of luminescence and fluorescence. Immediately before imaging, mice and rats were anesthetized with Nembutal® (60 mg/kg body weight). The animals were placed inside the dark box for photon counting and recording superimposed images (ARGUS 100, Hamamatsu, Hamamatsu, Japan). Photon collection was for one minute from ventral and dorsal views of the animals. A light image was then recorded and the low light image was then superimposed over the light image to record the location of luminescent activity.

Imaging of GFP expression in tumors of live animals was performed using a Leica MZ8 stereo fluorescence microscope equipped with a mercury lamp power supply and a GFP filter (excitation at 470 run). Images were captured using a SONY DKC-5000 3CCD digital photo camera.

(L) Histology of tumor tissues. Under anesthesia, the animals were euthanized with an overdose of Nembutal®. The tissues of interest were removed, embedded in Tissue-Tek OCT compound (Miles Scientific, Naperville, Ill.) and immediately frozen in liquid nitrogen without fixation. Frozen sections were cut at −20° C. using a Reichert-Jung Cryocut 1800 cryostat. GFP fluorescence of the tissues was monitored under a Leica fluorescence microscope and the images were recorded using Photoshop software.

EXAMPLE 2

Results Obtained by Intravenous Injection of Recombinant Vaccinia Virus rVV-ruc-gfp into Mice (A) Monitoring of Virus-Mediated Marker Gene Expression in Immunodeficient Mice Vaccinia virus ($1 \times 10^8$ pfu) carrying the Renilla luciferase—GFP fusion expression cassette (rVV-ruc-gfp) was introduced intravenously into nude mice with no tumors. The animals were observed once every 3 days over a two-week time period under the low-light imager to monitor luciferase catalyzed light emission immediately after intravenous injection of coelenterazine, and under a fluorescence microscope to visualize GFP expression. Neither apparent luminescence nor green fluorescence was detected in the animals when imaged externally, except at certain locations that had small skin lesions. Such luminescence and fluorescence signals disappeared after a few days once the lesions had healed. Animals were sacrificed one week and two weeks after viral infection, and their organs were removed and examined for the presence of luminescence and GFP fluorescence signals. One week after viral injection, no luminescence or green fluorescence could be detected in brain, liver, lung, spleen, kidney or testis. These results indicated that the rVV-ruc-gfp virus did not show organ specificity after injection and that the virus seemed to be cleared from the animal by the immune system soon after systemic delivery via the bloodstream.

(B) Visualization of Vaccinia Virus-Mediated Marker Gene Expression in Glioma Tumors of Live Nude Mice The distribution of injected Vaccinia virus in nude mice bearing subcutaneously implanted C6 glioma tumors was examined. Nude mice with tumors approximately 500 mm$^3$ in size were injected intravenously with $1\times10^8$ pfu of the rVVruc-gfp virus. Seven days after virus injection, the animals were monitored for GFP expression under a fluorescence microscope to determine the presence of viral infection and multiplication in the tumors, which had grown to approximately 2500 mm$^3$ in size. Surprisingly, green fluorescence was detected only in the tumor regions in live animals. Seven days after viral injection, the GFP fluorescence was very intensely localized in a patch-like pattern restricted to the tumor region (FIG. 1A-A"). These patches, often seen at the end of blood vessel branches, may have indicated local viral infection of tumor cells that surround the leaky terminals of capillary vessels. During real-time observation of the same tumors, the GFP signal from the center of these patches started to disappear, and new green fluorescent centers appeared in the form of rings at the periphery of the fading patches. The new sites of intense GFP fluorescence may have resulted from progression of the viral infection to nearby cells within the tumor during tumor growth and expansion. After careful examination of the mice, with the exception of the tumor region, no detectable green fluorescence was seen elsewhere on the body surface or in the dissected organs. This experiment clearly showed that a mature solid tumor could be easily localized by the labeled Vaccinia virus, based on light-emission, and it also demonstrated the affinity of virus particles for the tumor tissue.

To determine whether tumor size and vascularization are decisive factors for viral retention in tumors, nude mice were intravenously injected with $1\times10^8$ rVV-ruc-gfp Vaccinia virus particles one day after subcutaneous C6 cell implantation. Surprisingly, 4 days after viral injection GFP expression was seen in 5-day-old C6 tumors that had a volume of about 25 mm$^3$ (FIG. 1B-B"). Examination of labeled Vaccinia virus tumor targeting by visualization of GFP expression in implanted tumors younger than 5 days was not feasible in live mice, since sufficient levels of marker gene expression required approximately 4 days to allow detection under a fluorescence microscope.

Figure 1:
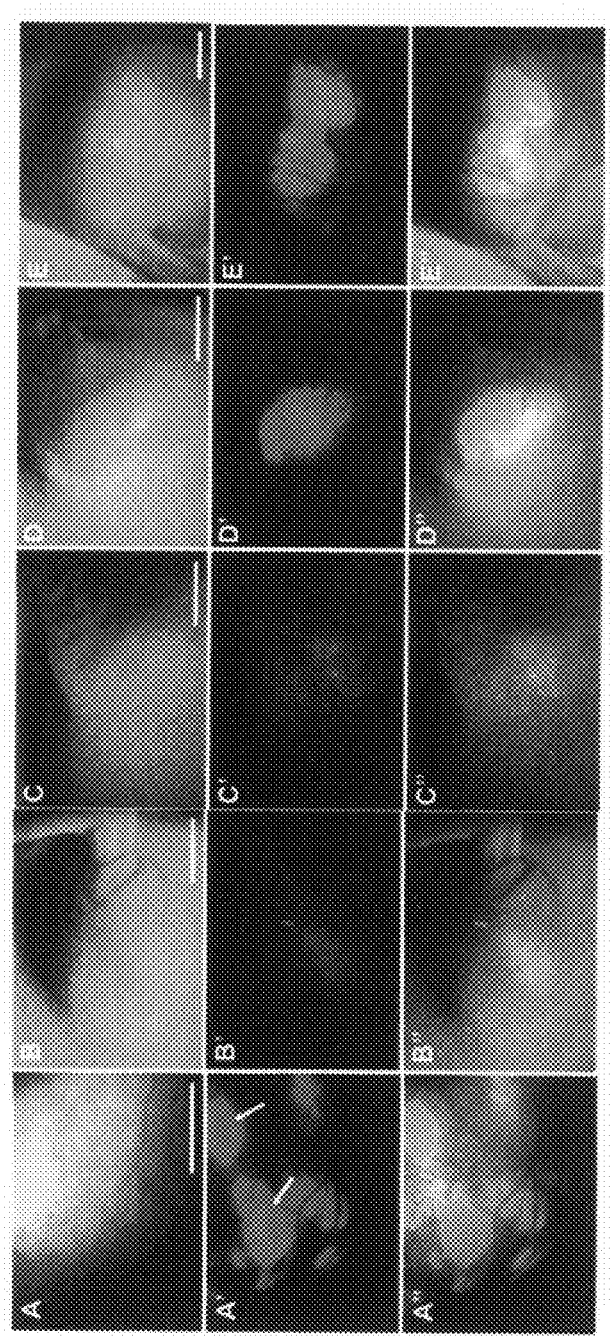
FIG. 1: External Imaging of GFP Expression in Subcutaneous C6 Glioma Tumors in Nude Mice C6 glioma cells ($5\times10^5$) were implanted subcutaneously into the right lateral thigh. At designated days after tumor cell implantation, the animals were infected intravenously with $1\times10^8$ pfu of rVV-ruc-gfp virus particles. GFP expression was monitored under a fluorescence stereomicroscope. Bright field (top), fluorescence (middle), and bright field, fluorescence overlay (bottom) images of subcutaneous glioma tumor are shown. GFP signal can be observed in tumors as small as 22 mm$^3$ in size (B-B"), or as old as 18 days (about 2500 mm$^3$ in size) (A-A"). In older tumors, GFP expression was seen in "patch"-like patterns (indicated by arrows in A'). Marker gene expression in the tumor of the same animal can be monitored continuously 4 (C-C"), 7 (D-D"), and 14 (E-E") days after intravenous viral injection. (Bars=5 mm.)
Figure 2:
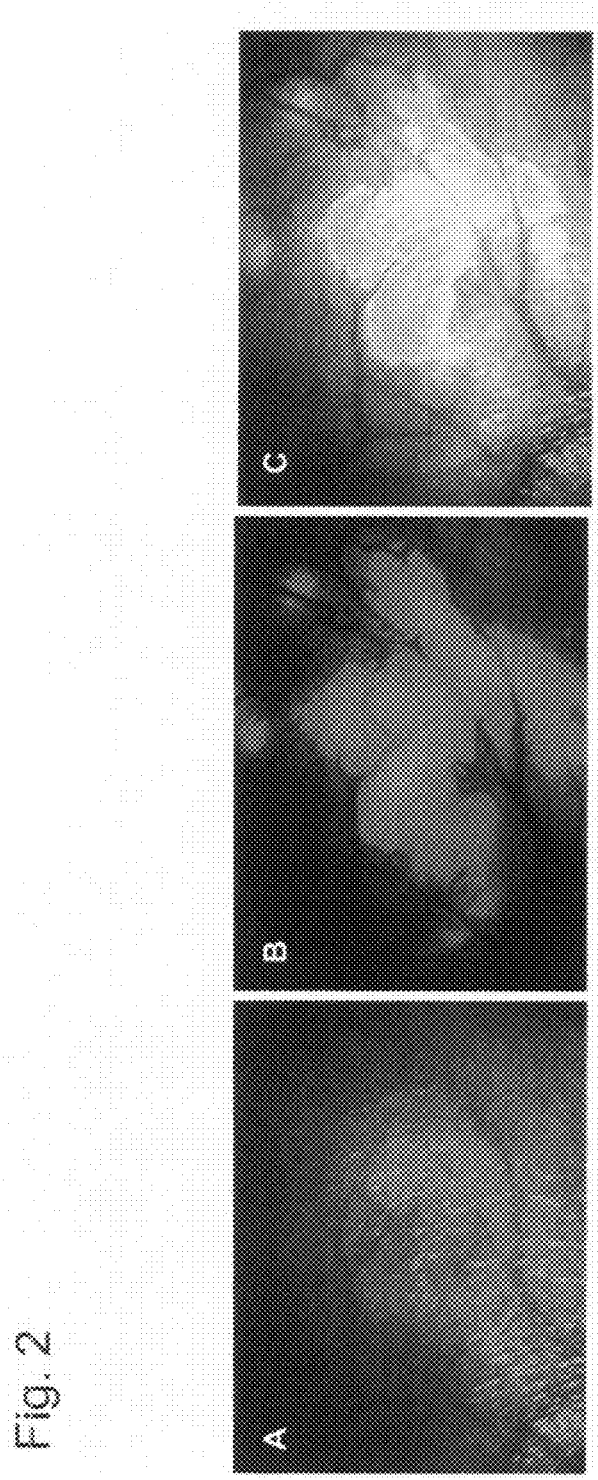
FIG. 2: Visualization of Tumor Angiogenesis

The finding that injection of the rVV-ruc-gfp Vaccinia virus into the bloodstream of the host resulted in GFP expression and accumulation in tumors suitable for non-invasive tumor detection allowed us to follow the entry and replication process of this virus in the same animal in real time (FIG. 1 C-C", D-D" and E-E"). A continuously increasing level of GFP fluorescence was observed in the same animal throughout 20 days following viral injection, which was the time scheduled before sacrificing the animals. Such an increase in detectable fluorescence was indicative of a very strong viral replication in the tumor tissue, the latter appearing to function as a protective immunoprivilaged environment for viral replication. Interestingly, the location of blood vessels and the neovascularization within the periphery of the enlarging tumor were readily visible and confirmed by external visualization against a bright green fluorescent background (FIG. 1A-A", D-D", E-E" and FIG. 2).

To determine the location of viral infection within the tumors, the animals were sacrificed and the skin over the tumor was carefully reflected to expose the tumor. In the exposed tumor, GFP fluorescence was found to be concentrated exclusively in the tumor tissue (FIG. 3B-B" and D-D"). The non-tumorous thigh muscles did not show any fluorescence of viral infection, as indicated by arrows in FIG. 3D-D". The skin overlying the tumor was also non-fluorescent (indicated by asterisks in FIG. 3B-B" and D-D"). Cross sections of the tumor, however, revealed that strong green fluorescent regions were mostly found as patches in the periphery of the tumor (double arrows in FIG. 3C-C") where the actively dividing tumor cells are presumably located.

To further examine the pattern of viral infection in C6 glioma tumors based on GFP expression, the tumor tissues were sectioned for microscopic analysis under the fluorescence microscope. Comparative analysis of various tissue sections revealed that GFP fluorescence was present in large clusters of cells within the tumor (FIG. 4), but no fluorescence was visible in normal tissues such as the heart, lung, liver, spleen, and kidney.

In addition to GFP, the recombinant rVV-ruc-gfp virus carried a second marker gene, which encoded the *Renilla* luciferase in the form of a fusion protein with GFP. Therefore we were able to directly superimpose the site of GFP fluorescence with light emission from *Renilla* luciferase in the tumors. Immediately after coelenterazine (substrate for *Renilla* luciferase) was delivered by intravenous injection, a very strong luciferase activity was recorded only in the tumor region under a low light video camera (FIG. 5). By lowering the sensitivity of the low light video camera to avoid saturation of light detection, we were able to identify the *Renilla* luciferase gene expression in localized patches in the periphery of the tumor. These patch-like patterns precisely correlated with the GFP signals.

(C) Affinity of Vaccinia Virus Delivered to the Bloodstream for Different Tumors Implanted into Animals To determine whether the attraction of the Vaccinia virus was limited to glioma tumors or whether this attraction could be observed in other tumors, recombinant Vaccinia virus was recombinantly introduced into mice that carried different types of implanted tumors. One of these tumor models was a nude mouse with implanted subcutaneous PC-3 human prostate carcinoma. Although the PC3 implants from which tumors developed grew at a much slower rate than the implanted subcutaneous glioma tumors, these tumors showed the same dynamics with regards to Vaccinia virus infection when identical titers ($1\times10^8$) were injected intravenously (FIG. 6A-A"). Similar to our findings with glioma tumors, GFP expression was initially detected 4 days after virus injection, and the fluorescence lasted throughout the 3-week observation period.

Female nude mice with established breast tumors were also used for labeled Vaccinia injections. These breast tumors were allowed to grow for 6 months after the animals received implants of MCF-7 human breast carcinoma cells transformed with pro-IGF-11 cDNA. At the time of Vaccinia virus injection, the tumors had reached maximum growth and the tumor volume (about 400-500 mm$^3$) did not change significantly during the experimental period. Similar to previous experiments, 6 days after intravenous delivery of 1×10$^8$ rVV-ruc-gfp virus particles, strong GFP expression was observed in the breast tumor region (FIG. 6B-B", FIG. 7A-A" and B-B") and nowhere else in the body.

Examination of cross sections of virus-infected breast tumors revealed luminescent "islands" throughout the tumors without any indication of central or peripheral preference of infection (FIG. 7C-C"). The MCF-7 tumor cells used in these breast tumor models are known to metastasize and in addition to the primary solid tumor, a smaller metastasized tumor found on the left lateral side of the body showed GFP fluorescence (FIG. 7D-D", E-E", and F-F"). Excised lung tissues were also examined for detection of metastases. Metastasized tumors as small as 0.5 mm in diameter on the surface of the lung were positive for GFP fluorescence (FIG. 7G-G"). The presence of a strong *Renilla* luciferase-mediated light emission confirmed the expression of the luciferase-GFP fusion protein in these breast tumors but nowhere else in the body when the substrate coelenterazine was injected intravenously into the live animals. These experiments showed that intravenously delivered Vaccinia virus particles were selectively attracted to and replicated in primary and metastasized breast tumors in nude mice, likely as a result of the immunocompromised state of the tumor microenvironment.

To determine whether virus particles could move out of tumors and re-enter the circulation, we injected C6 glioma cells into the thigh of mice to form a second tumor in animals already carrying a breast tumor infected with labeled Vaccinia virus. If the virus particles were released from the tumor to re-enter the circulation in significant numbers they would be able to colonize the newly implanted glioma tumor. Monitoring of these second tumors showed that no GFP signal was visible in the new glioma tumor 7 and 14 days after implantation of the glioma cells. To demonstrate that the newly implanted glioma tumors could be targeted by labeled Vaccinia virus, a second dose of rVV-ruc-gfp virus (1×10$^8$ pfu) was intravenously injected. Five days later, tumor-specific GFP expression was detected in the newly formed glioma tumor in addition to GFP expression seen in the original breast tumor. These findings suggested that the virus particles in infected tumors were either not released back into the circulation at all, or were not released in sufficient numbers to infect and replicate in a second tumor.

Two additional tumor models, including Lewis rats with intracranial C6 rat glioma tumors and C57 mice with MB-49 human bladder tumors in the bladder, were used for Vaccinia injections. To determine whether tumor-affinity of virus particles is a phenomenon limited to tumors in nude mice with a diminished T-lymphocyte function or whether it is a general protective property of tumors that may be demonstrated also in immunocompetent animals, Lewis rats with intracranial C6 rat glioma tumors and C57 mice with MB-49 human bladder tumors in the bladder were used. A total of 5×10$^5$ C6 glioma cells in a 100 µl volume were stereotactically implanted in the brains of 2 of 4 immunocompetent Lewis rats, and the tumors were allowed to grow for 5 days. The other 2 rats were injected intracranially with phosphate-buffered saline to serve as controls. On day six, all 4 rats were intravenously injected with rVV-ruc-gfp virus particles via the femoral vein. Five days after virus injection, all 4 animals were sacrificed, and their brains were carefully excised for analysis by fluorescence microscopy. GFP expression was detected in the brains with implanted intracranial tumors (FIG. 6C-C") while no GFP expression was seen in the control brains. In parallel experiments, C57 mice, with or without bladder tumors, were divided into two groups. One group was injected intravenously with rVV-ruc-gfp Vaccinia virus (1×10$^8$ pfu) and the other with saline solution as control. Five days after virus injection, the animals were sacrificed and examined under the fluorescence microscope. GFP expression was observed in the bladder tumor region in C 57 mice but not in control mice (FIG. 6D-D").

Taken together, these experiments show that Vaccinia virus particles were selectively accumulated and retained in a variety of tumors, probably protected by the tumor microenvironment, and that they were not able to survive in the non-tumorous tissues of immunocompromised as well as immunocompetent animals. The tumor-targeting process by intravenously injected Vaccinia virus carrying the light-emitting dual marker gene demonstrated the ability of the Vaccinia virus system to detect primary and metastatic tumors in live animals.

EXAMPLE 3

Results of Intravenous Injection of Bacterial and Mammalian Light-Emitting Cells into Mice (A) Visualization of Light Emitting Bacteria Present in Whole Animals after Intravenous Injection To determine the fate of intravenously injected luminescent bacteria in the animals, 10$^7$ bacteria carrying the pLITE201 plasmid in 50 µl were injected into the left femoral vein under anesthesia. Following closure of the incision with sutures, the mice were monitored under the low light imager (ARGUS 100 Camera System, Hamamatsu, Hamamatsu, Japan) in real time and photons were collected for one minute. The imaging was repeated in two-day time intervals to determine the presence of light emission from a given animal. It was found that the distribution pattern of light emission following an intravenous injection of bacteria into mice was characteristic of the bacterial strains used. Injection of the attenuated *V. cholera* into the bloodstream resulted in light emission localized in the liver immediately. Injection of *S. typhimurium*, however, was widely disseminated throughout the body of the animal suggesting a difference in the interaction with host cell system (FIG. 8A-8D). Imaging the same animals 24 and 48 hours post-infection showed that all of the detectable light emission from the earlier time diminished rapidly and was eliminated completely from the injected animal. These findings suggest that light emitting bacteria injected into the bloodstream via the femoral vein are cleared. This process was confirmed by photon emission analysis of excised organs, which were found to lack light emission. Similar data were obtained in immunocompetent mice and rats suggesting that the removal of bacteria from the blood is efficient in both systems.

(B) Bacteria Home in on Glioma Tumors in Nude Mice

To determine if bacteria preferentially colonize tumorous tissues, nude mice with ten-day-old tumors (about 500 mm$^3$) in the tight hind leg were injected intravenously via the femoral vein with 10$^7$ *S. typhimurium* or 10$^7$ *V. cholera* in a 50 µl volume of bacterial suspension. Following injection, the incision wounds were sutured and the animals were monitored for six days under the low light imager. At each observation time point, photons were collected for exactly one minute. In mice injected with *S. typhimurium*, luminescent bacteria were disseminated throughout the whole body of the animal similar to the findings in the non-tumorous mice (FIG. 9A). Nude mice injected with *V. cholera*, demonstrated luminescent activity only in the liver region during the early observation period (FIG. 9E). Regardless of the bacterial strain injected, two days after injection, luminescent activity was observed only in the tumor region (FIGS. 9B and 9F). Monitoring of the mice under the low light imager on days four and six post-injection showed decreased amounts of detectable luminescence in the tumors of animals injected with *S. typhimurium* (FIGS. 9C and 9D). This finding was in marked contrast with the findings in the tumors of mice injected with *V. cholera*, which demonstrated not only survival but also propagation of the bacteria in the tumor mass with a dramatic increase in light emission (FIGS. 9G and 9H).

Nude mice bearing subcutaneous human PC3 prostate tumors in the right hind leg were intravenously injected with $10^7$ attenuated *L. monocytogenes* transformed with pS0D-gfp plasmid DNA carrying the gfp cDNA. GFP fluorescence was observed under a fluorescence stereomicroscope. Twenty-seven hours after bacterial injection, GFP signal was detected only in the tumor region (FIG. 14). No GFP signal was observed in the rest of the animal.

(C) Determination of Minimum Size and Age of Glioma Tumors Necessary for Bacterial Infection.

The purpose of this experiment was to determine whether the size of the tumor has any influence on its ability to be colonized by bacteria. Tumors were induced in the right hind leg of nude mice by subcutaneous injection of glioma cells as described. On days 0, 2, 4, 6, 8, and 10 of tumor induction, attenuated *S. typhimurium* and *V. cholera* with the pLITE201 plasmid were injected intravenously through the femoral vein. Presence of luminescent bacteria in the tumor was determined by photon collection for exactly one minute under the low light imager two and four days post-infection. The tumor volume was also determined by measuring the dimensions with a digital caliper. The earliest time-point when luminescent activity was noted in the tumors was on day eight after tumor induction. Corresponding tumor volumes were approximately 200 mm$^3$.

(D) Bacteria Home in on Breast Tumors of Nude Mice

In order to determine whether colonization of tumors is limited to glioma cells or whether this is a general phenomenon observed with all tumors, female nude mice baring tumors in the right breast pad were intravenously injected with $10^7$ *V. cholera* in a 50 µl volume of bacteria suspension. The animals were monitored within the first 10 minutes after inoculation under the low light imager for one minute and demonstrated the typical luminescent pattern in the liver region (FIG. 10A). Two days later, while the liver had become clear of luminescent bacteria, the breast tumor was colonized by the labeled *V. cholera*. In addition to the main tumor, a metastatic tumor in the left breast demonstrated luminescent activity (FIG. 10B). On day five, the animals had cleared the bacteria that colonized the incision wound, however, the tumors remained luminescent (FIG. 10C). FIG. 10D shows the continued colonization and propagation of the bacteria in the main tumor, while the metastatic, smaller tumor had become cleared. Luminescent activity continued for over 45 days in the right breast tumor. Similar experiments were conducted using *E. coli* to demonstrate that homing in of tumors by bacteria is not strain dependent (FIGS. 10E and 10F).

To determine whether the bacteria from the tumor enter the blood circulation in significant quantities to colonize other sites, a second tumor (C6 glioma) was induced in these animals in the right hind led. The tumor was allowed to grow for 10 days. No luminescent activity was observed in the glioma tumor demonstrating the absence of a significant bacteria that would cause colonization of this tumor. However, when the animal was rechallenged with $10^7$ attenuated *V. cholera* intravenously, the leg tumor showed strong luminescent activity.

The findings of these experiments demonstrate that larger tumors retain bacteria more effectively over time. Furthermore, the bacteria within the tumors do not escape into the blood in sufficient quantities to infect susceptible sites such as other tumors.

(E) Bacteria Home in on Bladder Tumors in Immunocompetent Mice

C57 mice were intravenously injected with $10^7$ attenuated *V. cholera* transformed with pLITE201 encoding the lux operon. On day nine after bacterial delivery, luminescent activity was recorded by photon collection for one minute under the low light imager. Light emission was noted in the bladder region of the whole animal (FIG. 11A). The animals were sacrificed and an abdominal incision was made to expose the bladder. Luminescent activity was positively confirmed to be limited to the bladder (FIG. 11B). Upon removal of the bladder from the mice, luminescent activity was no longer visible anywhere in the animals, however, the excised bladders continued to demonstrate light emission (FIG. 11C). Based on the results of this experiment, bacteria can target tumors in immunocompetent as well as nude mice. Furthermore, the bacteria can also target smaller tumors.

(F) Bacteria Home in on Glioma Tumors in the Brain of Rats

Lewis rats with glioma tumors in the brain were intravenously injected with $10^8$ attenuated *V. cholera* with the pLITE201 plasmid through the left femoral vein to determine if bacteria can cross the blood-brain barrier and target tumors in immunocompetent animals. The whole animals were monitored for one minute under the low light imager the following day and low levels of luminescent activity was observed through the skull. The rats were sacrificed and the brain tissue was removed in one piece in order to further evaluate the exact location of the luminescent bacteria. Visualization of the excised brain under the imager demonstrated strong luminescent activity in specific regions of the brain (FIG. 12A). Similar imaging of control rats without brains tumors, which were intravenously injected with the labeled bacteria, demonstrated absence of any luminescent activity (FIG. 12B).

(G) Transformed Human Fibrosarcoma Cells Home in on Subcutaneous Glioma Tumors in Nude Mice Nude mice with human breast tumors were injected intravenously with $5 \times 10^5$ human fibrosarcoma cells, which were permanently transformed with retrovirus derived from pLEIN. Seven days post-injection, the animals were anesthetized with Nembutal, and monitored under a fluorescent stereomicroscope. Fluorescent cells were noted only in the tumor region of the whole mice through the skin (FIG. 10A1-3). Upon exposure of the tumor tissues by reflection of the overlying skin (FIG. 10B1-3), and in cross sections of the tumors (FIG. 10C1-3), fluorescent patches were visible in distinct regions. Close examination of the organs of the mice showed the presence of small clusters of fluorescent cells in the lungs of the animals, demonstrating the affinity of the fibrosarcoma cells for the lungs in addition to the tumorous tissue.

EXAMPLE 4

Construction of Bacterial Plasmid Vectors that Carry the Light-Emitting Protein Encoding Expression Cassettes and the Therapeutic Gene Expression Constructs in Cis Configuration (A) Rationale Using the light-emitting expression systems described above, tumors could be imaged based on light emission for up to 45 days in animals. These findings suggest a remarkable plasmid DNA stability in bacteria in the absence of selection. Therefore, by placing the therapeutic gene cassette in cis configuration with the light-emitting protein expression cassette on the same replicon, light emission can be used as an indicator of therapeutic construct presence and stability.

In contrast to light-emitting proteins, the therapeutic proteins, endostatin and *Pseudomonas* exotoxin/TGF alpha fusion protein, are required to be-secreted from the bacteria into the medium or into the cytosol of tumor cells for inhibition of tumor growth. To achieve protein secretion from the extracellularly replicating *E. coli* cells into the tumor, two constructs with different signal sequences can be designed. For secretion of endostatin, the ompF signal sequence can be placed upstream of the coding sequence of endostatin, which facilitates the secretion into the periplasmic space. To release the endostatin into the medium, an additional protein, the PAS protein, needs to be coexpressed with endostatin. PAS has been shown to cause membrane leakiness and the release of secreted proteins into the medium (Tokugawa et al., J. Biotechnol. 37 (1994), 33; Tokugawa et al., J. Biotechnol. 35 (1994), 69). The second construct for the secretion of *Pseudomonas* exotoxin/TGF alpha fusion protein from *E. coli* has the OmpA signal sequence upstream of the fusion gene and the release from the periplasmic space into the medium is facilitated by sequences present in domain II of the exotoxin (Chaudhary et al., PNAS 85 (1988), 2939; Kondo et al., J. Biol. Chem. 263 (1988), 9470; Kihara and Pastan, Bioconj. Chem. 5 (1994), 532). To promote secretion of endostatin and *Pseudomonas* exotoxin/TGF alpha fusion protein from *L. monocytogenenes*, the signal sequence of listeriolysin (LLO) (Mengaud et al., Infect. Immun. 56 (1988), 766) can be placed upstream of each coding sequence.

For regulation of endostatin and *Pseudomonas* exotoxin/TGF alpha fusion protein expression levels in bacteria, vectors can be generated where the therapeutic protein encoding genes are under the control of the T7 promoter or the $P_{spac}$ synthetic promoter (Freitag and Jacobs, Infect. Immun. 67 (1999), 1844). Without exogenous induction, the levels of the therapeutic proteins are low in *E. coli* and in *L. monocytogenes*. The minimal levels of therapeutic proteins in bacteria provide greater safety following intravenous injection of the engineered bacteria. In the following, six newly constructed plasmid DNAs for constitutive and regulated expression of endostatin and *Pseudomonas* exotoxin/TGF alpha fusion protein in *E. coli* and *L. monocytogenes* are described. All plasmids to be transferred into *E. coli* will carry the constitutively expressed bacterial lux operon, and all the plasmids to be transferred into *L. monocytogenes* will carry the constitutively expressed sod-gfp cassette. Plasmids BSPT#1-ESi and BSPT#2-Pti are able to replicate in *E. coli* only, and plasmids BSPT#3, #4, #5, and #6 replicate in *E. coli* and *L. monocytogenes*.

(B) Construction of Plasmid Vectors for Protein Expression and Secretion from *E. coli*

The construction of the endostatin secretion vector to be used in *E. coli* is as follows. The coding sequence of human endostatin (591 bp) will be amplified by PCR from the plasmid pES3 with the introduction of the required restriction sites on both ends, followed by ligation into a pBluescript (Clontech Corp., USA) cloning vector to generate pBlue-ES. The ompF signal sequence (Nagahari et al., EMBO J. 4 (1985), 3589) is amplified with Taq polymerase and inserted upstream in frame with the endostatin sequence to generate pBlue-ompF/ES. The expression cassette driven by the T7 promoter will be excised, and inserted into the pLITE201 vector described in Example 1(B), above, carrying the lux-CDABE cassette, to produce the plasmid pLITE-ompF/ES. The sequence encoding the PAS factor (a 76 amino acid polypeptide) will be amplified from the chromosomal DNA of *Vibrio alginolyticus* (formerly named *Achromobacter iophagus*) (NCIB 11038) with Taq polymerase using the primers 5'-GGGAAAGACATGAAACGCTTA3-' (SEQ ID NO: 1) and 5'-AAACAACGAGTGAATTAGCGCT-3' (SEQ ID NO: 2), and inserted into the multiple cloning sites of pCR-Blunt (Clontech Corp., USA) to create the expression cassette under the control of the lac promoter. The resulting plasmid will be named pCR-PAS. The lac promoter linked to the pas gene will be excised from pCR-PAS and inserted into pLITEompF/ES to yield the final plasmid BSPT#1-ESI.

Plasmid pVC85 (Pastan, see above) contains a T7 promoter, followed by an ompA signal sequence, and a sequence encoding domain II and III of *Pseudomonas* exotoxin (PE40). The DNA sequence encoding PE40 will be excised with restriction enzymes and replaced with a fragment of PE37/TGF alpha (*Pseudomonas* exotoxin A 280-613/TGF alpha) obtained from the plasmid CT4 (Pastan, see above) to create the plasmid pVC85-PE37/TGF alpha. The expression cassette of ompAPE37/TGF alpha linked to the T7 promoter will be excised and inserted into pLITE201 to yield the final plasmid BSPT#2-PTI.

(C) Construction of Plasmid Vectors for Protein Expression and Secretion from *L. monocytogenes*

Genes encoding endostatin or PE37/TGF alpha will be inserted downstream of the listeriolysin (LLO) signal sequence in the plasmid pCHHI to generate pCHHI-ES and pCCHI-PE37/TGF alpha. Constitutive expression of the therapeutic proteins will be obtained by linking the above secretion cassettes to the listeriolysin promoter obtained from the pCHHI vector. The SOD-GFP expression cassette, excised from the plasmid pSOD-GFP (Gotz et al. PNAS in press.) will be inserted into pCHHI-ES to generate BSPT#3-ESc, and into pCCHI-PE37/TGF alpha to generate BSPT#4-PTc. For the expression of the therapeutic proteins under the control of an IPTG inducible promoter, the listeriolysin promoter in BSPT#3-ESc and BSPT#4-PTc will be replaced with the $P_{spac}$ promoter from the plasmid pSPAC (Yansura and Henner, PNAS USA 81 (1984), 439) to generate BSPT#5-ESi and BSPT#6-PTi. $P_{spac}$ is a hybrid promoter consisting of the *Bacillus subtilis* bacteriophage SPO-1 promoter and the lac operator. IPTG-induced GFP expression from the $P_{spac}$ promoter has been documented in *L. monocytogenes* in the cytosol of mammalian cells.

EXAMPLE 5

Demonstration of the Expression of Luciferase and GFP in Bacteria and Verification of the Secretion of Endostatin and Recombinant Toxin/TGF Alpha Fusion Protein and their Function in Cell Culture Assays To be able to detect the presence of *E. coli* and *L. monocytogenes* in tumor tissues in live animals, the levels of the constitutively expressed luciferase and GFP in bacteria need to be adequate. Therefore, after transformation of recipient *E. coli* or *L. monocytogenes* with the constructs described in Example 4, the colonies with the highest luciferase light emission or OFP fluorescence will be selected. In addition to characterizing light emission from each selected colony before intravenous injection, the ability of the selected transformants to secret endostatin and *Pseudomonas* exotoxin/

TGF alpha fusion protein into the medium needs to be confirmed. The presence of endostatin and *Pseudomonas* exotoxin/TGF alpha fusion protein synthesized within *E. coli* and *L. monocytogenes* will be determined by extracting these proteins from the cell pellet. The secreted proteins in the medium will be concentrated and analyzed by gel separation and the quantity will be determined by Western blotting. It is imperative to determine the percentage of the newly synthesized proteins expressed from each plasmid construct in either *E. coli* or *L. monocytogenes* that is present in the medium. It is also essential to confirm, in addition to constitutive expression of endostatin and *Pseudomonas* exotoxin/TGF alpha fusion protein, that expression can be induced in *E. coli* and in *L. monocytogenes* upon the addition of IPTG to the bacterial culture medium. For the design of future tumor therapy protocols, the relative amounts of protein secreted by the constitutive expression system needs to be compared to the induced expression levels for a defined time period first in bacterial cultures. It is equally essential to determine that both proteins when synthesized in *E. coli* and *L. monocytogenes* are biologically active if generated from the proposed constructs. Both proteins were synthesized previously in *E. coli* and were shown to be active.

The results of the experiments described below should confirm whether endostatin is successfully secreted from *E. coli* using the OmpF signal peptide in combination with PAS pore forming protein expression. These experiments will also show if the PE40/TGF alpha and PE37/TGF alpha fusion proteins are secreted from bacteria using the OmpA signal peptide in combination with domain II of PE. Further, the listeriolysin signal peptide may also facilitate the secretion of endostatin and the chimeric toxin/TGF alpha fusion protein into the medium as well as into the cytosol of infected tumor cells. Using the migration inhibition assay and the protein synthesis inhibition assay, it can be expected to determine that both proteins secreted into the medium are biologically active. The presence and quantities of these proteins may be regulated by replacing the constitutive promoters with promoters that can be induced by IPTG.

In addition to the secretion system described below, alternative secretion systems such as the *E. coli* HlyBD-dependent secretion pathway (Schlor et al., Mol. Gen. Genet. 256 (1997), 306), may be useful. Alternative secretion signals from other gram positive bacteria, such as the *Bacillus* sp. endoxylanase signal peptide (Choi et al., Appl. Microbiol. Biotechnol. 53 (2000), 640; Jeong and Lee, Biotechnol. Bioeng. 67 (2000), 398) can be introduced.

(A) Confirmation of Endostatin and *Pseudomonas* Exotoxin/TGF Alpha Fusion Protein Secretion from Bacteria into Growth Medium

*E. coli* strains (DH5α and BL21(λDE3)) will be transformed with BSPT#1-ESi and BSPT#2-PTi plasmid DNA. *L. monocytogenes* strain EGDA2 will be transformed with plasmids BSPT#3-ESc, BSPT#4-PTc, BSPT#5-ESi, and BSPT#6-PTi individually. After plating on appropriate antibiotic-containing plates, individual colonies will be selected from each transformation mixture. These colonies will be screened under a low light imager and fluorescence microscope for luciferase and GFP expression, respectively. Three colonies with the most intense light emission from each transformation batch will be chosen for further studies. To verify the secretion of endostatin and *Pseudomonas* exotoxin/TGF alpha fusion protein from each selected transformant, the cells will be grown in minimal medium to log phase. After centrifuging down the bacteria, the supernatants will be passed through a 0.45-μm-pore-size filter, and the bacterium-free medium will be used for precipitation of the secreted proteins. The precipitates will be collected by centrifugation. Pellets will be washed, dried, and re-suspended in sample buffer for protein gel separation. Proteins from aliquots corresponding to 10 μl of bacterial culture will be compared to proteins from 200 μl of culture supernatant after separation in a 10% SDS-polyacrylamide gel. Western blot analysis will be performed using polyclonal antibody against endostatin (following the antibody production protocol described by Timpl, Methods Enzymol. 82 (1982), 472) and monoclonal antibody against TGF alpha (oncogene Research Products, Cambridge, Mass., USA). The optimal growth conditions will be established for secretion by sampling the growth medium at different times during growth. A similar method has been used previously to analyze secreted proteins in *Salmonella typhimurium* culture supernatant (Kaniga et al., J. Bacteriol. 177 (1995), 3965). By use of these methods the amount of secreted proteins in the bacterial culture medium generated by each of the constructs without induction will be established. To estimate the increase in the amount of secreted proteins in the medium, IPTG-dependent promoter activation experiments will be carried out by adding IPTG to the bacterial culture in log phase for 3 to 6 hours, and the secreted proteins will be assayed as above.

(B) Verification of the Biological Activity of Endostatin Secreted by *E. coli* and *L. monocytogenes* Using a Migration Inhibition Assay It has been shown that endostatin inhibits vascular endothelial growth factor (VEGF)-induced human umbilical vein endothelial cell (HUVEC) migration. Thus, the biological activity of endostatin secreted by bacteria can be tested using the HUVEC migration assay provided by Cascade Biologics, Portland, Oreg. The inhibition of cell migration will be assessed in 48-well chemotaxis chambers (Neuro Probe, Gaithersburg, Md.) (Polverine et al., Methods Enzymol. 198 (1991), 440). Bacterium-free supernatant from each secretion construct will be added to HUVECs for preincubation for 30 min. After incubation, the HUVECs will be placed in the upper chamber. The migration of HUVECs into the lower chamber induced by $VEGF_{165}$ (R&D Systems, Minneapolis, Minn.) will be quantified by microscopic analysis. The concentration of functional endostatin in the medium will be directly proportional to the degree of inhibition of HUVEC migration.

(C) Testing the Cytotoxic Activity of Secreted Recombinant PE Toxin Tumor in Tumor Cell Cultures The inhibitory activity of the chimeric toxin in mammalian cells will be measured based on inhibition of de novo protein synthesis by inactivating EF-2 (Carroll and Collier, J. Biol. Chem. 262 (1987), 8707). Aliquots of bacterium-free supernatants obtained from the expression of various recombinant PE secretion constructs in *E. coli* and in *L. monocytogenes* will be added to the C6 glioma cells or to HCTI 16 colon carcinoma cells. Following treatment with medium, the mammalian cells will be pulsed with [$^3$H]-leucine, and the incorporation will be determined in the protein fraction. To determine the presence of secreted chimeric toxin proteins in *L. monocytogenes*-infected mammalian cells, the bacteria will be eliminated from the medium by gentamicin treatment. The mammalian cells containing *L. monocytogenes* in the cytosol will be lysed, and the released bacteria removed from the lysate by filtration. The mammalian cell lysate containing the secreted chimeric toxins will be assayed in protein synthesis inhibition experiments. The inhibition of [$^3$H]-leucine incorporation in tumor cell culture will be directly proportional to the amount of the biologically active chimeric toxin protein in the medium and cell lysate.

23

EXAMPLE 6

Determination of the Entry, Localization and Distribution of Intravenously Injected Bacteria in Tumors of Live Animals (A) Rationale Since only a small number of intravenously injected bacteria escape the immune system by entering the tumor, their immediate localization is not possible due to limited light emission in live animals. Their location can only be verified by sectioning the tumor to identify the early centers of light emission. Looking at sections at a later time point, bacteria can be seen throughout the entire tumor due to rapid replication. To determine whether one or multiple bacteria enter through the same site, red fluorescent protein can be used to label the extracellularly replicating *E. coli* and green fluorescent protein for the intracellularly replicating *L. monocytogenes*. By visualizing the distribution of the red and green fluorescence in tissue sections, the entry sites as well as replication and localization of *E. coli* and *L. monocytogenes* can be determined individually and simultaneously in the central or peripheral regions of the tumor. It can be expected that the patterns of entry and distribution obtained in implanted tumors mimic those of spontaneous tumors, accordingly, the bacterium-based diagnosis and protein therapy will become a valid approach.

With the experiments described in section (B), below, the entry, replication, and distribution of light-emitting bacteria in spontaneous tumors can be compared to the distribution patterns in implanted tumors. Further, double-labeling experiments will allow the operator to precisely locate the extracellularly replicating *E. coli* and the intracellularly replicating *L. monocytogenes* in the same tumor sections. Lastly, it can be determined (subsequent to a five-day bacterial colonization) whether bacteria are distributed evenly in the tumors or preferential localization occurs in the periphery of the tumor or in the necrotic center. A possible reduction in bacterial entry into spontaneously occurring tumors due to the immunocompetence of these animals can be overcome by increasing the number of intravenously injected bacteria.

(B) Intravenous Injection of *E. Coli* Expressing Red Fluorescent Protein and *L. monocytogenes* Expressing Green Fluorescent Protein into Nude Mice and into Rodents with Implanted and Spontaneous Tumors

*E. coli* (DH5α) carrying the DsRed (Matz et al., Nat. Biotech. 17 (1999), 969) expression cassette under the control of a constitutive promoter are used in this experiment. *L. monocytogenes* EGD strain derivatives with in-frame deletion in each of the virulence genes were individually labeled with the green fluorescent protein cassette driven by the constitutive SOD promoter.

The localization and intratumoral distribution of bacteria will first be studied in nude mice with implanted C6 glioma or HCT116 colon carcinoma tumors. C6 glioma or HCT116 colon carcinoma cells ($5\times10^5$ in 100 µl) will be subcutaneously injected into the right hind leg of the animals. Twelve days after tumor cell injection, the animals will be anesthetized, and the left femoral vein surgically exposed. Light-emitting bacteria ($1\times10^6$ cells re-suspended in 50 µl of saline) will be intravenously injected, and the wound incision will be closed with sutures. Tumors will be measured three times a week using a caliper. Tumor volume will be calculated as follows: small diameter×large diameter×height/2.

Intracerebral glioma tumors will be generated by injecting C6 glioma cells into the head of Wistar rats. Rats will be anesthetized with Ketamine (70-100 mg/kg body weight) and Xylazine (8-10 mg/kg body weight). A midline scalp incision (0.5-1 cm) will be made, skin will be reflected, and a 1 mm burr hole will be made in the skull located 2 mm to the left and 2.5 mm posterior to the brigma. Tumor cells will be pipetted into an insulin syringe fitted with a 29-gauge needle and mounted in a stereotactic holder. The needle will be inserted vertically through the burr hole to a depth of 3 mm. After injection into the brain of a 5 µl volume of either $5\times10^5$ C6 cells or PBS as control, the needle will be kept in place for 15 sec and then withdrawn. The skin incision will be closed with surgical clips. Ten days after cell injection, an intracranial glioma will develop which is 5-10 mm in diameter. The same protocols involving intravenous injection of bacteria into animals with tumors will be followed through the reminder of the proposal.

The localization of bacteria in the tumor, based on GFP or RFP, will also be analyzed using cryosectioned tumor tissues. A reliable morphological and histological preservation, and reproducible GFP or RFP detection may be obtained using frozen sections after a slow tissue freezing protocol (Shariatmadari et al., Biotechniques 30 (2001), 1282). Briefly, tumor tissues will be removed from the sacrificed animals to a Petri dish containing PBS and dissected into the desired size. The samples will be mixed for 2 h in 4% paraformaldehyde (PFA) in PBS at room temperature. They will be washed once with PBS, and embedded in Tissue-Tek at room temperature, and then kept in the dark at 4° C. for 24 h and slowly frozen at −70° C. Before sectioning, the tissue will be kept at −20° C. for 30 min. Then, 10- to 50-µm-thick sections will be cut with a Reichert-Jung Cryocut 1800 cryostat and collected on poly-L-lysine (1%)-treated microscope slides. During sectioning, the material will be kept at room temperature to avoid several freezing and thawing cycles. Finally, the sections will be rinsed in PBS and mounted in PBS and kept in the dark at 4° C.

To monitor the entry of light emitting *E. coli* and *L. monocytogenes* from the blood stream into the tumor, 27 nude mice will be injected with C6 tumor cells, and 27 nude mice with HCT116 colon carcinoma cells. Twelve days after tumor development, 9 animals from the C6 group and 9 from the HCT116 group will receive an intravenous injection of *E. coli* with the RFP construct. Another 9 animals from each group will receive an intravenous injection of *L. monocytogenes* transformed with the GFP construct. The third group of 9 animals from each tumor model will receive both *E. coli* and *L. monocytogenes* ($1\times10^6$ cells of each). Five hours, 25 hours, and 5 days after injection, three animals of each treatment group will be sacrificed, their tumors excised, and processed individually as described in the above cryosectioning protocol. After freezing, each tumor will be cut into two halves. One half of the tumor will be used for preparing thick sections (60-75 µm), which will be analyzed under a fluorescence stereomicroscope to observe the distribution of bacteria in the sections of tumors obtained from each time point of the experiment. The regions of interest will be identified, thin sectioned, prepared, and analyzed with laser scanning cytometry and under the confocal microscope followed by image reconstruction.

In parallel experiments, animals with spontaneous tumors, as listed in Table 1, will be obtained and used in intravenous injection experiments with *E. coli* carrying the bacterial lux operon. Two animals of each tumor model will be used, and the luciferase light emission monitored daily under the low light imager. It is expected that the spontaneously occurring tumors can be imaged similarly to the implanted tumors based on bacterial luciferase expression. Two of the spontaneous tumor models, mice with adenocarcinoma of the large intestine and mice with adenocarcinoma of the mammary tissue, will be used for bacterial localization experiments following intravenous injection of *E. coli* expressing RFP and *L. monocytogenes* expressing GFP as described above. It can be expected that these experiments will emphasize the significance of the bacterium-based diagnosis and protein therapy system.

TABLE 1

Spontaneous tumor animal models

| Animal species | Strain name | Tumor description | Source | References |
|---|---|---|---|---|
| Mouse | 129/Sv-Madh3$^{tm1par}$ | spontaneous adenocarcinoma of large intestine | Jackson Laboratories Bar Harbor, ME | Zhu et al., Cell 94 (1988), 703 |
| Mouse | FVB/N-TgN(UPII-SV40T) 29Xrw | spontaneous carcinoma of bladder with metastasis to the liver | Jackson Laboratories Bar Harbor, ME | Zhang et al., Cancer Res. 59 (1999), 3512 |
| Mouse | FVB-NeuN (N#202) | spontaneous adenocarcinoma of mammary tissue | Jackson Laboratories Bar Harbor, ME | Guy et al., PNAS USA 89 (1992), 10578 |
| Rat | F344/CrCrlBR | spontaneous carcinoma of pituitary | Charles River Laboratories Wilmington, MA | Hosokawa et al., Toxicol. Pathol. 21 (1993), 283 |

EXAMPLE 7

Verification of Bacterium-Mediated Tumor Targeting and Bacterium-Secreted Protein Therapy in Rodents with Implanted or Spontaneous Tumors (A) Rationale As shown in the previous examples, intravenous injection of light-emitting bacteria results in entry, replication, and accumulation only in the tumor regions in animals. This process can be monitored by imaging of light emission in tumors. Placing the endostatin and chimeric toxin expressing gene cassettes in cis configuration with a light-emitting gene cassette provides an indirect detection system in vivo for their temporal and spatial delivery via bacteria.

The endostatin and chimeric toxin gene cassettes are linked to signal peptide encoding sequences, which facilitate the secretion of these proteins into the extracellular space in the tumor or into the cytosol of infected tumor cells. Both proteins secreted from bacteria into the extracellular space of the tumor are expected to function similarly to directly injected purified proteins. Both proteins secreted from *L. monocytogenes* into the cytosol of the infected tumor cells will resemble the viral delivery system reported earlier for endostatin. The bacterial systems can be used as a constitutive secretion system or as an exogenously added IPTG-activatable secretion system in the tumor. By regulating the expression levels of the therapeutic proteins in bacteria that colonize the tumor, the secreted amount of proteins inhibiting tumor growth can be determined. Without the addition of IPTG, the inhibitory protein secretion from the intravenously injected bacteria will be kept at minimum while in blood circulation. This will provide an added safety to the recipient tumorous animals during delivery of bacteria. Using the BSPT system, the onset and duration of the therapy can be controlled by the addition of IPTG. Upon completion of the treatment, the bacterial delivery system can be eliminated by administration of antibiotics, similar to treating a bacterial infection.

(B) Determination of the Effect of Endostatin and *Pseudomonas* Exotoxin/TGF Alpha Fusion Protein Secreted by *E. coli* and *L. monocytogenes* on Tumor Growth in Animals with Implanted Tumors The inhibitory effect of endostatin and the cytotoxicity of the chimeric toxin secreted by *E. coli* and *L. monocytogenes* in tumors will be determined as follows. Thirty-five nude mice bearing 10-day-old C6 tumors will be injected with bacterial constructs as follows: (a) Five mice with *E. coli* engineered to secrete endostatin; (b) Five mice with *E. coli* engineered to secrete chimeric toxin; (c) Five mice with *L. monocytogenes* engineered to secrete endostatin; (d) Five mice with *L. monocytogenes*-engineered to secrete chimeric toxin; (e) Five mice with *E. coli* secreting endostatin and chimeric toxin; (f) control group: five mice injected with *E. coli* expressing bacterial luciferase alone, and five mice with *L. monocytogenes* expressing GFP. At the time of bacteria injection, each tumor volume will be determined. Three days after injection, the replication of bacteria in the tumors will be monitored under a low light imager or under a fluorescence stereomicroscope. The light emission and the tumor volume will be measured daily up to 20 days after bacterial injection. Ten days after injection, one animal from each group will be sacrificed and the levels of the secreted proteins present in the tumor tissue will be analyzed using Western blot analysis. These experiments will result in inhibition of tumor growth in endostatin treated animals or a more dramatic tumor regression in animals treated with chimeric toxin proteins. The tumor growth in control animals is not expected to be affected by the bacteria alone.

In a follow-up experiment, mice with spontaneous adenocarcinoma of mammary tissue (strain FVB-neuN(N#202), Table 1) will be used to study the effect of secreted proteins on tumor growth. An experimental scheme identical to that described for the C6 tumor analysis will be used. At the completion of tumor therapy, the presence of endostatin or chimeric toxin in the tumor tissue will be determined by Western blot analysis. An identical experimental design will be used to assay the effect of IPTG-induction of endostatin and chimeric toxin production in bacteria in C6 tumors as well as in the spontaneously occurring breast tumor mouse model. It is expected that multiple IPTG induction of protein expression in bacteria might be required for successful tumor therapy.

At any stage of tumor treatment, it may be required to remove the light emitting and therapeutic gene containing bacteria from the animal. To carry out this experiment, mice with 12-day-old C6 tumors will be intravenously injected with *E. coli* expressing the bacterial luciferase. Three days after injection, antibiotic therapy will be initiated by intraperitoneal administration of gentamicin (5 mg/kg body weight) twice daily, or the newly discovered clinafloxacin (CL960) (Nichterlein et al., Zentralbl. Bakteriol. 286 (1997), 401). This treatment will be performed for 5 days, and the effect of antibiotics on the bacteria will be monitored by imaging light emission from the animals daily.

By completing the above experiments, it is expected that endostatin and chimeric toxin proteins secreted into the tumors will cause the inhibition of tumor growth and measurable tumor regression. It is anticipated that tumor regression will be achieved in both groups of rodents with implanted tumors and with spontaneously occurring tumors. Experiments with simultaneous application of secreted endostatin and chimeric toxin proteins in tumor treatment may give the most promising results. The removal of the engineered bacteria from the tumor by administration of antibiotics is an added safety measure of the bacterium-secreted protein therapy (BSPT) of the present invention.

That which is claimed is:

1. A method of tumor therapy, comprising:
intravenously administering a Lister strain vaccinia virus to a tumor bearing subject, wherein the Lister strain vaccinia virus replicates and accumulates in the tumor and is recognized by the immune system of the subject, resulting in regression of a tumor in the subject.

2. The method of claim 1, wherein the vaccinia virus comprises DNA encoding a protein or proteins for tumor therapy or elimination of metastatic tumors or both.

3. The method of claim 2, wherein the protein for tumor therapy or elimination of metastatic tumors or both is selected from among a cytotoxic protein, a cytostatic protein, an inhibitor of angiogenesis, a protein that stimulates apoptosis, a protein that inhibits an elongation factor, a protein that binds to a ribosomal subunit, a nucleotide-modifying protein, a nuclease, a protease, a cytokine, a toxin, an enzyme, and a receptor.

4. The method of claim 3, wherein the protein is selected from among endostatin, chimeric toxin PE37/transforming growth factor alpha (TGF α), a protein that converts a non-toxic prodrug into a cytotoxic drug, *Pseudomonas* exotoxin, interleukin 2, interleukin 12 and glucuronidase.

5. The method of claim 2, wherein the virus contains DNA encoding a detectable protein or a protein that induces a detectable signal, and the method further comprises monitoring tumor therapy.

6. The method of claim 1, wherein the virus contains DNA encoding a detectable protein or a protein that induces a detectable signal, and the method further comprises monitoring tumor therapy.

7. The method of claim 6, wherein the protein is a luminescent or fluorescent protein or is a protein that induces a signal detectable by magnetic resonance imaging (MRI) or binding to a contrasting agent, chromophore or a ligand for visualization of tissues.

8. The method of claim 7, wherein the detectable protein or protein that induces a detectable signal is a luciferase, a red fluorescent protein (RFP) or a green fluorescent protein (GFP).

9. The method of claim 7, wherein the virus is a LIVP strain of the Lister strain of vaccinia virus.

10. The method of claim 6, wherein monitoring is effected by MRI.

11. The method of claim 6, wherein the virus is a LIVP strain of the Lister strain of vaccinia virus.

12. The method of claim 6, wherein the signal is detectable by magnetic resonance imaging (MRI), single-photon emission computed tomography (SPECT), positron emission tomography (PET), scintigraphy, β+ detector or a γ detector.

13. The method of claim 1, wherein the tumor is a bladder tumor, breast tumor, prostate tumor, glioma tumor, liver tumor, skin tumor, colon tumor, lung tumor, ovarian carcinoma or pancreatic carcinoma or metastasis.

\* \* \* \* \*

UNITED STATES PATENT AND TRADEMARK OFFICE
CERTIFICATE OF CORRECTION

| | | |
|---|---|---|
| PATENT NO. | : 8,586,022 B2 | Page 1 of 1 |
| APPLICATION NO. | : 11/981976 | |
| DATED | : November 19, 2013 | |
| INVENTOR(S) | : Szalay et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 454 days.

Signed and Sealed this
Twenty-fourth Day of March, 2015

Michelle K. Lee
*Director of the United States Patent and Trademark Office*

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gggaaagaca tgaaacgctt a                                              21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
aaacaacgag tgaattagcg ct                                             22